US011931116B2

(12) United States Patent
Krishnaswamy et al.

(10) Patent No.: US 11,931,116 B2
(45) Date of Patent: *Mar. 19, 2024

(54) SYSTEMS AND METHODS FOR GUIDING TISSUE RESECTION

(71) Applicant: THE TRUSTEES OF DARTMOUTH COLLEGE, Hanover, NH (US)

(72) Inventors: Venkataramanan Krishnaswamy, Lebanon, NH (US); Richard J. Barth, Jr., Hanover, NH (US); Keith D. Paulsen, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,606

(22) Filed: Jul. 25, 2022

(65) Prior Publication Data

US 2022/0370154 A1    Nov. 24, 2022

Related U.S. Application Data

(60) Continuation of application No. 16/859,094, filed on Apr. 27, 2020, now Pat. No. 11,395,704, which is a
(Continued)

(51) Int. Cl.
*G06K 9/00* (2022.01)
*A61B 34/00* (2016.01)
(Continued)

(52) U.S. Cl.
CPC .............. *A61B 34/20* (2016.02); *A61B 34/10* (2016.02); *A61B 34/25* (2016.02); *A61B 90/361* (2016.02);
(Continued)

(58) Field of Classification Search
None
See application file for complete search history.

(56) References Cited

U.S. PATENT DOCUMENTS 5,772,654 A    6/1998  Leyva
6,146,377 A *  11/2000 Lee ................. A61B 90/17
                                                600/414
(Continued)

FOREIGN PATENT DOCUMENTS

CN    204274601 U    4/2015
CN    107106115 A    8/2017
(Continued)

OTHER PUBLICATIONS

Extended European Search Report and Opinion for European Patent Application No. 16808451.5 dated Jan. 22, 2019, 8 pages.
(Continued)

*Primary Examiner* — Feng Niu
(74) *Attorney, Agent, or Firm* — Cozen O'Connor

(57) ABSTRACT

A method for guiding resection of local tissue from a patient includes generating at least one image of the patient, automatically determining a plurality of surgical guidance cues indicating three-dimensional spatial properties associated with the local tissue, and generating a visualization of the surgical guidance cues relative to the surface. A system for generating surgical guidance cues for resection of a local tissue from a patient includes a location module for processing at least one image of the patient to determine three-dimensional spatial properties of the local tissue, and a surgical cue generator for generating the surgical guidance cues based upon the three-dimensional spatial properties. A patient-specific locator form for guiding resection of local tissue from a patient includes a locator form surface match-
(Continued)

ing surface of the patient, and a plurality of features indicating a plurality of surgical guidance cues, respectively.

18 Claims, 35 Drawing Sheets

Related U.S. Application Data division of application No. 15/735,907, filed as application No. PCT/US2016/037043 on Jun. 10, 2016, now Pat. No. 10,667,870, which is a continuation of application No. 14/919,411, filed on Oct. 21, 2015, now abandoned, which is a continuation-in-part of application No. 14/000,068, filed as application No. PCT/US2012/025671 on Feb. 17, 2012, now abandoned.

(60) Provisional application No. 62/185,292, filed on Jun. 26, 2015, provisional application No. 62/174,949, filed on Jun. 12, 2015, provisional application No. 61/443,793, filed on Feb. 17, 2011.

(51) Int. Cl.
  *A61B 34/10* (2016.01)
  *A61B 34/20* (2016.01)
  *A61B 90/00* (2016.01)
  *G06T 7/00* (2017.01)
  *G06T 7/33* (2017.01)
  *A61B 17/00* (2006.01)
  *A61B 17/34* (2006.01)

(52) U.S. Cl.
  CPC .............. *G06T 7/0012* (2013.01); *G06T 7/33* (2017.01); *A61B 2017/008* (2013.01); *A61B 2017/3405* (2013.01); *A61B 2034/105* (2016.02); *A61B 2034/107* (2016.02); *A61B 2034/2065* (2016.02); *A61B 2090/365* (2016.02); *A61B 2090/378* (2016.02); *A61B 2090/3908* (2016.02); *A61B 2090/395* (2016.02); *G06T 2207/30068* (2013.01)

(56) References Cited

U.S. PATENT DOCUMENTS

| | | | |
|---|---|---|---|
| 6,282,437 B1 | 8/2001 | Franck et al. | |
| 6,327,491 B1 | 12/2001 | Franklin et al. | |
| 6,529,758 B2 | 3/2003 | Shahidi | |
| 6,589,254 B2* | 7/2003 | Fontenot | A61B 90/17 600/231 |
| 6,671,538 B1 | 12/2003 | Ehnholm et al. | |
| 6,690,964 B2 | 2/2004 | Bieger et al. | |
| 6,754,374 B1 | 6/2004 | Miller et al. | |
| 7,103,399 B2 | 9/2006 | Miga et al. | |
| 7,206,626 B2 | 4/2007 | Quaid, III | |
| 7,597,104 B2* | 10/2009 | Zheng | A61B 6/04 5/601 |
| 7,651,506 B2 | 1/2010 | Bova et al. | |
| 7,676,021 B2* | 3/2010 | Tsujii | A61B 6/032 378/197 |
| 7,752,768 B2* | 7/2010 | Young | A61B 90/39 33/566 |
| 7,885,443 B2 | 2/2011 | Zingaretti et al. | |
| 8,066,708 B2 | 11/2011 | Lang et al. | |
| 8,144,959 B2 | 3/2012 | Zingaretti et al. | |
| 8,391,954 B2 | 3/2013 | Quaid, III | |
| 8,670,816 B2 | 3/2014 | Green et al. | |
| 8,747,382 B2 | 6/2014 | D'Souza et al. | |
| 8,948,851 B2* | 2/2015 | Leblond | A61B 5/0062 850/31 |
| 9,072,531 B2 | 7/2015 | Fitz et al. | |
| 9,168,153 B2 | 10/2015 | Bettenga et al. | |
| 9,198,678 B2 | 12/2015 | Frey et al. | |
| 9,308,053 B2 | 4/2016 | Bojarski et al. | |
| 9,314,256 B2 | 4/2016 | Fitz et al. | |
| 9,314,305 B2 | 4/2016 | Jenkins et al. | |
| 9,364,294 B2 | 6/2016 | Razzaque et al. | |
| 9,381,025 B2 | 7/2016 | Fitz et al. | |
| 9,427,213 B2* | 8/2016 | Suzuki | A61B 8/4455 |
| 9,433,389 B2 | 9/2016 | D'Souza et al. | |
| 9,439,564 B2 | 9/2016 | Trumer et al. | |
| 9,510,853 B2 | 12/2016 | Aljuri et al. | |
| 9,615,840 B2* | 4/2017 | Iannotti | A61B 17/1778 |
| 9,649,167 B2 | 5/2017 | Miyamoto | |
| 9,848,904 B2 | 12/2017 | Aljuri et al. | |
| 10,013,777 B2 | 7/2018 | Mariampillai et al. | |
| 10,130,378 B2 | 11/2018 | Bryan | |
| 10,136,950 B2 | 11/2018 | Schoenefeld | |
| 10,178,955 B2 | 1/2019 | Rucker et al. | |
| 10,231,745 B2 | 3/2019 | Geebelen et al. | |
| 10,314,559 B2 | 6/2019 | Razzaque et al. | |
| 10,376,327 B2 | 8/2019 | Jenkins et al. | |
| 10,667,870 B2 | 6/2020 | Krishnaswamy et al. | |
| 10,973,589 B2 | 4/2021 | Krishnaswamy et al. | |
| 2002/0077533 A1 | 6/2002 | Bieger et al. | |
| 2002/0099264 A1* | 7/2002 | Fontenot | A61B 90/17 600/130 |
| 2005/0148859 A1 | 7/2005 | Miga et al. | |
| 2006/0212044 A1* | 9/2006 | Bova | A61B 90/10 606/130 |
| 2007/0198022 A1 | 8/2007 | Lang et al. | |
| 2008/0123921 A1 | 5/2008 | Gielen et al. | |
| 2008/0123927 A1 | 5/2008 | Miga et al. | |
| 2008/0230074 A1* | 9/2008 | Zheng | A61B 6/04 128/869 |
| 2008/0243127 A1 | 10/2008 | Lang et al. | |
| 2008/0247622 A1* | 10/2008 | Aylward | A61B 90/36 382/131 |
| 2009/0003666 A1* | 1/2009 | Wu | G06T 7/0012 382/128 |
| 2009/0022269 A1* | 1/2009 | Tsujii | A61B 6/032 378/17 |
| 2009/0177081 A1 | 7/2009 | Joskowicz et al. | |
| 2009/0264968 A1 | 10/2009 | Green | |
| 2010/0023122 A1* | 1/2010 | Young | A61B 90/39 623/7 |
| 2011/0213373 A1 | 9/2011 | Fitz et al. | |
| 2011/0213377 A1 | 9/2011 | Lang et al. | |
| 2011/0275932 A1* | 11/2011 | Leblond | A61B 5/0062 600/425 |
| 2012/0004518 A1 | 1/2012 | D'Souza et al. | |
| 2012/0143267 A1* | 6/2012 | Iannotti | A61B 17/151 606/86 R |
| 2012/0179026 A1 | 7/2012 | Simon et al. | |
| 2012/0234329 A1* | 9/2012 | Vancraen | A61B 90/11 128/845 |
| 2012/0290272 A1 | 11/2012 | Bryan | |
| 2013/0018232 A1 | 1/2013 | D'Souza et al. | |
| 2013/0197357 A1 | 8/2013 | Green et al. | |
| 2013/0279782 A1 | 10/2013 | Trumer et al. | |
| 2014/0037161 A1 | 2/2014 | Rucker et al. | |
| 2014/0074441 A1 | 3/2014 | Fitz et al. | |
| 2014/0142426 A1 | 5/2014 | Razzaque et al. | |
| 2014/0333617 A1 | 11/2014 | Miyamoto | |
| 2014/0343404 A1 | 11/2014 | Razzaque et al. | |
| 2014/0350614 A1 | 11/2014 | Frey et al. | |
| 2015/0196282 A1 | 7/2015 | Ishida et al. | |
| 2015/0313666 A1 | 11/2015 | Aljuri et al. | |
| 2015/0335344 A1 | 11/2015 | Aljuri et al. | |
| 2016/0078633 A1 | 3/2016 | Tahmasebi Maraghoosh et al. | |
| 2017/0367781 A1* | 12/2017 | Arimura | A61B 6/04 |
| 2019/0053852 A1 | 2/2019 | Schoenefeld | |
| 2022/0051431 A1* | 2/2022 | Jagadeesan | G06V 10/98 |

FOREIGN PATENT DOCUMENTS

| | | |
|---|---|---|
| EP | 3 238 627 A1 | 11/2017 |
| WO | WO 2007/092841 A2 | 8/2007 |

(56) References Cited

FOREIGN PATENT DOCUMENTS

| WO | WO 2011/029934 A1 | 3/2011 |
| WO | WO 2012/112907 A2 | 8/2012 |
| WO | WO 2015/035249 A2 | 3/2015 |

OTHER PUBLICATIONS

Extended European Search Report for European Patent Application No. 22167507.7 dated Sep. 8, 2022, 8 pages.
International Search Report and Written Opinion for International Patent Application No. PCT/US2016/037043 dated Sep. 27, 2016, 6 pages.
Irwin, M. et al., "Registered 3-D Ultrasound and Digital Stereotactic Mammography for Breast Biopsy Guidance", IEEE Transactions on Medical Imaging, 27(3): 391-401 (2008).
Office Action for Chinese Patent Application No. 201680045559.3 dated Mar. 26, 2020, 13 pages.

* cited by examiner

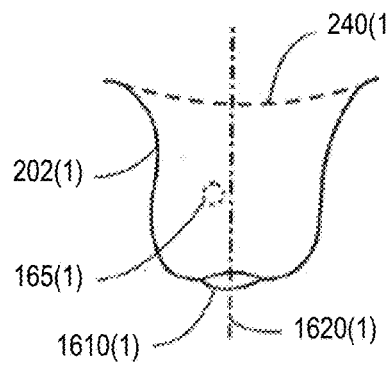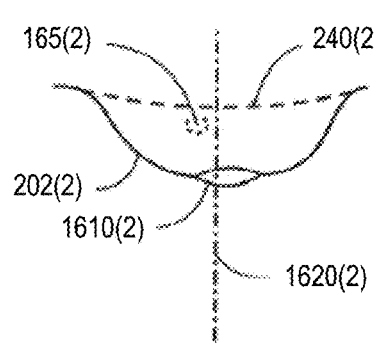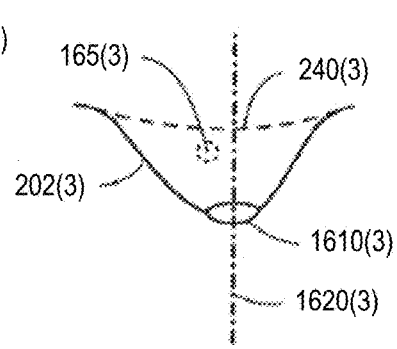
FIG. 16A    FIG. 16B    FIG. 16C
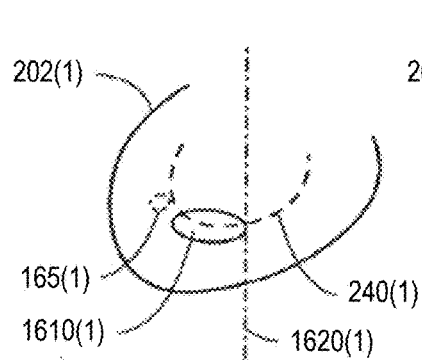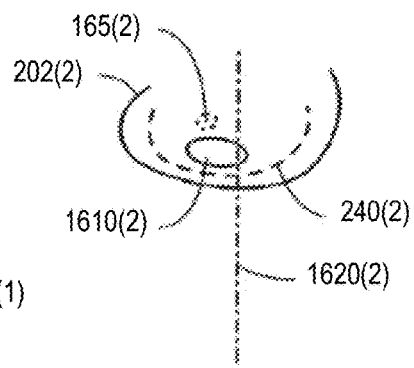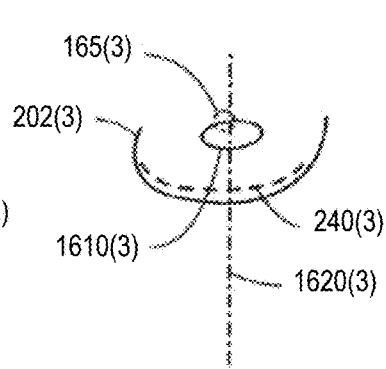
FIG. 17A    FIG. 17B    FIG. 17C

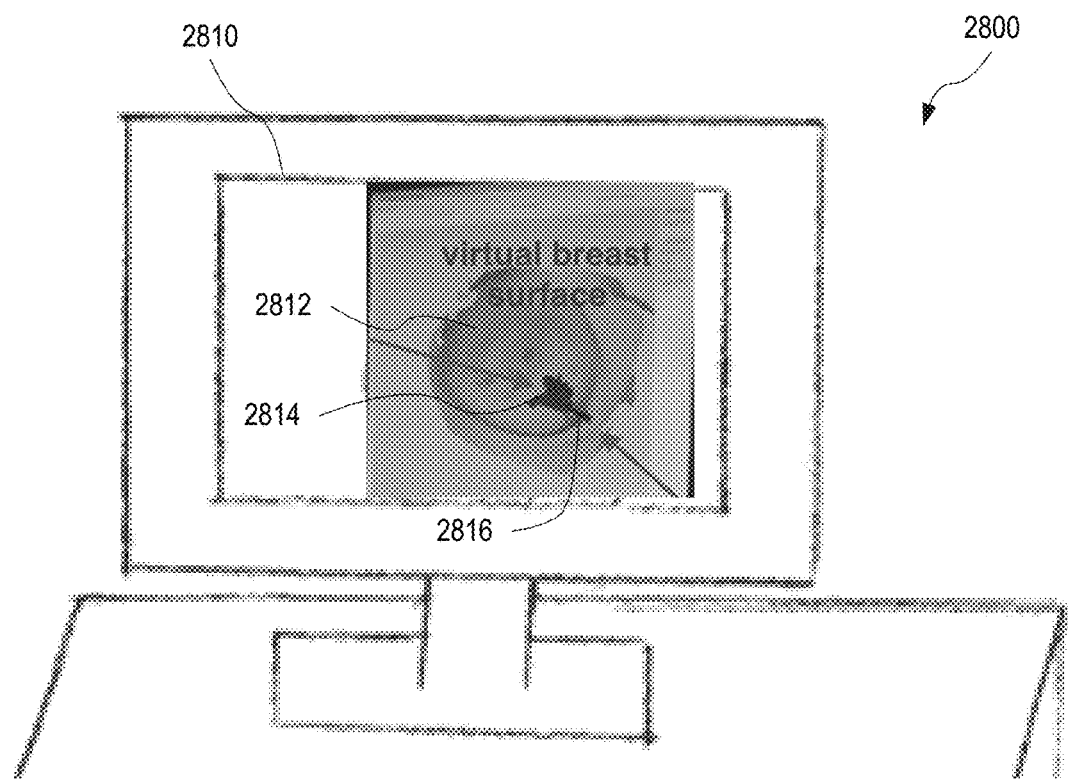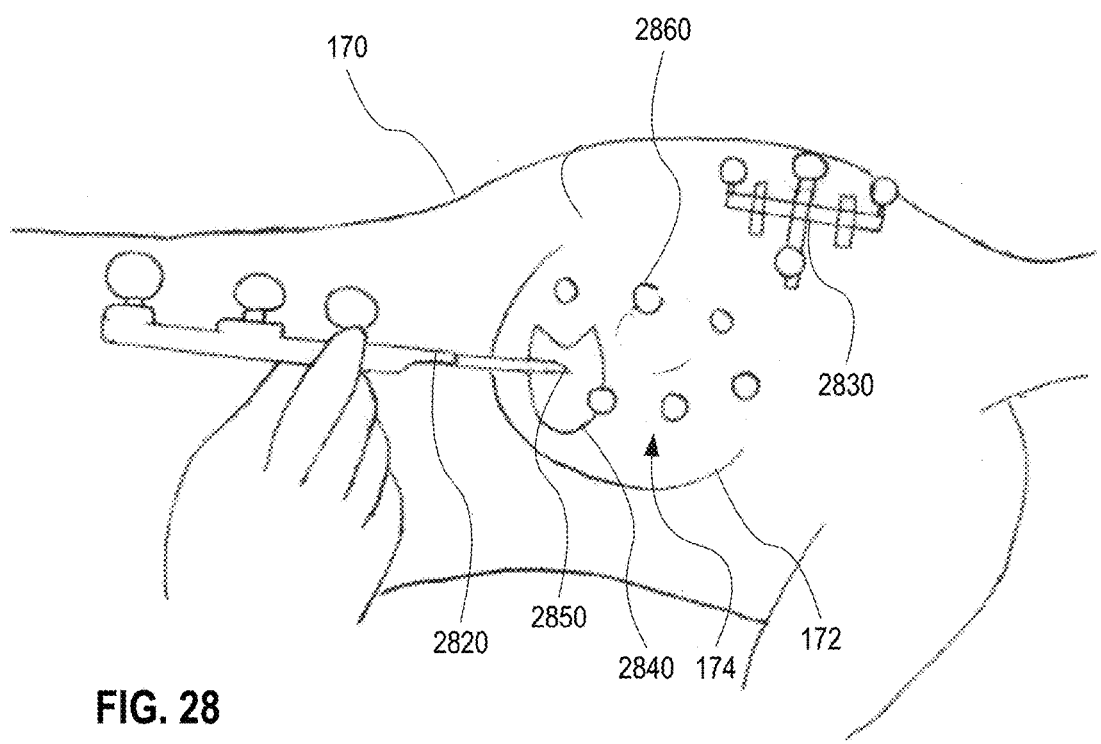
FIG. 28

3000

```
┌─────────────────────────────────────┐
│ TRANSFER SURGICAL GUIDANCE CUES TO  │
│ BREAST SURFACE USING TRACKING STYLUS│
│   AND BREAST MODEL VISUALIZATION    │
│                3010                 │
└─────────────────────────────────────┘
                  │
                  ▼
┌─────────────────────────────────────┐
│ INJECT DYE INTO BREAST USING TRACKED│
│ SYRINGE AS GUIDED BY DISPLAYED TUMOR│
│ MODEL AND/OR SURGICAL GUIDANCE CUES │
│                3020                 │
└─────────────────────────────────────┘
```

```
┌──────────────────────────────────────────────────┐
│ AUTOMATICALLY TRANSFER SURGICAL GUIDANCE CUES TO │
│ BREAST SURFACE USING ROBOTIC STYLUS OPERATED     │
│ ACCORDING TO SURGICAL GUIDANCE CUES AND MODEL OF │
│ BREAST                                           │
│                      3110                        │
└──────────────────────────────────────────────────┘
                         │
                         ▼
┌──────────────────────────────────────────────────┐
│ AUTOMATICALLY INJECT DYE INTO BREAST USING ROBOTIC│
│ SYRINGE OPERATED ACCORDING TO SURGICAL GUIDANCE   │
│ CUES AND MODEL OF BREAST                          │
│                      3120                         │
└──────────────────────────────────────────────────┘
```

```
GENERATE AT LEAST ONE IMAGE OF BREAST IN SUPINE POSITION ASSOCIATED WITH
RESECTION SURGERY
3210
              ↓
PERFORM METHOD 400 WITHOUT STEP 410
3220
              ↓
PERFORM TISSUE RESECTION
3230
```

```
GENERATE AT LEAST ONE PREOPERATIVE        GENERATE AT LEAST ONE 3D SURFACE
VOLUMETRIC IMAGE OF BREAST IN SUPINE      IMAGE OF BREAST IN SUPINE POSITION
POSITION                                  ASSOCIATED WITH RESECTION SURGERY
3310                                      3320
                    ↓              ↓
        PERFORM METHOD 400 WITH STEPS 412 AND 414
        3330
                          ↓
        PERFORM TISSUE RESECTION
        3340
```

```
┌─────────────────────────────────────────────────────────────────────────┐
│  GENERATE AT LEAST ONE PREOPERATIVE VOLUMETRIC IMAGE OF BREAST IN SUPINE POSITION │
│                                    3610                                  │
│  ┌───────────────────────────────────────────────────────────────────┐  │
│  │              UTILIZE FIDUCIAL MARKERS ON BREAST SURFACE            │  │
│  │                              3612                                  │  │
│  └───────────────────────────────────────────────────────────────────┘  │
└─────────────────────────────────────────────────────────────────────────┘
                                      │
                                      ▼
┌─────────────────────────────────────────────────────────────────────────┐
│  PERFORM STEP 3420 OF METHOD 3400 TO EXTRACT 3D SURFACE MODEL OF BREAST AND │
│   FIDUCIALS FROM PREOPERATIVE VOLUMETRIC IMAGE OF BREAST IN SUPINE POSITION │
│                                    3620                                  │
└─────────────────────────────────────────────────────────────────────────┘
                                      │
                                      ▼
┌─────────────────────────────────────────────────────────────────────────┐
│  PERFORM STEPS 420, 430, AND 438 OF METHOD 400 TO GENERATE PATIENT-SPECIFIC LOCATOR │
│    FORM THAT FITS SURFACE OF BREAST AND INDICATES SURGICAL GUIDANCE CUES AND │
│                                 FIDUCIALS                                │
│                                    3630                                  │
└─────────────────────────────────────────────────────────────────────────┘
                                      ┊
                                      ▼
┌─────────────────────────────────────────────────────────────────────────┐
│   PERFORM STEP 2210, INCLUDING STEP 2212, AND STEP 2220 OF METHOD 2200 TO PLACE │
│  PATIENT-SPECIFIC LOCATOR FORM ON BREAST AND TRANSFER SURGICAL GUIDANCE CUES TO │
│       BREAST BASED UPON FEATURES OF PATIENT-SPECIFIC LOCATOR FORM        │
│                                    3640                                  │
└─────────────────────────────────────────────────────────────────────────┘
                                      ┊
                                      ▼
┌─────────────────────────────────────────────────────────────────────────┐
│  PERFORM STEP 2260, OPTIONALLY PRECEDED BY STEP 2230, OF METHOD 2200 TO PERFORM │
│                             RESECTION SURGERY                            │
│                                    3650                                  │
└─────────────────────────────────────────────────────────────────────────┘
```

FIG. 36

SYSTEMS AND METHODS FOR GUIDING TISSUE RESECTION

CROSS-REFERENCES TO RELATED APPLICATIONS

The present application is a continuation of U.S. patent application Ser. No. 16/859,094, filed Apr. 27, 2020, which is a divisional of U.S. patent application Ser. No. 15/735,907 with a § 371 date of Dec. 12, 2017, now U.S. Pat. No. 10,667,870, which is a 35 U.S.C. § 371 filing of International Application No. PCT/US2016/037043, filed Jun. 10, 2016, which claims priority to U.S. patent application Ser. No. 14/919,411 filed on Oct. 21, 2015, to U.S. Provisional Patent Application Ser. No. 62/185,292 filed on Jun. 26, 2015, and to U.S. Provisional Patent Application Ser. No. 62/174,949 filed on Jun. 12, 2015. U.S. patent application Ser. No. 14/919,411 is also a continuation-in-part of U.S. patent application Ser. No. 14/000,068 filed on Oct. 22, 2013, which is a 35 U.S.C. § 371 filing of International Patent Application Serial No. PCT/US2012/025671 filed on Feb. 17, 2012, which claims priority to U.S. Provisional Patent Application Ser. No. 61/443,793 filed on Feb. 17, 2011. All of the above-identified applications are incorporated herein by reference in their entireties.

U.S. GOVERNMENT RIGHTS

This invention was made with Government support under NIH Grant No. R21CA182956 awarded by the National Cancer Institute under the National Institutes of Health. The Government has certain rights in this invention.

BACKGROUND

Tissue removal surgery is frequently assisted by navigation technology to guide the surgical procedure in real time. For example, a biopsy may be guided by ultrasound imaging to ensure that the biopsy is performed at the required location, or removal of the intervertebral disc from a spinal segment may be guided by fluoroscopic x-ray guidance to avoid damaging the spinal cord or nerve roots. Cancer-related tissue removal procedures generally require particularly high accuracy. When performing a biopsy of tissue suspected to be cancerous, proper diagnosis relies on sample retrieval from tumor, hence from a specified location, not from nearby normal tissues. When surgically removing a tumor, any cancerous tissue inadvertently left behind may be detrimental to the patient.

Traditionally, breast tumor resection is guided by a wire penetrating the breast to reach the tumor or a radio-opaque clip placed within the tumor. Breast tumor resection is the removal of the cancerous tissue only, as opposed to removal of the whole breast. The radio-opaque clip may be placed in the tumor during a biopsy procedure. The wire insertion is guided by imaging, for example ultrasound imaging, magneto resonance imaging (MRI), or mammography. It is challenging to ensure that the entire perimeter of the tumor is removed including any filaments or fimbriae. Frequently, since some cancerous tissue remains in the breast after the resection surgery, breast tumor resection is usually accompanied by radiation treatment with the intent of destroying any unremoved cancerous tissue. Nevertheless, about one in four women having undergone breast tumor resection need to return for further resection of cancerous tissue at or near the site of the original resection.

SUMMARY

In an embodiment, a method for guiding resection of local tissue from a patient includes generating at least one image of the patient, wherein the at least one image includes an image of the local tissue and an image of at least a portion of surface of the patient. The method further includes automatically determining, at least in part based upon the at least one image, a plurality of surgical guidance cues indicating three-dimensional spatial properties associated with the local tissue, and generating a visualization of the surgical guidance cues relative to the surface.

In an embodiment, a system for generating surgical guidance cues for resection of a local tissue from a patient includes a location module for processing at least one image of the patient to determine three-dimensional spatial properties of the local tissue, and a surgical cue generator for generating the surgical guidance cues based upon the three-dimensional spatial properties.

In an embodiment, a patient-specific locator form for guiding resection of local tissue from a patient includes a locator form surface that matches the surface of the patient near location of the local tissue, such that the patient-specific locator form fits the surface of the patient near the location of the local tissue. The patient-specific locator form further includes a plurality of features indicating a plurality of surgical guidance cues, respectively.

BRIEF DESCRIPTION OF THE DRAWINGS

The foregoing and other features and advantages of the disclosure will be apparent from the more particular description of embodiments, as illustrated in the accompanying drawings, in which like reference characters refer to the same parts throughout the different figures. The drawings are not necessarily to scale, emphasis instead being placed upon illustrating the principles of the disclosure.

FIGS. 16A-C and 17A-C illustrate exemplary tissue displacement between prone and supine positions of a breast, according to an embodiment.

FIG. 28 illustrates a navigation system for guiding resection of a tumor from a breast with the aid of surgical guidance cues, according to an embodiment.

FIG. 30 illustrates a method for transferring surgical guidance cues to a breast using a navigation system and tracking devices, according to an embodiment.

FIG. 31 illustrates a method for automatically transferring surgical guidance cues to a breast using a robotic system, according to an embodiment.

FIG. 32 illustrates a method for guiding tissue, which does not require image registration, according to an embodiment.

FIG. 33 illustrates a method for guiding tumor resection based upon preoperative supine volumetric image(s) and supine 3D surface image(s) representative of the supine position used during resection surgery, according to an embodiment.

FIG. 36 illustrates a method for guiding resection of a tumor, using a patient-specific locator form manufactured based upon volumetric and surface data obtained from the same preoperative volumetric image(s), according to an embodiment.

DETAILED DESCRIPTION OF THE EMBODIMENTS

Figure 1:
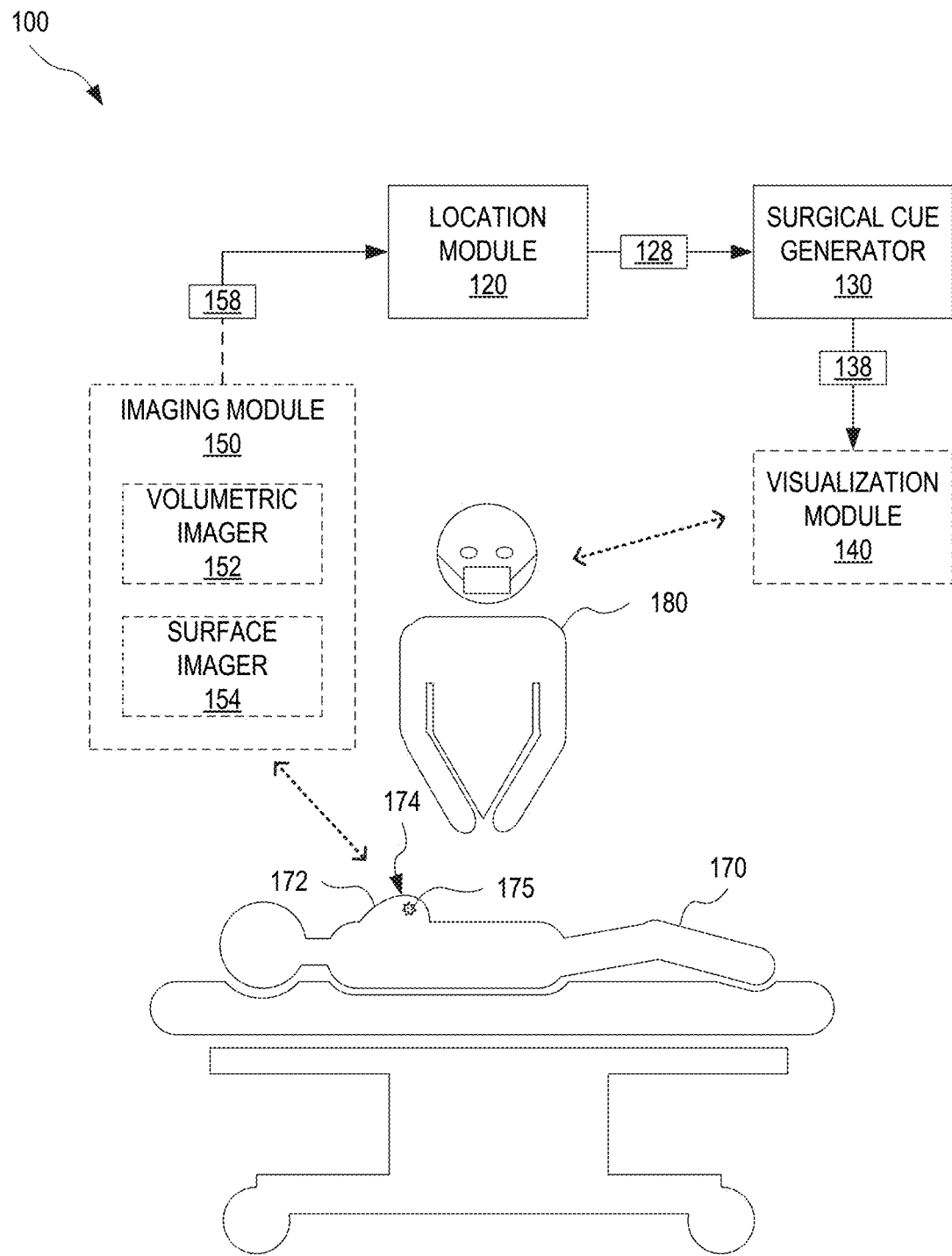
FIG. 1 illustrates a system for guiding resection of a tumor from a breast of a patient, according to an embodiment.

FIG. 1 illustrates one exemplary system 100 for guiding resection of a tumor 175 from a breast 172 of a patient 170. The resection surgery is performed with patient 170 in supine position, i.e., with patient 170 laying on her back and breast 172 facing upwards. System 100 utilizes supine images 158 of breast 172 to determine geometrical properties of the resection surgery to remove tumor 175, and also generate surgical guidance cues 138 to guide the resection surgery. Herein, a "supine image" refers to an image of patient 170 in the supine position. Each supine image 158 is an image of breast 172 corresponding to breast 172 being in the supine position and substantially in the position in which the resection surgery is performed. Supine image 158 is captured while patient 170 is in the supine position or, alternatively, generated from a combination of images captured in the supine and prone positions. Surgical guidance cues 138 directly and/or indirectly indicate three-dimensional (3D) spatial properties of tumor 175 in the supine position used during resection surgery.

System 100 includes a location module 120 that processes at least one supine image 158 of breast 172 to determine 3D spatial properties 128 of tumor 175. System 100 further includes a surgical cue generator 130 that determines surgical guidance cues 138. A surgeon 180 uses surgical guidance cues 138 to perform resection surgery on patient 170 to remove tumor 175. Herein, a "surgeon" may refer to one or more humans, one or more computer systems, one or more robotic devices, and/or a combination thereof.

In an embodiment, system 100 further includes a visualization module 140 that visualizes surgical guidance cues 138 for surgeon 180. In one example, visualization module 140 displays surgical guidance cues 138 on a computer-generated model of breast 172.

In an embodiment, system 100 includes an imaging module 150 that captures the at least one supine image 158, or alternatively captures one or more images, from which at least one supine image 158 may be generated. The at least one supine image 158 includes an image of tumor 175 and an image of at least a portion of surface 174 of breast 172. Imaging module 150 includes a volumetric imager 152 that captures a 3D image of breast 172 including an image of tumor 175. Volumetric imager 152 may include a magnetic resonance imaging (MRI) scanner, an ultrasound imaging device, a computerized tomography (CT) scanner, a mammography X-Ray instrument, and/or another volumetric imaging system known in the art. Imaging module 150 may also include a surface imager 154 that captures a 3D surface image of at least a portion of surface 174. Surface imager 154 may include a stereo camera, a structured-light imaging device, an optical-scattering device, and/or an optical surface imager known in the art. In embodiments where imaging module 150 does not include surface imager 154, at least one volumetric image captured by volumetric imager 152 includes an image of surface 174 or a portion thereof. For example, a portion of surface 174 may be identifiable in a magnetic resonance (MR) image of breast 172.

Figure 2A:
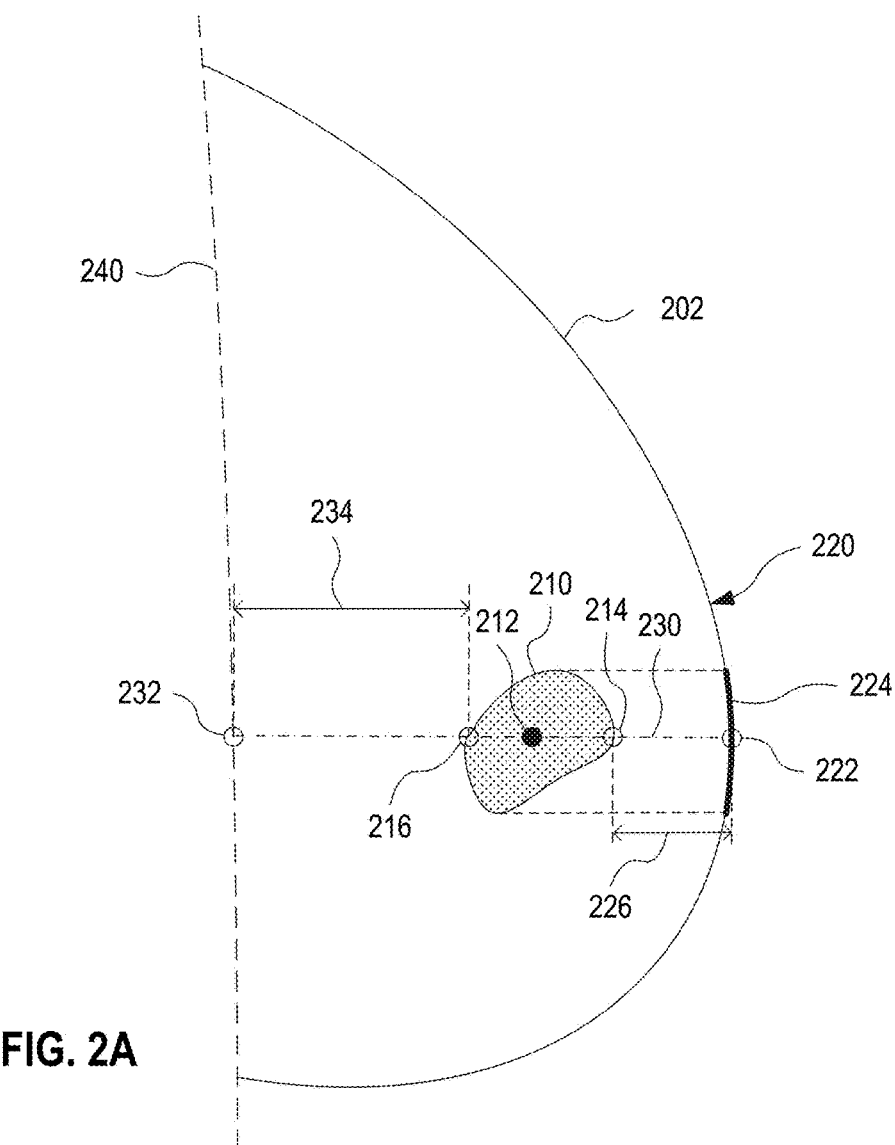
FIGS. 2A and 2B illustrate exemplary surgical guidance cues for guiding resection of a tumor.
Figure 2B:
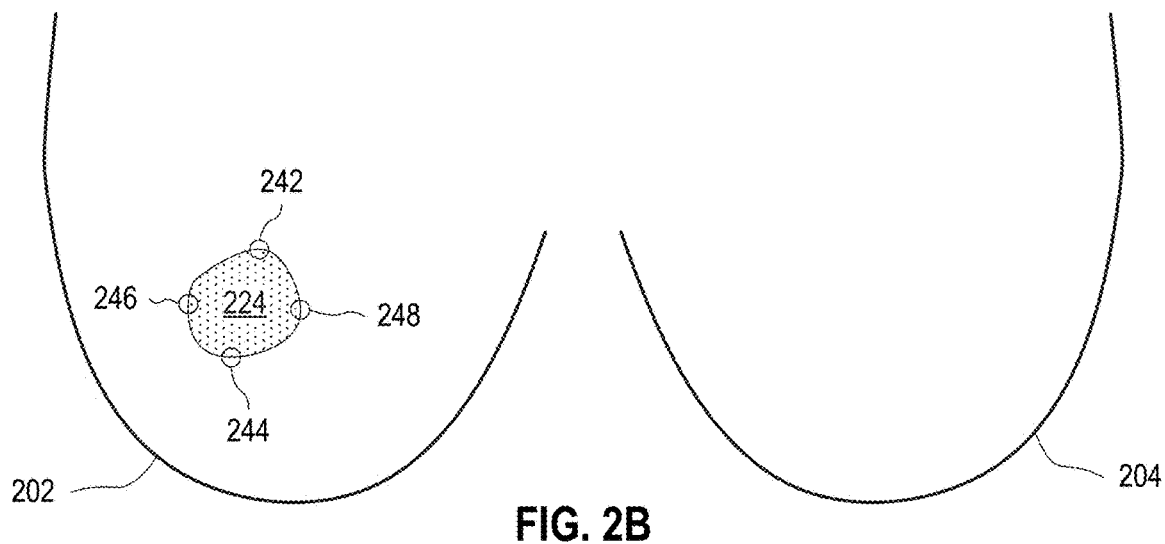

FIGS. 2A and 2B illustrate exemplary surgical guidance cues 138 for guiding resection of tumor 175. FIG. 2A is a cross sectional, lateral view of a right breast 202. Right breast 202 is an example of breast 172. FIG. 2B is an anterior (frontal) view of right breast 202 and an associated left breast 204. FIGS. 2A and 2B are best viewed together. Breast 202 has a tumor 210. Tumor 210 is an example of tumor 175. Breast 202 has a surface 220. Surface 220 is an example of surface 174. FIG. 2A further indicates the chest wall 240 at breast 202.

Exemplary surgical guidance cues 138 include (a) the position of point 222 which is the point of surface 220 closest to tumor 210, (b) the projection 224 of tumor 210 onto surface 220 along line-of-sight 230 from centroid 212 to point 222, (c) the anterior margin 214 of tumor 175 (i.e., point of tumor 210 where line-of-sight 230 intersects the anterior perimeter of tumor 175), which may be indicated as distance 226 between anterior margin 214 and point 222, and/or (d) the posterior margin 216 of tumor 175 (i.e., the point of tumor 210 where line-of-sight 230 intersects the posterior perimeter of tumor 175), which may be indicated as distance 234 between posterior margin 216 and point 232 where line-of-sight 230 intersects chest wall 240.

Optionally, projection 224 is indicated as a set of surgical guidance cues 138 including one or more margins of projection 224 such as the position of cranial margin 242 (the upwards extreme of projection 224, wherein upwards is in direction of the patient's head), the position of caudal margin 244 (the downwards extreme of projection 224, wherein downwards is in direction of the patient's feet), the position of lateral margin 246 (the most lateral point of projection 224), and/or the position of medial margin 248 (the most medial point of projection 224).

In certain examples of use, the definitions of cranial margin 242, caudal margin 244, lateral margin 246, and medial margin 248 incorporate a safety margin, such that each of cranial margin 242, caudal margin 244, lateral margin 246, and medial margin 248 is defined as the respective upwards, downwards, lateral, and medial extremes of a body that is the tumor plus an additional volumetric safety margin. The additional volumetric safety margin is, in some embodiments, about a centimeter in extent, such as between 0.5 and 2.0 centimeters. The additional volumetric safety margin may be calculated using a standard uniform mesh re-sampling technique.

Figure 2C:
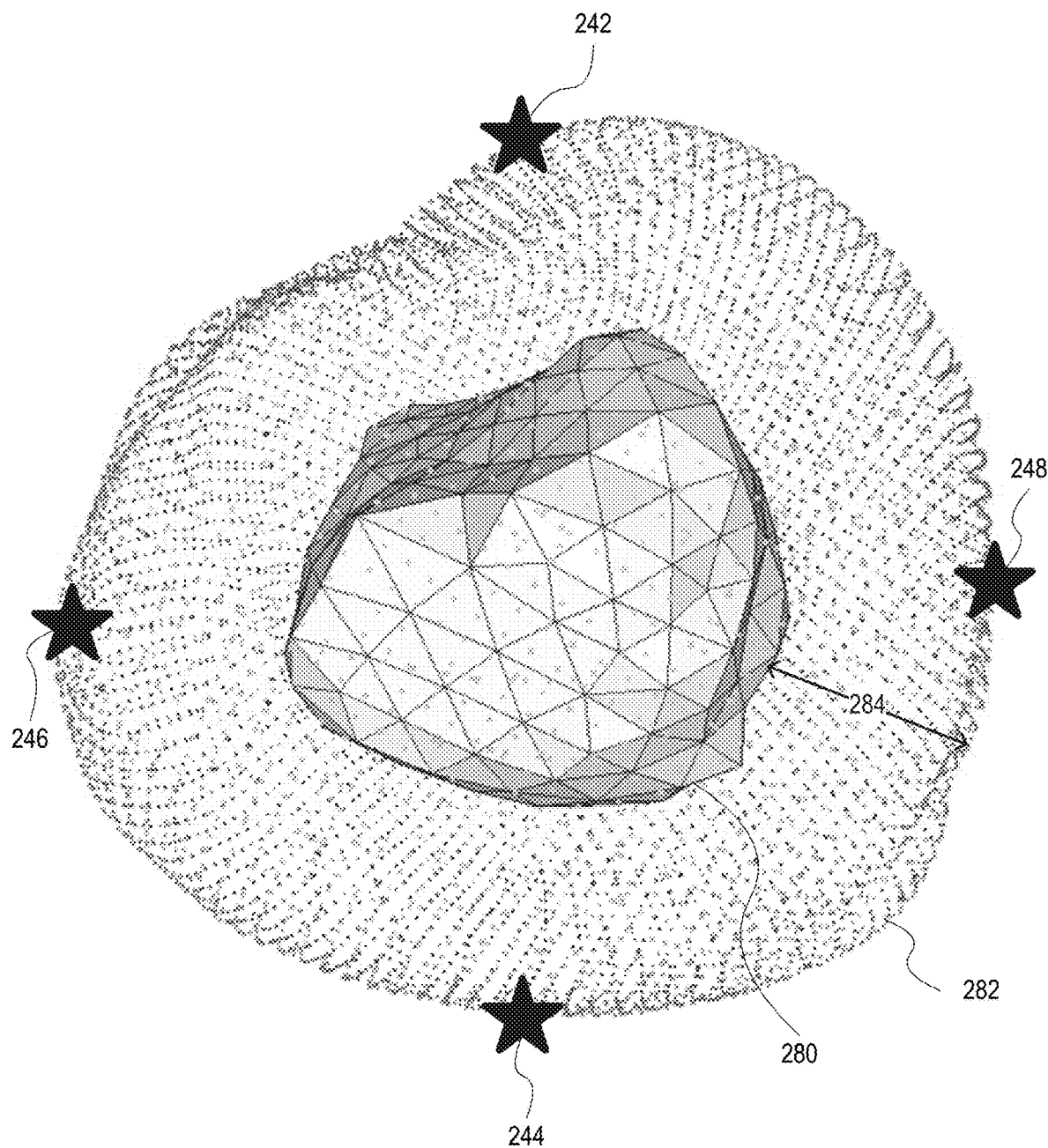
FIG. 2C shows exemplary tumor margins that include a volumetric safety margin.

FIG. 2C shows exemplary tumor margins that include a volumetric safety margin. A model 280 of tumor 175 is extended by a volumetric safety margin 282 with thickness 284. Thickness 284 may be about a centimeter in extent, such as between 0.5 and 2.0 centimeters. Cranial margin 242, caudal margin 244, lateral margin 246, and medial margin 248 are defined as the respective upwards, downwards, lateral, and medial extremes of safety margin 282. Safety margin 282 may be truncated by the boundary of breast 172 in scenarios where tumor 175 is relatively close to a boundary of breast 172.

Other exemplary surgical guidance cues 138 include the position of centroid 212, the outline of tumor 210, and/or the full volumetric extent of tumor 210. Furthermore, surgical guidance cues 138 may include additional positions, for example to account for tumors 210 of complex geometry. In one such example, surgical guidance cues 138 includes other positions on the perimeter of tumor 210, or within tumor 210, optionally in addition to one or more of the surgical guidance cues discussed above.

In an alternative embodiment, point 222 is defined as the incision point for the resection surgery to remove tumor 210 from breast 202. In this embodiment, point 222 is not necessarily the point of surface 220 closest to tumor 210. Point 222 may be a user-defined incision point. For example, surgeon 180 may choose an incision point based at least in part upon cosmetic considerations, considerations of the surface tissue of breast 202 (for example the presence of scar tissue), or practical considerations such as ease of access to the incision point.

Figure 3:
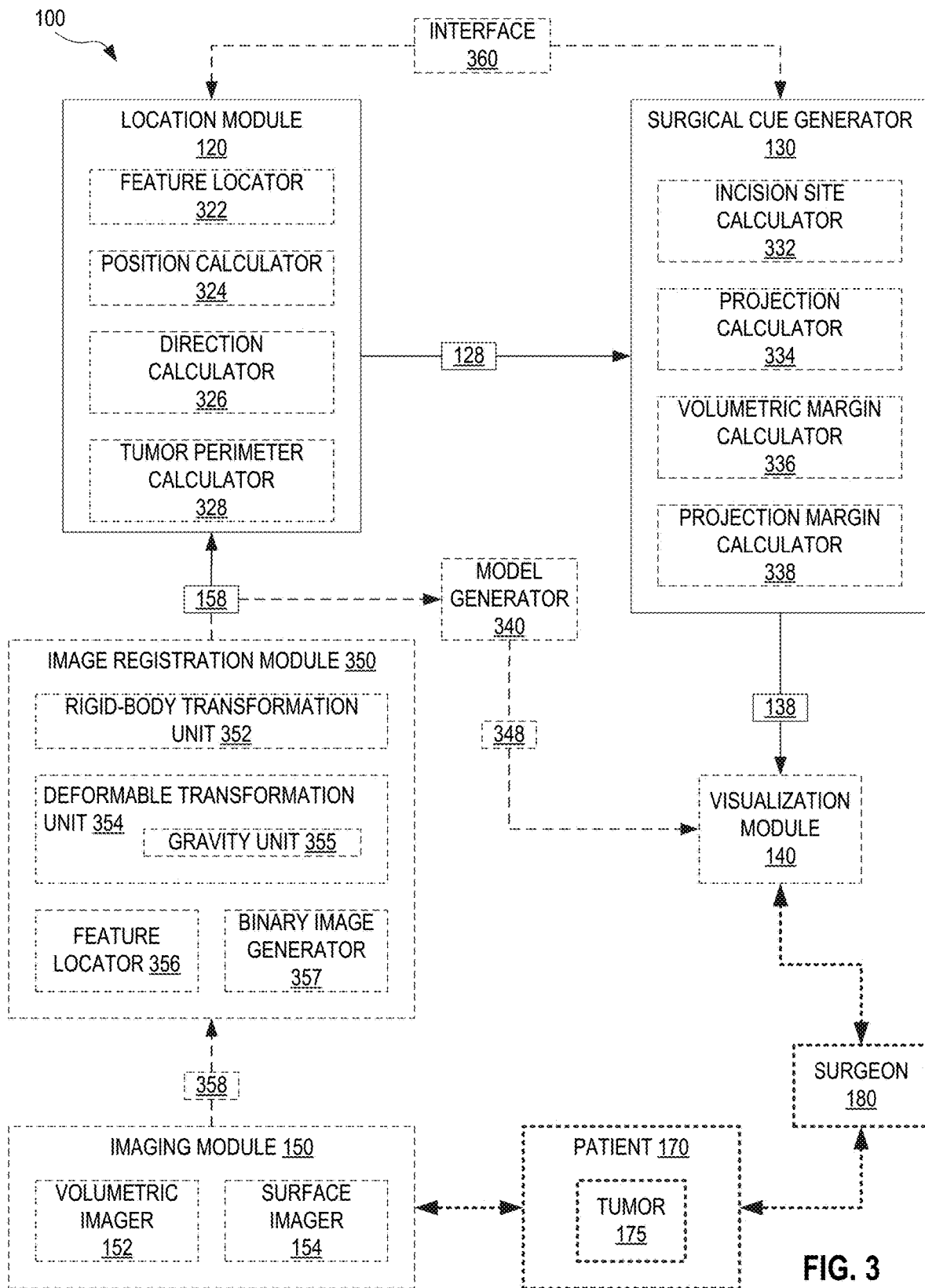
FIG. 3 shows the system of FIG. 1 in further detail, according to an embodiment.

FIG. 3 shows system 100 in further detail. Location module 120 may include one or more of a feature locator 322, a position calculator 324, a direction calculator 326, and a tumor perimeter calculator 328. Feature locator 322 identifies one or more features in supine images 158, such as tumor 175 and at least a portion of surface 174. Position calculator 324 determines positions such as the position of centroid 212 and/or the position of point 222. Direction calculator 326 determines line-of-sight 230 and/or vector(s) along line-of-sight 230. Tumor perimeter calculator 328 determines the position of the perimeter of tumor 175 and/or certain points on the perimeter of tumor 175 such as anterior margin 214 and posterior margin 216. Location module 120 may output items calculated by position calculator 324, direction calculator 326, and/or tumor perimeter calculator 328 as 3D spatial properties 128.

Surgical cue generator 130 may include one or more of an incision site calculator 332, a projection calculator 334, a volumetric margin calculator 336, and a projection margin calculator 338. Incision site calculator 332 determines an optimal incision site for resection surgery to remove tumor 175 based upon 3D spatial properties 128. In one implementation, incision site calculator 332 outputs point 222, determined by position calculator 324, as the incision site. Projection calculator 334 determines projection 224 based upon 3D spatial properties 128, for example from line-of-sight 230 determined by direction calculator 326, the perimeter of tumor 175 determined by tumor perimeter calculator 328, and additional positional information spatially relating the perimeter of tumor 175 to surface 220 as determined by position calculator 324. Volumetric margin calculator 336 determines the position of one or more margins of tumor 175 based upon 3D spatial properties 128. In one implementation, volumetric margin calculator 336 determines distance 226 and/or distance 234. In this implementation, volumetric margin calculator 336 may determine distance 226 from anterior margin 214 and point 222 determined by tumor perimeter calculator 328 and position calculator 324, respectively. Also in this implementation, volumetric margin calculator 336 may determine distance 234 from posterior margin 216 and point 222 determined by tumor perimeter calculator 328 and position calculator 324, respectively. In another example, volumetric margin calculator outputs the position of anterior margin 214 and/or the position of posterior margin 216, as determined by location module 120. Projection margin calculator 338 determines the position of one or more margins of projection 224 such as the positions of cranial margin 242, caudal margin 244, lateral margin 246, and/or medial margin 248, for example based upon line-of-sight 230 and an at least partial perimeter of tumor 175 determined by direction calculator 326 and tumor perimeter calculator 328, respectively. Projection margin calculator 338 may utilize additional positional information spatially relating the perimeter of tumor 175 to surface 220 as determined by position calculator 324. Surgical cue generator 130 outputs one or more items determined by incision site calculator 332, projection calculator 334, volumetric margin calculator, and/or projection margin calculator 338 as surgical guidance cues 138.

In certain embodiments, system 100 includes a model generator 340 that processes at least one supine image 158 to generate a model 348 of breast 172. In one example, model 348 includes a volumetric map of at least a portion of breast 172 including tumor 175. In another example, model 348 includes a 3D surface map of at least a portion of surface 174. In yet another embodiment, model 348 includes a volumetric map of at least a portion of breast 172 including tumor 175 and at least a portion of surface 174. In a further embodiment, model 348 includes several of the above described maps. In one implementation, system 100 further includes visualization module 140. In this implementation, model generator 340 communicates model 348 to visualization module 140 such that visualization module 140 may superimpose one or more of surgical guidance cues 138 on model 348. Visualization module 140 may display model 348 with one or more of surgical guidance cues 138 superimposed thereon to surgeon 180 and/or communicate model 348 with one or more of surgical guidance cues 138 to an operating room (OR) navigation system, such as an OR navigation system known in the art. In one example, the OR navigation system includes a tracking stylus, the position of which is tracked in relation to model 348 and/or surgical guidance cues 138, such that the tracking stylus may mark one or more surgical guidance cues 138 on breast 172. In another example, the OR navigation system includes an augmented reality system that superimposes model 348 and/or surgical guidance cues 138 on the view of surgeon 180. In yet another example, the OR navigation system includes a stereotactic device, the position of which is tracked in relation to model 348 and/or surgical guidance cues 138, such that the stereotactic device may mark one or more surgical guidance cues 138 on or in breast 172.

In one usage scenario, each supine image 158 is captured by imaging module 150. In another usage scenario, imaging module 150 captures one or more images 358 that need processing to determine supine images 158. For example, the position and shape of breast 172 may differ between (a) the positioning of patient 170 during preoperative imaging of breast 172 upon which surgical guidance cues 138 are at least partly based and (b) the positioning of patient 170 during the resection surgery. In an embodiment, system 100 includes an image registration module 350 that processes one or more images 358, captured when breast 172 is in an initial preoperative position, and at least one additional supine image 358, captured when breast 172 is in substantially the supine position in which the resection surgery is performed, to determine supine image(s) 158. Supine images 158 and images 358 may be grayscale images or color images.

In one example, the initial preoperative position is the same as the supine position in which the resection surgery is performed, and image registration module 350 may serve to register different types of images captured by different imaging modalities, respectively. In this example, image registration module 350 may determine supine image 158 from a volumetric image 358 captured by volumetric image 152 or a third-party volumetric imager, wherein volumetric image 358 is captured while breast 172 is substantially in the position associated with the resection surgery. Image registration module 350 may further determine a 3D surface image 358 captured by surface imager 154, or a third-party surface image, wherein 3D surface image 358 is captured while breast 172 is substantially in the position associated with the resection surgery.

In another example, the initial preoperative position is different from the supine position in which the resection surgery is performed, and image registration module 350 further serves to correct for movement of tissue of breast 172. In this example, image registration module 350 may determine supine image 158 from (a) a volumetric image 358 captured by volumetric image 152, or a third-party volumetric imager, while breast 172 is in a position different from that associated with the resection surgery. Image registration module 350 may further determine a 3D surface image captured by surface imager 154, or a third-party surface image, while the positioning of breast 172 is substantially the same as during the resection surgery. In one implementation, images 358, captured when breast 172 is in a preoperative position different from the position in which the resection surgery is performed, are supine images of breast 172. Even in this case, tissue displacement may exist between the two supine positions. For example, tissue displacement may be caused by a difference in hydration levels of patient 170, and/or the effects of intraoperative surgical incisions compared with the preoperative images. In another implementation, images 358, captured when breast 172 is in a preoperative position different from the position in which the resection surgery is performed, are prone images of breast 172.

Image registration module 350 includes a feature locator 356 that identifies features in images 358. Feature locator 356 facilitates registration of (a) an initial volumetric image 358 captured while breast 172 is in a position different from that associated with the resection surgery, to (b) a resection-associated 3D surface image 358 captured while breast 172 is in the supine position associated with the resection surgery.

In one embodiment, image registration module 350 includes a rigid-body transformation unit 352 that applies a rigid-body transformation to initial volumetric image 358 to register features located in both initial volumetric image 358 and resection-associated 3D surface image 358, as determined by feature locator 356, to register initial volumetric image 358 to resection-associated 3D surface image 358. Rigid-body transformation unit 352 may apply a translation, rotation, and/or a scaling to initial volumetric image 358. Rigid-body transformation unit 352 is applicable, for example, in scenarios where initial volumetric image 358 is a supine image. In another embodiment, image registration module 350 includes a deformable transformation unit 354 that applies a deformable transformation to initial volumetric image 358 to register features located in both initial volumetric image 358 and resection-associated 3D surface image 358, as determined by feature locator 356, to register initial volumetric image 358 to resection-associated 3D surface image 358. Herein, a "deformable" transformation (or registration) refers to a transformation (or registration), respectively, that is potentially non-rigid. The deformable transformation allows accounting for deformation of breast 172 in initial volumetric image 358 relative to resection-associated 3D surface image 358. Deformable transformation unit 354 is applicable in scenarios where initial volumetric image 358 is a prone image, for example. Deformable transformation unit 354 may include a gravity unit 355 that applies a transformation to initial volumetric image 358 according to a gravitational model to account for gravitationally induced tissue displacement between initial volumetric image 358 and resection-associated 3D surface image 358. In one example, deformable transformation unit 354 utilizes gravity unit 355 to transform a prone volumetric image 358 according to a 2G gravitational force towards chest wall 240, to register a prone volumetric image 358 to a supine resection-associated 3D surface image 358. In yet another embodiment, image registration module 350 includes both rigid-body transformation unit 352 and deformable transformation unit 354. Without departing from the scope hereof, resection-associated 3D surface image 358 may be generated from a plurality of captured resection-associated 3D surface images 358. Likewise, initial volumetric image 358 may be generated from a plurality captured initial images 358.

Optionally, image registration module 350 includes a binary image generator 357 that generates a binary version of image 358 to enhance certain features, such as a surface 174.

Although not shown in FIG. 3, location module 120 may operate on captured images 358, and system 100 may implement a position correction module to correct surgical guidance cues 138 instead of correcting captured supine images 358, without departing from the scope hereof. This position correction module would have functionality similar to that of image registration module 350, however configured to operate on 3D spatial properties 128 as opposed to images 358.

In certain embodiments, system 100 includes an interface 360 that receives user input such as the position of a user-defined incision site.

Without departing from the scope hereof, system 100 may be applied to imaging of other portions of patient 170 than breast 172, to guide resection of local tissue from patient 170. System 100 may be extended to guide tumor resection from other body parts and organs, such as the brain or the liver, as well as guide biopsy procedures of, e.g., muscle or bone, and also guide a core needle biopsy of a breast abnormality detected on MRI. As such, tumor 175 may be generalized to local tissue of patient 170, breast 172 may be generalized to a portion of patient 170 associated with the resection surgery, surface 174 may be generalized to a surface of patient 170 near the local tissue and including the incision site for removing the local tissue, and supine image 158 may be generalized to an image of the portion of patient 170 associated with the tissue resection procedure positioned as during the tissue resection procedure. System 100 may further be applied to guide local delivery of markers or to guide delivery of a therapeutic agent to local tissue of patient 170.

Figure 4A:
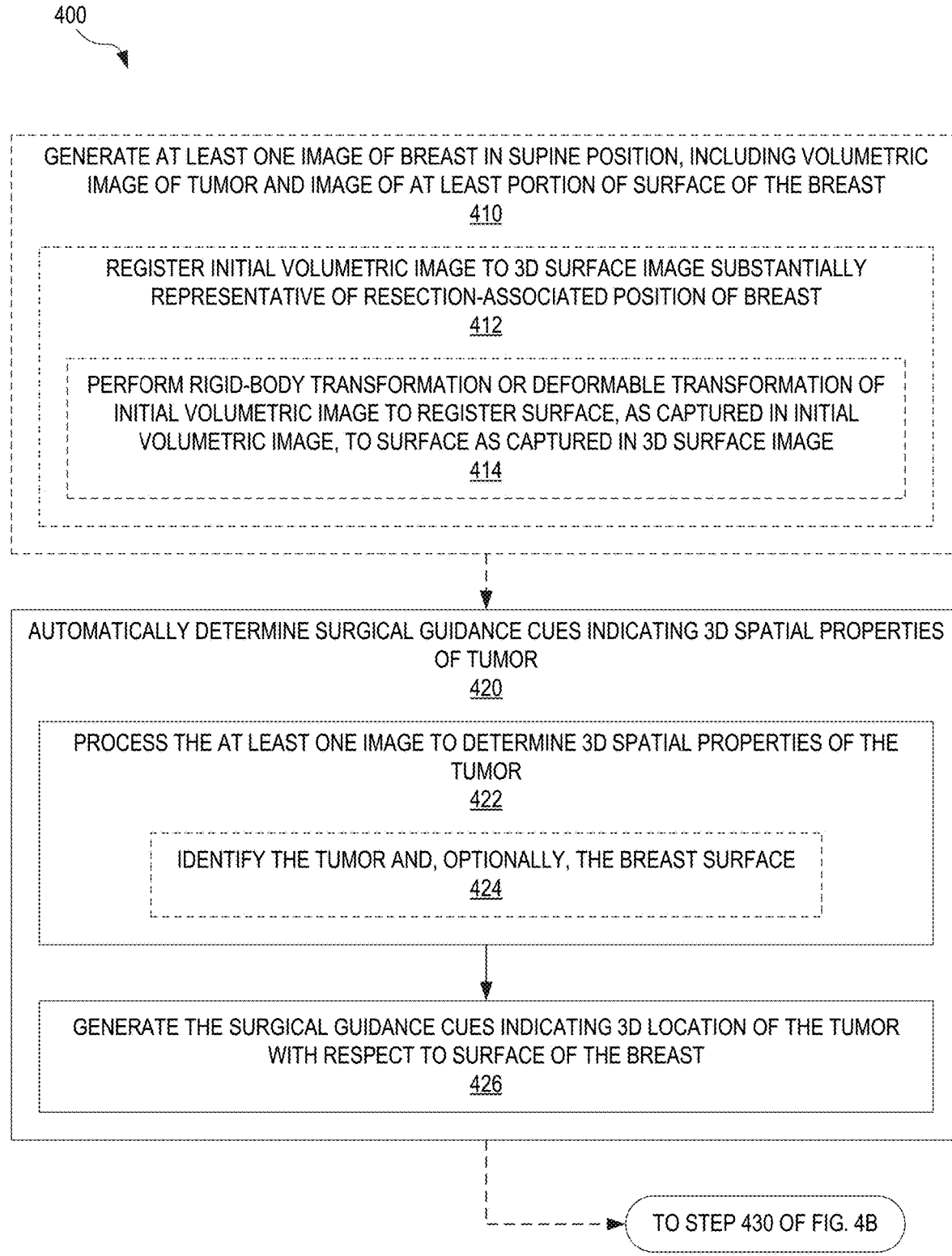
FIGS. 4A and 4B illustrate a method for guiding resection of a tumor from a breast of a patient, according to an embodiment.
Figure 4B:
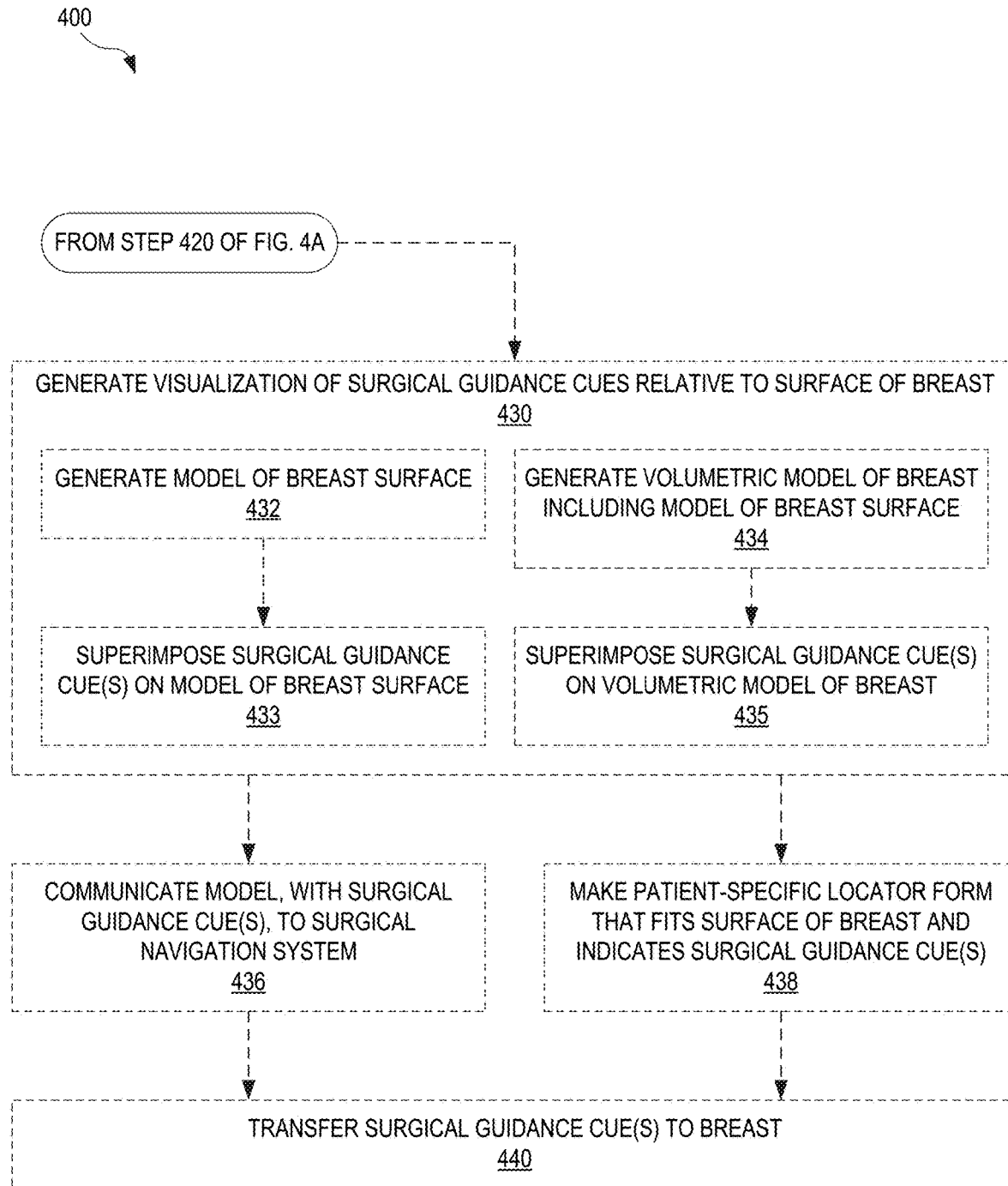

FIGS. 4A and 4B illustrate one exemplary method 400 for guiding resection of a tumor 175. Method 400, or a portion thereof, may be performed by system 100. FIG. 4A shows a first portion of method 400 and FIG. 4B shows a second, optional portion of method 400. FIGS. 4A and 4B are best viewed together.

In one embodiment, method 400 includes a step 410 of generating at least one supine image 158 of breast 172. In one example, imaging module 150 directly captures one or more supine images 158 or images 358 of breast 172. In another example, system 100 receives images 358 from a third party system. In certain embodiments, step 410 includes a step 412 of registering an initial volumetric image 358 of breast 172 to a 3D surface image 358 of surface 174, wherein the 3D surface image 358 is substantially representative of the position of breast 172 associated with the resection surgery. In one example of step 412, image registration module 350 registers an initial volumetric image 358 to a resection-associated 3D surface image 358, as discussed above in reference to FIG. 3. Step 412 may include a step 414 of performing a rigid-body or deformable transformation of initial volumetric image 358 to register surface 174, as captured in initial volumetric image 358, to surface 174 as captured in resection-associated 3D surface image 358. Optionally, step 414 utilizes fiducials on surface 174 identifiable in initial volumetric image 358 and in resection-associated 3D surface image 358. These fiducials may be fiducial markers placed on surface 174 and/or natural features of surface 174, such as a nipple of breast 172. In one example of step 414, image registration module 350 utilizes rigid-body transformation unit 352 as discussed above in reference to FIG. 3. In another example of step 414, image registration module 350 uses deformable transformation unit 354 as discussed above in reference to FIG. 3.

In another embodiment, method 400 does not include step 410 but instead receives supine image(s) 158 generated by a third party system.

In a step 420, method 400 automatically determines surgical guidance cues 138. Step 420 includes steps 422 and 426. Step 422 processes at least one supine image 158 to determine 3D spatial properties 128. Optionally, step 422 includes a step 424 of identifying tumor 175, and optionally surface 174, in supine image(s) 158. In one example of step 422, location module 120 determines 3D spatial properties 128, for example as discussed above in reference to FIG. 3. Location module 120 may utilize position calculator 324, direction calculator 326, and/or tumor perimeter calculator 328 to determine 3D spatial properties 128. Location module 120 may invoke feature locator 322 to identify tumor 175 and/or at least a portion of surface 174 in supine image(s) 158. Step 426 generates surgical guidance cues 138 based upon 3D spatial properties 128. In one example of step 426, surgical cue generator 130 generates surgical guidance cues 138 based upon 3D spatial properties 128, for example as discussed above in reference to FIG. 3. Surgical cue generator 130 may utilize incision site calculator 322, projection calculator 334, volumetric margin calculator 336, and/or projection margin calculator 338 to generate surgical guidance cues 138.

Without departing from the scope hereof, step 422 may process captured images 358, and step 426 may include correcting surgical guidance cues 138, determined based upon captured images 358, to account for tissue displacement of breast 172 between time of initial volumetric image capture and time of resection surgery.

In certain embodiments, method 400 includes a step 430 of visualizing surgical guidance cues 138 relative to surface 174. In one such embodiment, step 430 includes steps 432 and 433. Step 432 generates a model 348 of surface 174, such as a 3D surface map of surface 174, and step 433 superimposes one or more surgical guidance cues 138 on this model 348. In one example of steps 432 and 433, model generator 340 generates a model 348 of surface 174 and visualization module 140 superimposes one or more surgical guidance cues 138 on this model 348. In another such embodiment, step 430 includes steps 434 and 435. Step 434 generates a volumetric model 348 of breast 172 including a model of at least a portion of surface 174, such as a volumetric map of breast 172 including a map of at least a portion of surface 174. Step 435 superimposes one or more surgical guidance cues 138 on this volumetric model 348. Optionally, volumetric model 348 includes at least a portion of chest wall 240. In one example of steps 434 and 435, model generator 340 generates a volumetric model 348 of surface 174 and visualization module 140 superimposes one or more surgical guidance cues 138 on this volumetric model 348.

In an optional step 436, method 400 communicates model 348 with one or more surgical guidance cues 138 superimposed thereon, as generated in step 430, to a surgical navigation system such as an OR navigation system discussed in reference to FIG. 1.

Another optional step 438 produces a patient-specific locator form that fits surface 174 and includes features that indicate one or more of surgical guidance cues 138 or enable transfer of one or more surgical guidance cues 138 onto breast 172. Such a patient-specific locator form is discussed further in reference to FIGS. 20-27.

Method 400 may include a step 440 of transferring one or more surgical guidance cues 138 to surface 174. In one example of step 440, the navigation system of step 436 is used to transfer one or more surgical guidance cues 138 to surface 174. In one example, surgeon 180 uses a tracking stylus to transfer one or more surgical guidance cues 138 to surface 174 and/or uses a tracked stereotactic device to transfer one or more surgical guidance cues 138 to interior locations of breast 172 and, optionally, to surface 174. In another example of step 440, surgeon 180 places the locator form of step 438 on breast 172 and uses features of the locator form to transfer one or more surgical guidance cues 138 to surface 174 and/or interior locations of breast 172.

Without departing from the scope hereof, method 400 may be extended to a more general embodiment of guiding resection of local tissue from patient 170. Method 400 may be extended to guide tumor resection from other body parts and organs, such as the brain or the liver, as well as guide biopsy procedures of, e.g., breast 172, muscle, or bone. As such, tumor 175 may be generalized to local tissue of patient 170, breast 172 may be generalized to a portion of patient 170 associated with the resection surgery, surface 174 may be generalized to a surface of patient 170 near the local tissue and including the incision site for removing the local tissue, and supine image 158 may be generalized to an image of the portion of patient 170 associated with the tissue resection procedure positioned as during the tissue resection procedure. Method 400 may further be applied to guide local delivery of markers or a therapeutic agent to patient 170.

Figure 5A:
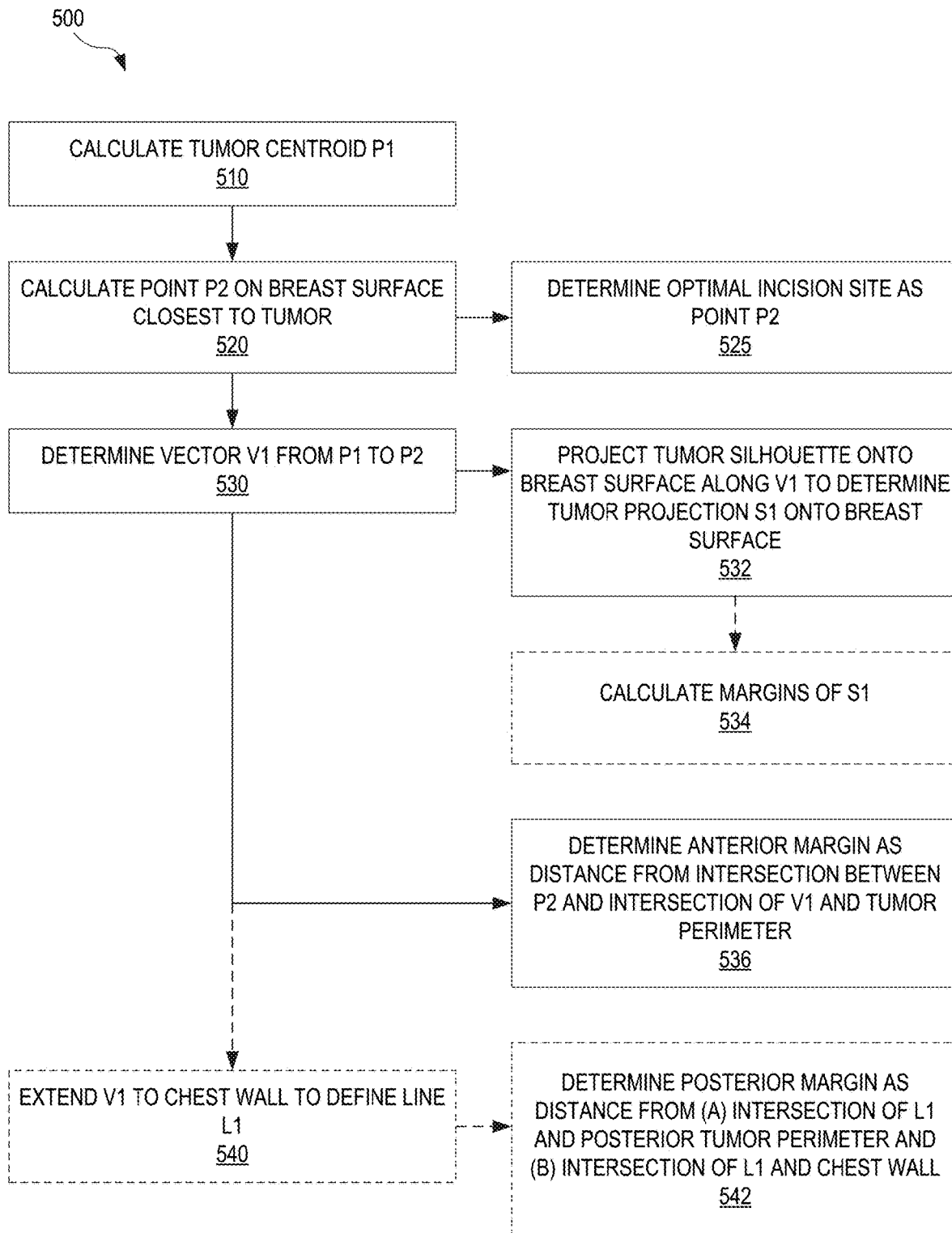
FIG. 5A illustrates a method for generating surgical guidance cues from at least one supine image, according to an embodiment.

FIG. 5A illustrates one exemplary method 500 for generating surgical guidance cues 138 from at least one supine image 158. Method 500 is performed by location module 120 and surgical cue generator 130, for example. Method 500 is an embodiment of step 420 of method 400.

In a step 510, method 500 calculates the position P1 of the centroid of tumor 175. In one example of step 510, position calculator 324 calculates the position of centroid 212.

In a step 520, method 500 calculates the point P2 on surface 174, which is closest to tumor 175. In one example of step 510, position calculator 324 calculates the position of point 222.

In a step 525, method 500 determines the optimal incision site as point P2. In one example of step 525, surgical cue generator 130 determines the optimal incision site as point 222.

In a step 530, method 530 determines a vector V1 from centroid P1 to point P2. In one example of step 530, direction calculator 326 determines a vector from centroid 212 to point 222, wherein this vector is located along line-of-sight 230.

In a step 532, method 500 projects a silhouette of tumor 175 onto surface 174 along vector V1 to determine the projection S1 of tumor 175 onto surface 174. In one example of step 532, projection calculator 334 projects a silhouette of tumor 210 onto surface 220 along line-of-sight 230 to form projection 224. Optionally, method 500 includes a step 534 of determining one or more margins of the projection S1. In one example of step 534, projection margin calculator 338 determines the position of cranial margin 242, caudal margin 244, lateral margin 246, and/or medial margin 248 of projection 224.

In a step 536, method 500 determines the anterior margin of tumor 175 as the distance between (a) the intersection of point P2 and vector V1 and (b) the perimeter of tumor 175. In one example of step 536, volumetric margin calculator 336 determines the position of anterior margin 214 and, subsequently, determines distance 226.

In an optional step 540, method 500 extends vector V1 to the chest wall of patient 170 to define a line L1. In one example of step 540, direction calculator 326 extends line-of-sight 230 from centroid 212 to chest wall 240. Method 500 may include a step 542 of determining the posterior margin of tumor 175 as the distance between (a) the intersection of line L1 and the posterior perimeter of tumor 175 and (b) the intersection of line L1 and the chest wall of patient 170. In one example of step 542, volumetric margin calculator 336 determines the position of posterior margin 216 and, subsequently, determines distance 234.

Figure 5B:
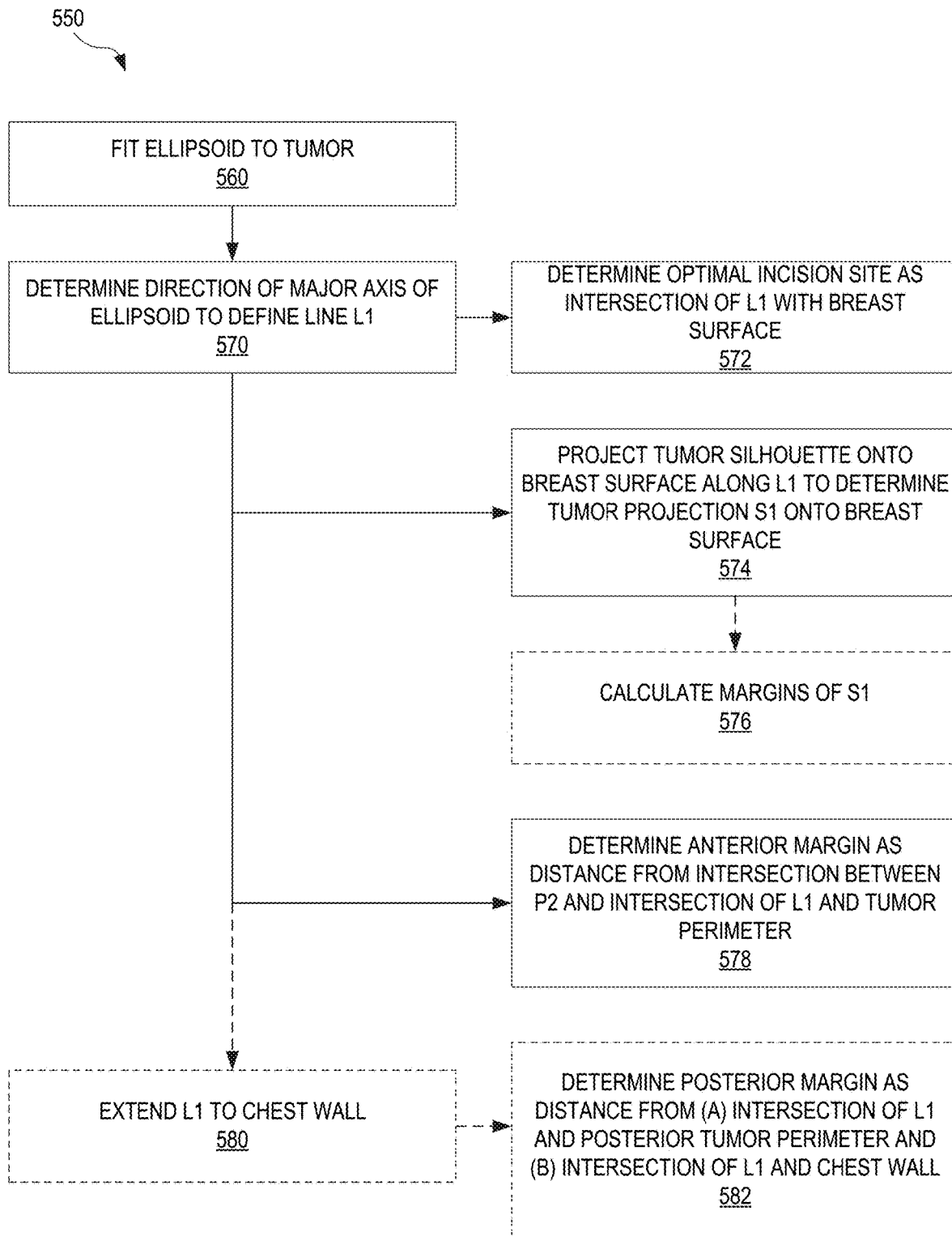
FIGS. 5B and 5C illustrate another method for generating surgical guidance cues from at least one supine image, according to an embodiment.
Figure 5C:
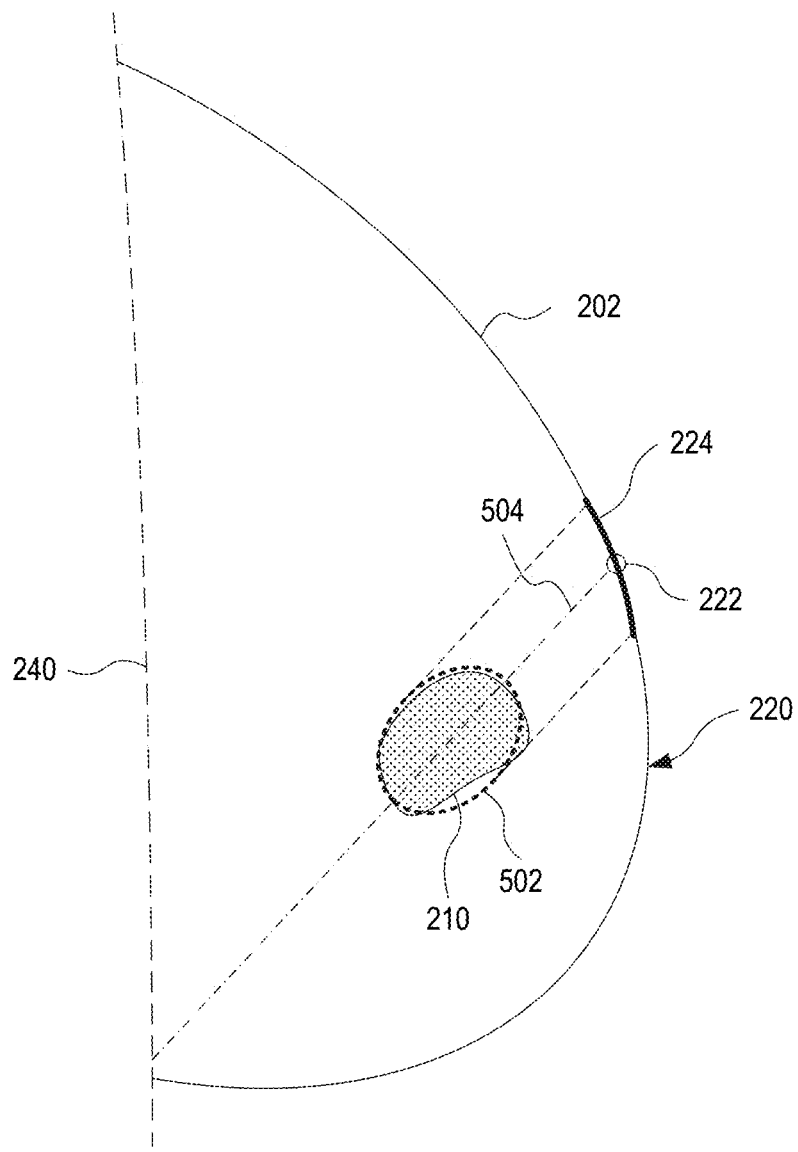

FIGS. 5B and 5C illustrates one exemplary method 550 that is an alternative embodiment of method 500. FIG. 5B is a flowchart for method 550, and FIG. 5C is a diagram showing certain parameters of method 550. FIGS. 5B and 5C are best viewed together.

In a step 560, method 550 fits an ellipsoid to tumor 175. In one example of step 560, position calculator 324 fits an ellipsoid 502 to tumor 210.

A step 570 determines the direction of the major axis of the ellipsoid of step 560 to define line L1 as the line having same direction as the major axis. The major axis of the ellipsoid is the axis associated with the longest semi-axis of the ellipsoid. In one example of step 570, direction calculator 326 determines the direction of the major axis of ellipsoid 502 to define line 504.

A step 572 determines the optimal incision site as the point located at the intersection of line L1 and surface 174. In one example of step 572, position calculator 324 determines point 222 located at the intersection of line 504 with surface 220, and incision site calculator 332 defines the optimal incision point as point 222.

A step 574 determines the projection of tumor 175 onto surface 174 as the projection of the silhouette of tumor 175 onto surface 174 along line L1. In one example of step 574, tumor perimeter calculator 328 determines the perimeter of tumor 210, and projection calculator 334 project this perimeter onto surface 220 along line 504. Steps 578, 580 and 582 are similar to steps 536, 540, and 542, respectively, except for being based upon line L1 co-directional with the major axis of ellipsoid 502 (as opposed to line L1 defined by vector V1).

Figure 6:
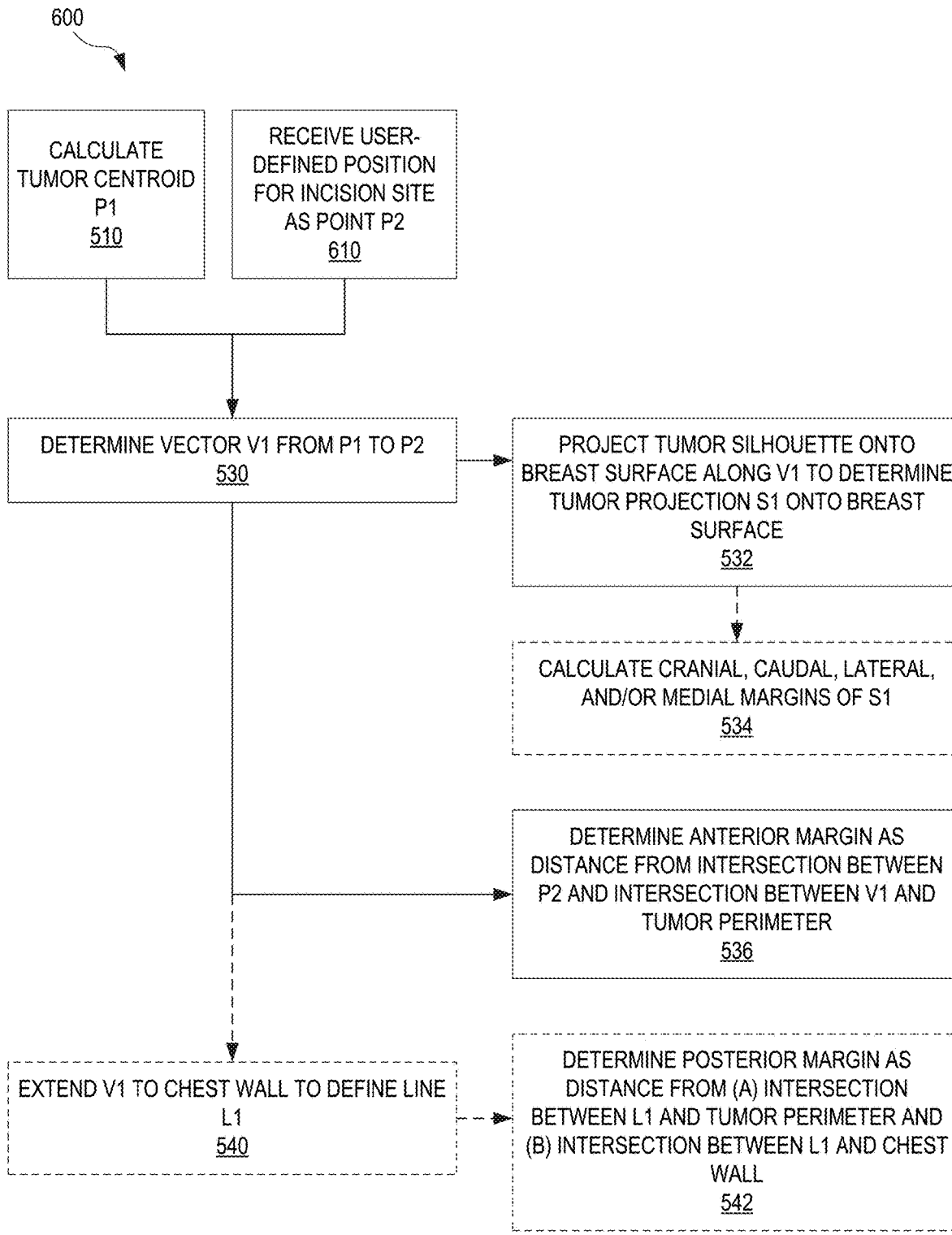
FIG. 6 illustrates a method for generating surgical guidance cues from at least one supine image and a user-defined incision site for tumor resection of tumor, according to an embodiment.

FIG. 6 illustrates one exemplary method 600 for generating surgical guidance cues 138 from at least one supine image 158 and a user-defined incision site for resection of tumor 175. Method 600 is performed by location module 120 and surgical cue generator 130, for example. Method 600 enables system 100 to generate surgical guidance cues 138 while taking into account a user-defined incision site. Method 600 is an embodiment of step 420 of method 400.

Method 600 includes step 510 of calculating centroid P1 of tumor 175. Method 600 also includes a step 610 of receiving, as point P2, the position of a user-defined incision site for performing the resection surgery. In one example of step 610, interface 360 receives the position of a user-defined incision site. Next, method 600 proceeds to perform steps 530, 532, 536, and optionally one or more of steps 534, 540, and 542, as discussed in reference to FIG. 5A except with P2 being the position of the user-defined incision site.

Without departing from the scope hereof, each of methods 500, 550, and 600 may be extended to a more general embodiment of guiding resection of local tissue from patient 170. Each of methods 500, 550, and 560 may, for example, be extended to guide tumor resection from other body parts and organs, such as the brain or the liver, as well as guide biopsy procedures of, e.g., breast 172, muscle, or bone, or extended to guide local delivery of markers or a therapeutic agent to patient 170. As such, each of tumors 175 and 210 may be generalized to local tissue of patient 170, each of breasts 172 and 202 may be generalized to a portion of patient 170 associated with the tissue resection procedure, each of surfaces 174 and 220 may be generalized to be a surface of patient 170 near the local tissue and including the incision site for removing the local tissue, and chest wall 240 may be generalized to be another tissue type or organ underlying the local tissue when viewed from the surface.

Figure 7:
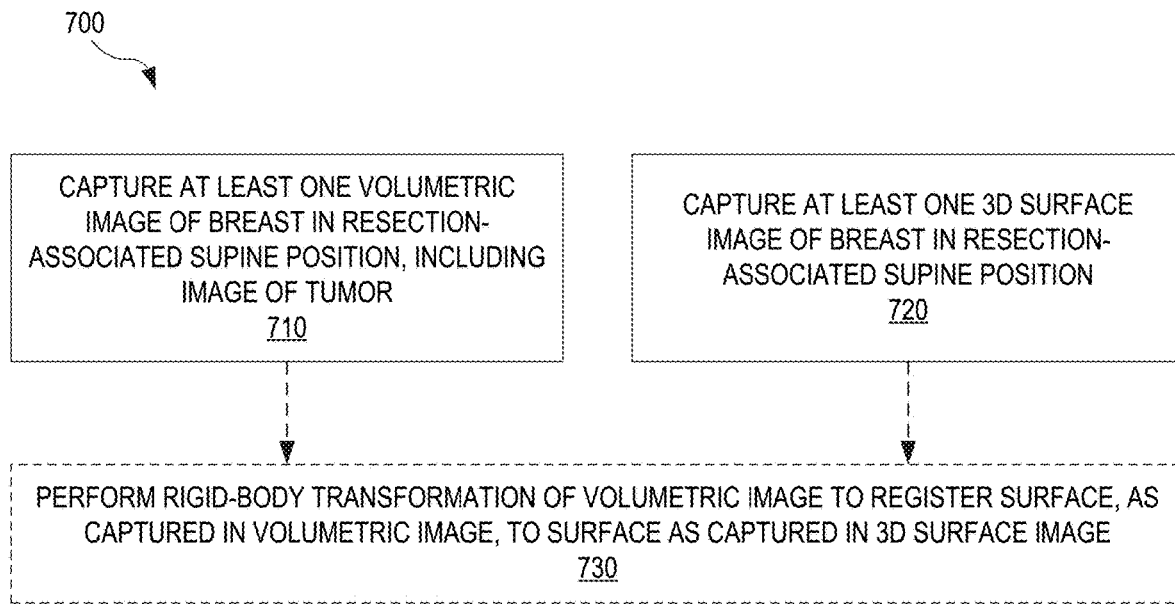
FIG. 7 illustrates a method for generating supine images, wherein those supine images include separate volumetric and surface images, according to an embodiment.

FIG. 7 illustrates one exemplary method 700 for generating supine images 158, wherein supine images 158 include separate volumetric and 3D surface images. Method 700 is an embodiment of step 410 of method 400. Method 700 is performed by imaging module 150 and image registration module 350, for example.

In a step 710, method 700 captures at least one volumetric image 358 of breast 172, including tumor 175 and with breast 172 in the supine position associated with the resection surgery. Step 710 is performed by volumetric imager 152, for example.

In a step 720, method 700 captures at least one 3D surface image 358 of breast 172, including tumor 175 and with breast 172 in the supine position associated with the resection surgery. Step 720 is performed by surface imager 154, for example.

In one embodiment, method 700 further includes a step 730 of performing a rigid-body transformation of (a) the volumetric image 358 captured in step 710 to register surface 174 as captured in the volumetric image, with (b) surface 174 as captured in the 3D surface image 358 of step 720, so as to register volumetric image 358 with 3D surface image 358. Step 730 is performed by image registration module 350, for example.

In another embodiment, volumetric image 358 of step 710 and 3D surface image 358 of step 720 are inherently registered and method 700 does not include step 730. Instead, method 700 outputs volumetric image 358 of step 710 and 3D surface image 358 of step 720 as supine images 158. In one example, volumetric imager 152 and surface imager 154 capture volumetric image 358 and 3D surface image 358, respectively, in absolute coordinates, and thus ensure inherent registration of the volumetric image and the 3D surface image.

Without departing from the scope hereof, method 700 may replace steps 710 and 720 by a step of receiving volumetric image 358 of step 710 and 3D surface image 358 of step 720 from one or more third party imaging systems.

Figure 8:
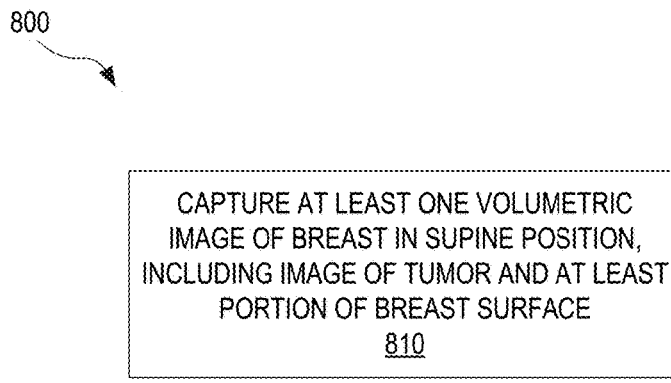
FIG. 8 illustrates a method for generating at least one supine image, wherein each of the at least one supine image is a volumetric image, according to an embodiment.

FIG. 8 illustrates one exemplary method 800 for generating at least one supine image 158, wherein each of the at least one supine image 158 is a volumetric image. Method 800 is performed by volumetric imager 152, for example. Method 800 is an embodiment of step 410.

Method 800 includes a step 810 of capturing at least one volumetric supine image 158 of breast 172 in the supine position associated with the resection surgery to remove tumor 175. The at least one volumetric supine image 158 includes an image of tumor 175 and an image of at least a portion of surface 174. In one example of step 810, a volumetric supine image 158 includes both an image of tumor 175 and an image of at least a portion of surface 174. In another example, step 810 captures a plurality of volumetric supine images 158, wherein at least one volumetric supine image 158 provides an image of tumor 175 and at least one other volumetric supine image 158 provides an image of at least a portion of surface 174.

Figure 9:
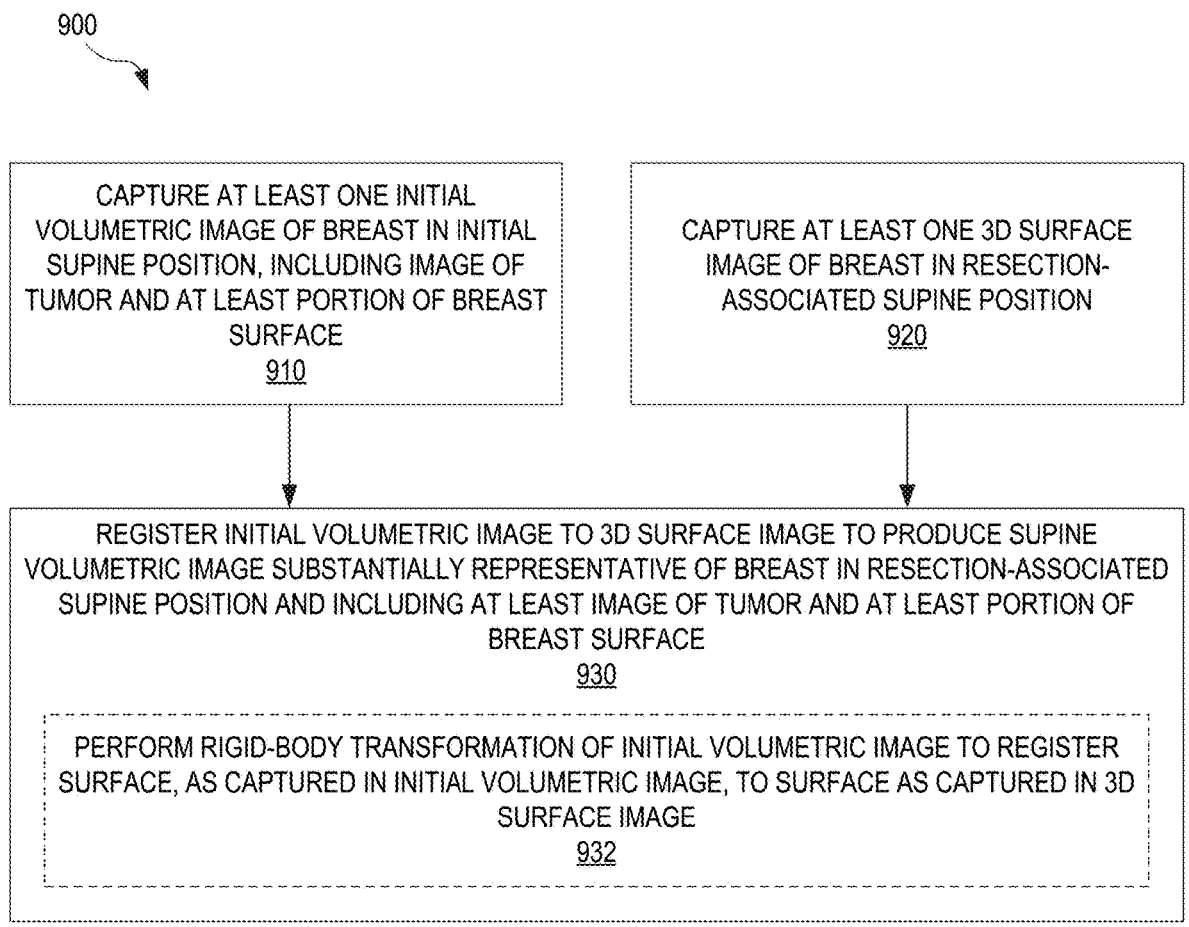
FIG. 9 illustrates a method of generating at least one supine image while accounting for tissue displacement of the breast between pre-operative imaging and resection surgery, according to an embodiment.

FIG. 9 illustrates one exemplary method 900 of generating at least one supine image 158 while accounting for tissue displacement of breast 172 between at least a portion of preoperative imaging and resection surgery. Method 900 is performed by imaging module 150 and image registration module 350, for example. Method 900 is an embodiment of step 410.

In a step 910, method 900 captures at least one initial volumetric image 358 of breast 172 in an initial supine position. This at least one initial volumetric image 358 includes an image of tumor 175 and an image of at least a portion of surface 174, as discussed in reference to FIG. 8. In one example of step 910, volumetric imager 152 captures at least one initial volumetric image 358 of breast 172.

In a step 920, method 900 captures at least one 3D surface image 358 of breast 172 in the supine position associated with resection of tumor 175. In one example of step 920, surface imager 154 captures a 3D surface image 358 of at least a portion of surface 174. In another example of step 920, volumetric imager 152 captures a volumetric image 358 of breast 172, which includes at least a portion of surface 174.

In a step 930, method 900 registers initial volumetric image 358, captured in step 910 to 3D surface image 358 captured in step 920. Step 930 is an embodiment of step 412 and may be performed by image registration module 350. Step 930 may include a step 932 of performing a rigid-body transformation of initial volumetric image 358 to register surface 174, as captured in initial volumetric image 358, to surface 174 as captured in resection-associated 3D surface image 358. Step 932 is an embodiment of step 412 and may utilize fiducials on surface 174 as discussed in reference to FIGS. 4A and 4B. In one example of step 932, image registration module 350 utilizes rigid-body transformation unit 352 as discussed above in reference to FIG. 3.

Without departing from the scope hereof, method 900 may replace steps 910 and 920 by a step of receiving initial volumetric image 358 of step 910 and 3D surface image 358 of step 920 from one or more third party imaging systems.

Without departing from the scope hereof, each of methods 700, 800, and 900 may be extended to a more general embodiment of guiding resection of local tissue from patient 170. Each of methods 700, 800, and 900 may be extended to guide tumor resection from other body parts and organs, such as the brain or the liver, as well as guide biopsy procedures of, e.g., breast 172, muscle, or bone, extended to guide local delivery of markers or a therapeutic agent to patient 170. As such, tumor 175 may be generalized to local tissue of patient 170, breast 172 may be generalized to a portion of patient 170 associated with the tissue resection procedure, surface 174 may be generalized to a surface of patient 170 near the local tissue and including the incision site for removing the local tissue, and supine image 158 may be generalized to an image of the portion of patient 170 associated with the tissue resection procedure positioned as during the tissue resection procedure. Each of methods 700, 800, and 900 may further be used to guide local delivery of markers or a therapeutic agent to patient 170

Figure 10A:
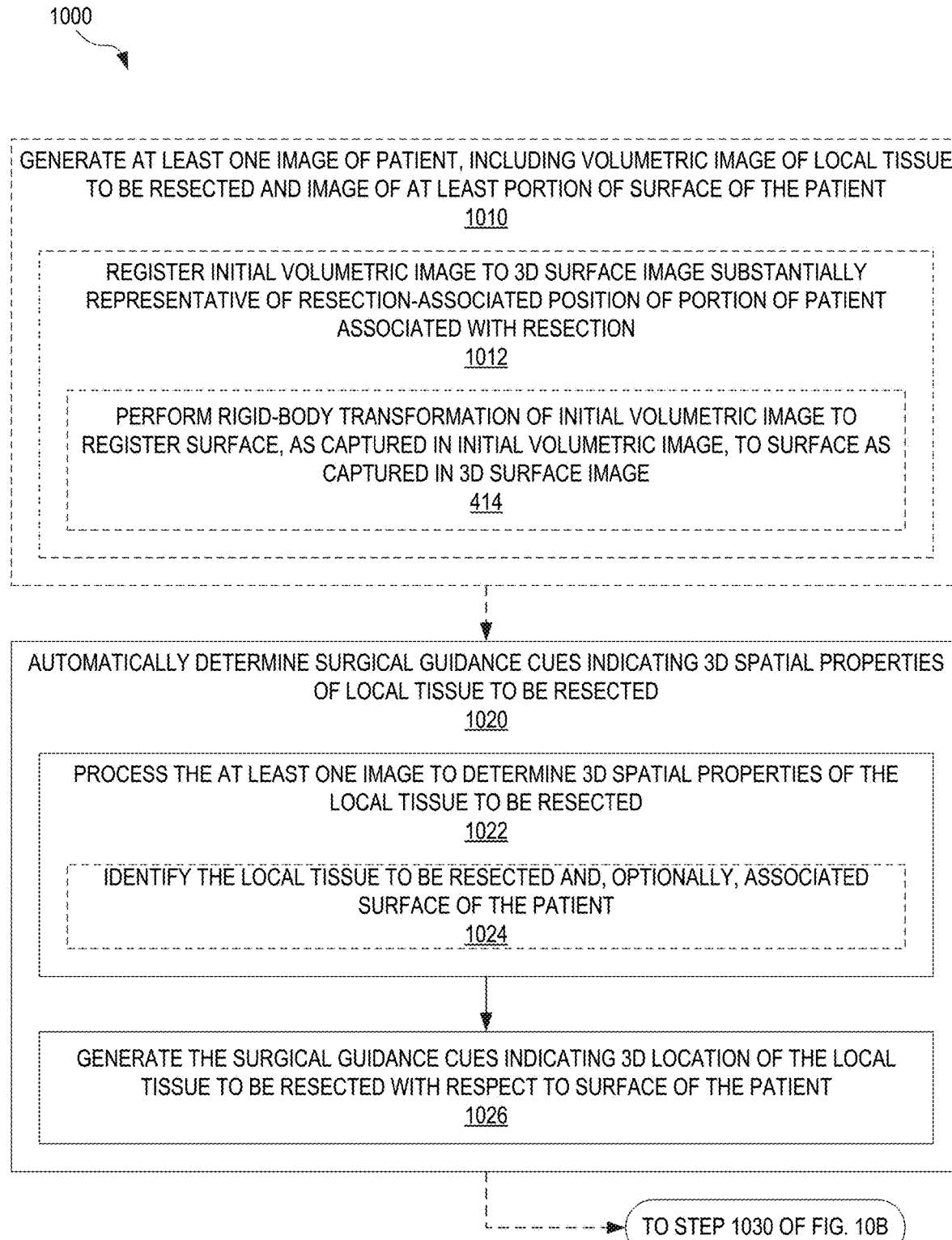
FIGS. 10A and 10B illustrate a method for guiding resection of local tissue from a patient, according to an embodiment.
Figure 10B:
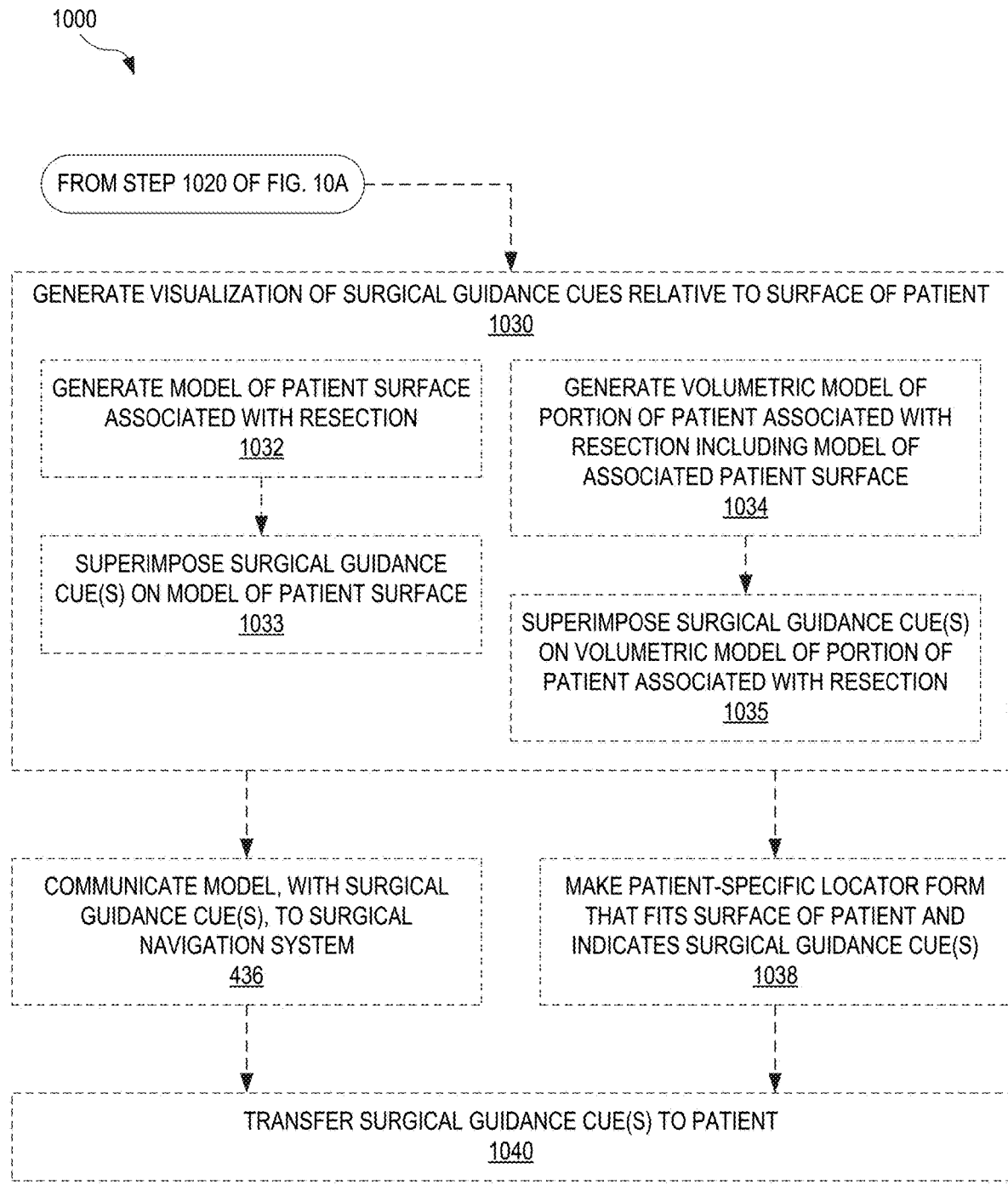

FIGS. 10A and 10B illustrate one exemplary method 1000 for guiding resection of local tissue from patient 170. Method 1000, or a portion thereof, may be performed by system 100. FIG. 10A shows a first portion of method 1000 and FIG. 10B shows a second optional portion of method 1000. FIGS. 10A and 10B are best viewed together. Method 1000 is an extension of method 400 to general resection of local tissue from patient 170.

In one embodiment, method 1000 includes a step 1010 of generating at least one image 158 of a portion of patient 170 that is associated with the tissue resection procedure. This resection-associated portion of patient 170 includes (a) the local tissue to be resected and (b) a surface of patient 170 near the local tissue and including the incision site for the tissue resection procedure. Step 1010 is a generalization of step 410. Image 158 generated by step 1010 is representative of the resection-associated portion of patient 170 substantially as positioned during the tissue resection procedure. In this more general embodiment, image 158 need not be a supine image. In one example of step 1010, imaging module 150 directly captures one or more images 158 or images 358 of the resection-associated portion of patient 170. In another example, system 100 receives images 358 from a third party system. In certain embodiments, step 1010 includes a step 1012 of registering an initial volumetric image 358 of the local tissue to a 3D surface image 358 of the associated surface of patient 170, wherein 3D surface image 358 is substantially representative of the resection-associated portion of patient 170 as positioned during the tissue resection procedure. In one example of step 1012, image registration module 350 registers an initial volumetric image 358 to 3D surface image 358, as discussed above in reference to FIG. 3. Step 1012 may include step 414 as discussed above in reference to FIGS. 4A and 4B but extended to general resection of local tissue from patient 170.

In another embodiment, method 1000 does not include step 1010 but instead receives image(s) 158 as generated by a third party system.

In a step 1020, method 1000 automatically determines surgical guidance cues 138 indicating 3D spatial properties of the local tissue to be resected. Step 1020 includes steps 1022 and 1026, and optionally a step 1024. Steps 1020, 1022, 1024, and 1026 are extensions of respective steps 420, 424, 424, and 426 to general resection of local tissue from patient 170.

Step 1022 processes at least one image 158 to determine 3D spatial properties 128 for the local tissue. Step 1022 may include step 1024. Step 1024 identifies the local tissue to be resected and, optionally, identifies the associated surface of patient 170. Step 1026 utilizes 3D spatial properties 128 to generate surgical guidance cues 138 for the local tissue with respect to the associated surface of patient 170. Steps 1020, 1022, 1024, and 1026 are performed in a manner similar to that discussed above in reference to FIGS. 4A and 4B for steps 420, 424, 424, and 426.

In certain embodiments, method 1000 includes a step 1030 of visualizing surgical guidance cues 138 relative to the associated surface of patient 170. Step 1030 is an extension of step 430 to general resection of tissue from patient 170. In one implementation, step 1030 includes steps 1032 and 1033. Step 1032 generates a model 348 of the surface of patient 170 associated with the tissue resection procedure, such as a 3D surface map of this surface, and step 1033 superimposes one or more surgical guidance cues 138 on this model 348. Steps 1032 and 1033 are performed in a manner similar to that of steps 432 and 433. In another implementation, step 1030 includes steps 1034 and 1035. Step 1034 generates a volumetric model 348 of the resection-associated portion of patient 170 including a model of at least a portion of the resection-associated surface, such as a volumetric map of the resection-associated portion of patient 170 including a map of at least a portion of the resection-associated surface, and step 1035 superimposes one or more surgical guidance cues 138 on this volumetric model 348. Steps 1032 and 1033 are performed in a manner similar to that of steps 432 and 433.

Optionally, method 1000 includes step 436 as discussed above in reference to FIGS. 4A and 4B.

Method 1000 may include a step 1038 of producing a patient-specific locator form that fits the resection-associated surface of patient 170 and includes features that indicate one or more of surgical guidance cues 138 and/or enable transfer of surgical guidance cues 138 to patient 170. Such a patient-specific locator form is discussed further in reference to FIGS. 20-27. Step 1038 is an extension of step 438 to general resection of local tissue from patient 170.

Method 1000 may further include a step 1040 of transferring one or more surgical guidance cues 138 to the resection-associated surface of patient 170. Step 1040 is performed in a manner similar to that of step 440.

Figure 11:
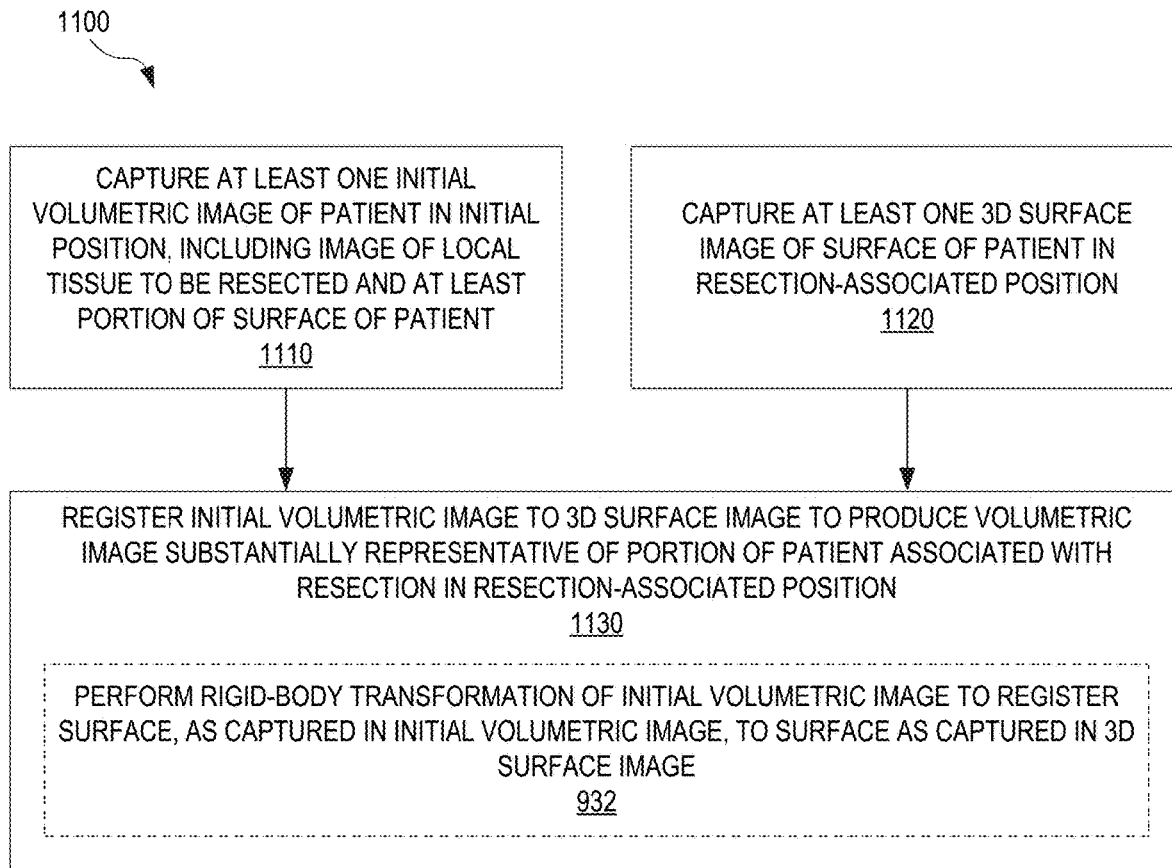
FIG. 11 illustrates a method for generating at least one image associated with a tissue resection procedure, while accounting for tissue displacement between at least a portion of pre-operative imaging and the resection procedure, according to an embodiment.

FIG. 11 illustrates one exemplary method 1100 for generating at least one image 158 of a portion of patient 170 including local tissue to be resected, while accounting for tissue displacement between at least a portion of preoperative imaging and the resection procedure. Method 1100 is performed by imaging module 150 and image registration module 350, for example. Method 1100 is an embodiment of step 1010 and is an extension of method 900 to general resection of local tissue from patient 170.

In a step 1110, method 1000 captures at least one initial volumetric image 358 of the local tissue in an initial position. This at least one initial volumetric image 358 includes an image of the local tissue to be resected and an image of at least a portion of a surface of patient 170 associated with the resection procedure, as discussed in reference to FIGS. 10A and 10B. In one example of step 1110, volumetric imager 152 captures at least one initial volumetric image 358 of a portion of patient 170 associated with the resection procedure.

In a step 1120, method 1100 captures at least one 3D surface image 358 of the resection-associated surface of patient 170 as positioned during the resection procedure. Step 1120 may be performed in a manner similar to that of step 920.

In a step 1130, method 1100 registers the initial volumetric image 358, captured in step 1110, to the 3D surface image 358 captured in step 1120. Step 1130 is an extension of step 930 and may be performed by image registration module 350. Step 1130 may include step 932.

Figure 12:
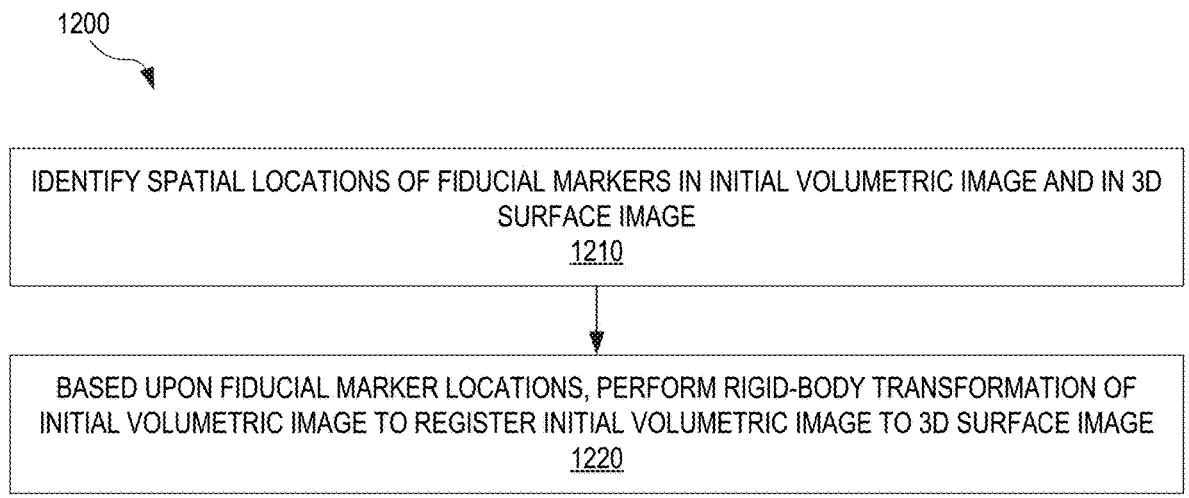
FIG. 12 illustrates a method for using a rigid-body transformation to register an initial volumetric image of a patient to a 3D surface image of the patient substantially as positioned during resection surgery, according to an embodiment.

FIG. 12 illustrates one exemplary method 1200 for using a rigid-body transformation to register (a) an initial volumetric image 358 of a portion of patient 170 associated with resection surgery to (b) a 3D surface image 358 of the portion of patient 170 associated with resection surgery substantially as positioned during resection surgery. Method 1200 is an embodiment of step 932 and of step 414, and may be implemented by rigid-body transformation unit 352 and feature locator 356 in cooperation.

In a step 1210, method 1200 identifies the spatial locations of fiducials on patient 170 in initial volumetric image 358 and in 3D surface image 358. The fiducials may be fiducial markers placed on the surface of patient 170 and/or natural features of patient 170. In one example of step 1210, feature locator 356 identifies fiducials on surface 174 in initial volumetric image 358 and identifies the same fiducials in 3D surface image 358. Depending on the tissue displacement between initial volumetric image 358 and in 3D surface image 358, the fiducials may be in relatively similar positions, for example as between a supine initial volumetric image 358 of breast 172 and a supine 3D surface image 358 of breast 172, or be relatively disparate, as between a prone initial volumetric image 358 of breast 172 and a supine 3D surface image 358 of breast 172.

In a step 1220, method 1200 performs a rigid-body transformation of initial volumetric image 358 to register fiducials identified in initial volumetric image 358 with the corresponding fiducials identified in 3D surface image 358, by matching the fiducials identified in the coordinate system of initial volumetric image 358 with the corresponding fiducials identified in the coordinate system of 3D surface image 358. Step 1220 thus produces a registered volumetric image that is registered to 3D surface image 358. This registered volumetric image is an example of supine image 158. This rigid-body transformation may include translation, rotation, and/or scaling, but generally does not require shearing. In one example of step 1220, rigid-body transformation unit 352, according to fiducial locations identified by feature locator 356 in step 1210, applies a rigid-body transformation to initial volumetric image 358 to register fiducials identified in initial volumetric image 358 with the corresponding fiducials identified in 3D surface image 358.

Figure 13:
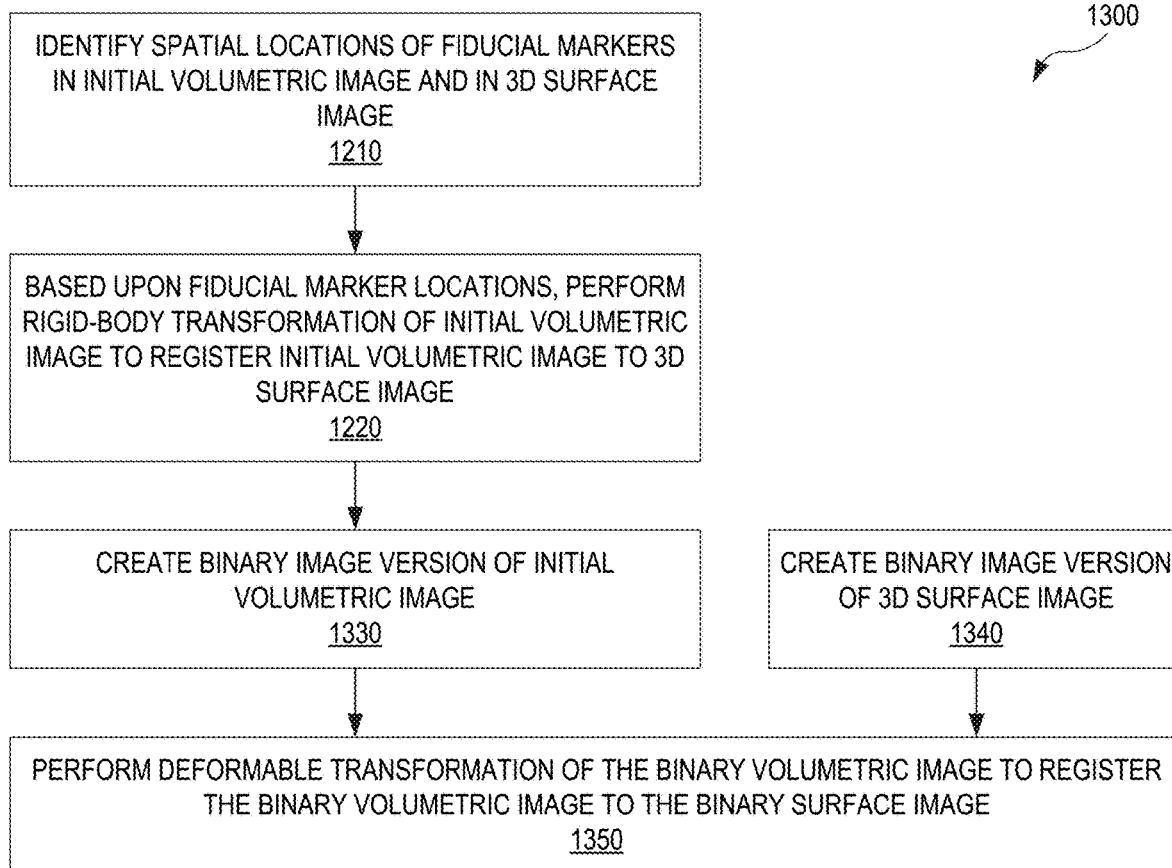
FIG. 13 illustrates a method for using a rigid-body transformation to register an initial volumetric image of a patient to a 3D surface image of the patient substantially as positioned during resection surgery, and further using binary image generation and deformable transformation thereof to emphasize certain features, according to an embodiment.

FIG. 13 illustrates one exemplary method 1300 for using a rigid-body transformation to register an initial volumetric image 358 of patient 170 to a 3D surface image 358 of patient 170 reflecting the positioning used during the resection procedure, and further using binary image generation and deformable transformation thereof to emphasize certain features. Method 1300 is an embodiment of step 414, and may be implemented by deformable transformation unit 354 and feature locator 356 in cooperation. Method 1300 may be particularly useful when the tissue displacement between initial volumetric image 358 and 3D surface image 358 is significant, for example as generally is the case for a prone volumetric image 358 of breast 172 and a corresponding supine 3D surface image 358 of surface 174. Generally, method 1300 may be useful in scenarios where there is tissue displacement between initial volumetric image 358 of a portion of patient 170 and a corresponding 3D surface image 358 of a surface of patient 170, or in scenarios where a difference between the imaging modalities used to capture initial volumetric image 358 and 3D surface image 358 results in an apparent tissue displacement.

Method 1300 includes steps 1210 and 1220 as discussed above in reference to FIG. 12.

In a subsequent step 1330, method 1300 creates a binary image version of the registered volumetric image generated in step 1320. In one example of step 1330, binary image generator 357 processes the registered volumetric image to create a binary version thereof. Step 1330 may be implemented by binary image generator 357.

In a step 1340, method 1300 creates a binary image version of 3D surface image 358. In one example of step 1340, binary image generator 357 processes 3D surface image 358 to create a binary version thereof. Step 1340 may be implemented by binary image generator 357.

Both 3D surface image 358 and initial volumetric image 358 may be grayscale images, where each pixel (for 3D surface image 358) or voxel (for initial volumetric image 358) is represented as a gray color in a range between darkest (black) or lightest (white). Alternatively, one or both of 3D surface image 358 and initial volumetric image 358 is a color image that also provides intensity information. In contrast, a binary image represents each pixel or voxel as either black or white, without any shades of gray in between. Therefore, creating a binary image from a grayscale image is a technique for emphasizing certain desired features in an image, and removing other features from the image.

In one example, step 1330 generates a binary version of the registered volumetric image, which emphasizes surface features in the registered volumetric image, such as features of surface 174 of breast 172. For example, step 1330 may create the binary version of the registered volumetric image from the registered volumetric image by setting the intensity values of the voxels that are sufficiently close to the surface to unity and zero otherwise. A typical range for voxels defined as being sufficiently close to the surface may be, but is not limited to, voxels within 10 mm of the tissue-to-air interface.

Steps 1330 and 1340 may serve to emphasize features common to both the registered volumetric image and 3D surface image 358 in order to perform a deformable transformation of the binary version of the registered volumetric image to the binary version of 3D surface image 358. Both of these binary images highlight the same tissue-to-air interface, which allows for non-rigid registration of the two binary images to be deformably registered using the rigid registration of step 1320 as a starting point.

In a step 1350, method 1300 deformably transforms the binary version of the registered volumetric image to register the binary version of the registered volumetric image to the binary version of 3D surface image 358. Step 1350 may be performed by deformable transformation unit 354.

In one example, step 1350 first performs an affine registration of the binary version of the registered volumetric image to the binary version of 3D surface image 358 to produce an intermediate binary image. Next, in this example, step 1350 applies a deformable transformation to the intermediate binary image to register the intermediate binary image to the binary version of 3D surface image 358. This deformable transformation is subject to the constraint of matching fiducials in the intermediate binary image to those in the binary version of 3D surface image 358. The deformable transformation may be, but is not limited to, a B-Spline deformable registration, or another deformable transformation or registration known in the art.

Figure 14:
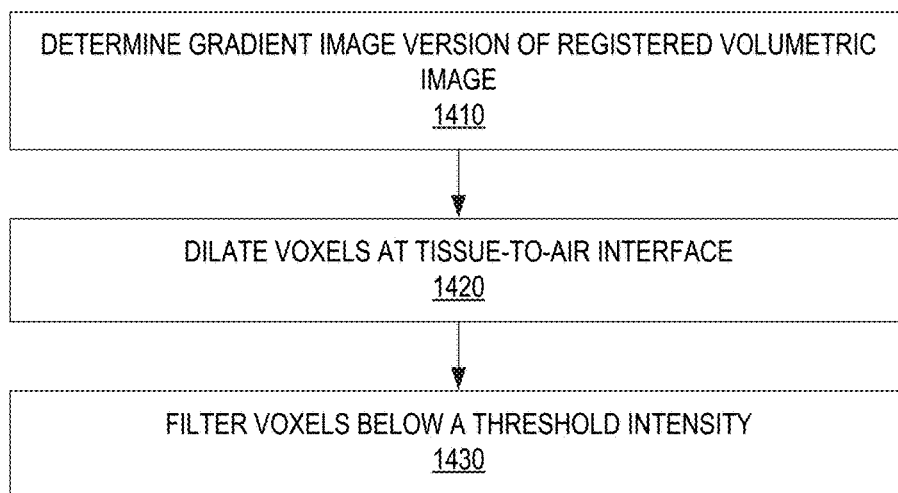
FIG. 14 illustrates a method for generating a binary version of a registered volumetric image of the method of FIG. 13, according to an embodiment.

FIG. 14 illustrates one exemplary method 1400 for generating a binary version of the registered volumetric image of step 1320 of method 1300. Method 1400 is an embodiment of step 1330. Method 1400 is performed by binary image generator 357, for example.

A step 1410 determines a gradient image version of the registered volumetric image of step 1220 as implemented in method 1300. This gradient image indicates directional change in the intensity or color of the registered volumetric image and may be used to identify certain features in the registered volumetric image. The gradient image may identify one or more anatomical boundaries, for example a tissue-to-air interface such as surface 174.

A step 1420 dilates voxels at the tissue-to-air interface. Step 1420 may utilize a similar range of voxels as discussed above for step 1330 in reference to FIG. 13.

A step 1430 filters out voxels, of the image generated in step 1420, that are below a threshold intensity. While in general, the threshold intensity level may be chosen to be any intensity, for example to provide a more granular grayscale image, for a binary image the threshold may be set to maximum intensity, so that any pixels or voxels that were not set to maximum intensity during dilation are filtered out.

Additional pre-registration processing, such as rasterization, Gaussian smoothing, and morphology operations, is possible in order to further improve the robustness of image registration such as the rigid-body registration performed in step 1220. In one example, the dilated volumetric gradient image generated in step 1420 as well as 3D surface image 358 may be Gaussian-smoothed (for example, with a kernel of 5×5×5 voxels) to reduce the noise level. Registration of the dilated volumetric gradient image to 3D surface image 358 may be performed. For example, the dilated volumetric gradient image may be registered to a rasterized version of 3D surface image 358. Registration may be based on maximization of mutual information between the two image volumes.

Without departing from the scope hereof, each of methods 1200, 1300, and 1400 may utilize additional processing or filtering of images 358 to optimize registration for specific types of images 358. The goal of such parameter optimization may be to emphasize features in initial volumetric image 358 to match similar features that are inherently emphasized in a corresponding 3D surface image 358 representative of the resection-associated portion of patient 170 being in substantially the position used during the resection procedure. These parameter manipulations may be based on a predetermined set of parameters depending upon the type of 3D surface image 358 or, alternatively, may be optimized based on conditions particular to a 3D surface image 358.

Figure 15:
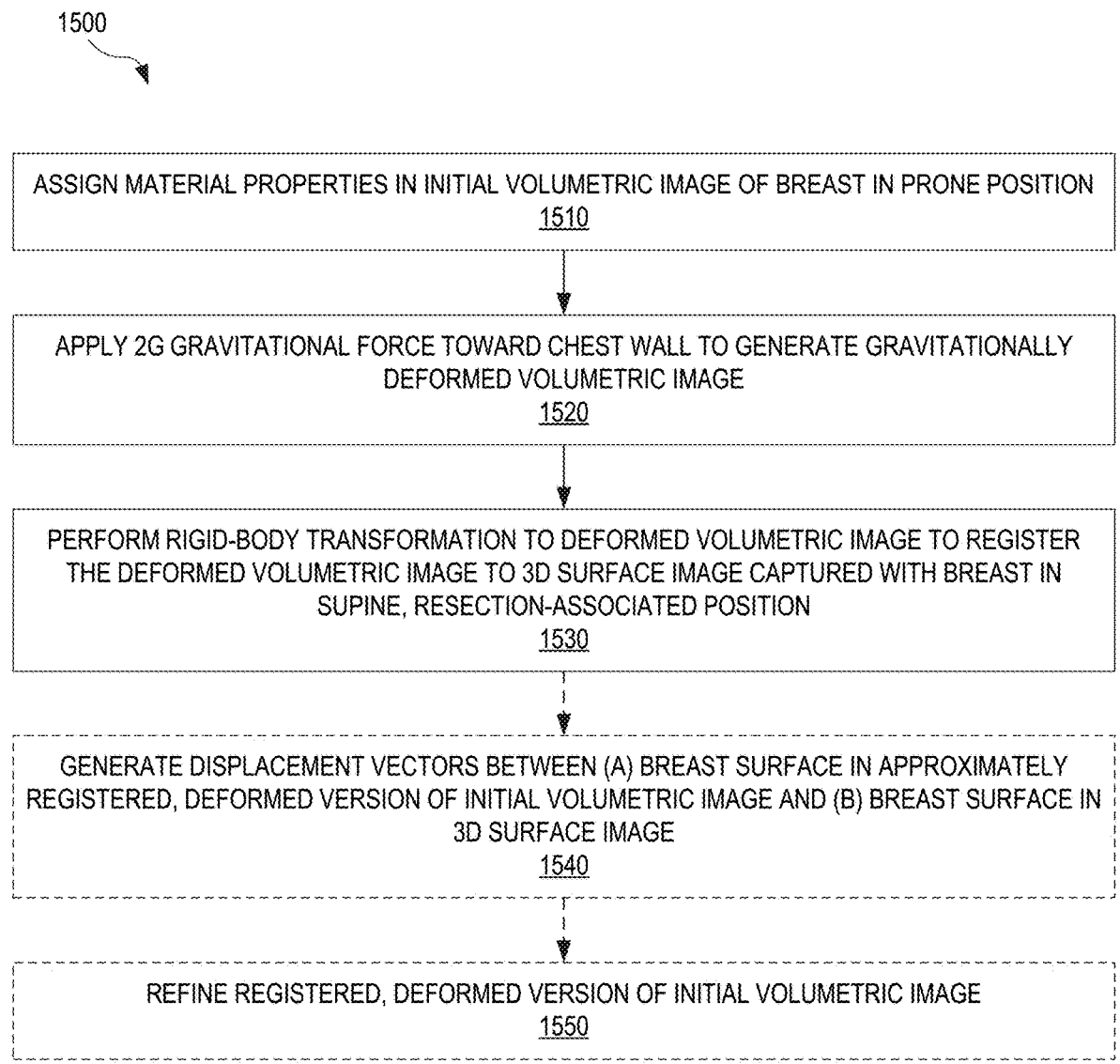
FIG. 15 illustrates a finite element modeling method for deformably registering a prone volumetric image of a breast to a resection-associated supine 3D surface image of the breast, according to an embodiment.

FIG. 15 illustrates one exemplary finite element modeling (FEM) method 1500 for deformably registering a prone volumetric image 358 of breast 172 to a resection-associated supine 3D surface image 358 of surface 174. FEM method 1500 is an embodiment of step 414, and may be cooperatively implemented by feature locator 356 and an embodiment of deformable transformation unit 354 that includes gravity unit 355. Generally, FEM method 1500 may be useful in scenarios where tissue displacement between prone volumetric image 358 and supine 3D surface image 358 is such that a rigid-body transformation is inadequate. FIGS. 16A-C and 17A-C discussed below show exemplary tissue displacements for breast 172 between prone and supine positions.

FEM method 1500 takes into account the physical properties of the tissue in the images. By modeling the physical properties of the tissue, FEM method 1500 may more accurately register prone volumetric image 358 to supine 3D surface image 358.

FEM method 1500 leverages information about the tissue in the volumetric and surface images to more accurately model the transformation. For example, tissue of breast 172 may exhibit different elastic properties in a first region of breast 172 than the elastic properties of a second region of breast 172. For example, regions of breast 172 corresponding to gland tissue may be assigned a first elastic modulus, and regions of breast 172 where invasive ductal carcinoma is detected may be assigned a second elastic modulus, where the second elastic modulus is greater than the first elastic modulus. Examples of other tissues with known elastic modulus, include, but are not limited to, normal fat tissue, normal gland tissue, fibrous tissue, invasive ductal carcinoma, and ductal carcinoma in situ (DCIS). Whereas a rigid transformation may produce errors by not taking the different elastic properties of different regions of tissue into account, FEM method 1500 may produce more accurate results based on more accurate modeling of the properties of different regions of tissue.

In a step 1510, FEM method 1500 assigns material properties to identified tissue in the volumetric scan. For example, chest wall 240 may be treated as being relatively inelastic, and may therefore only deform minimally between prone and the supine positions. In contrast, gland and fat tissue may have higher elasticity properties, while muscle or some types of cancerous tissue may have lower elasticity properties. By identifying types of tissue and assigning different material properties and properties to the different types of tissue based upon the identified tissue type, FEM method 1500 may more accurately model the deformation between the prone and supine positions.

In a step 1520, FEM method 1500 deforms prone volumetric image 358 with a finite-element model by applying a computational model to prone volumetric image 358. This computational model applies a simulated gravitational force of 2G to breast 172 in the direction of chest wall 240. This deformation attempts to normalize prone volumetric image 358 with supine 3D surface image 358, since supine 3D surface image 358 is performed while breast 172 is subject to a gravitational force of 1G in the direction toward chest wall 240 and prone volumetric image 358 is taken when breast 172 is subject to a gravitational force of 1G in the direction away from chest wall 240. Step 1520 may be implemented by gravity unit 355.

In a step 1530, FEM method 1500 performs a rigid-body transformation of the deformed volumetric image generated in step 1520 to register the deformed volumetric image to supine 3D surface image 358. Step 1530 thus generates a registered volumetric image that is registered to supine 3D surface image 358. This registered volumetric image is an example of supine image 158.

An optional step 1540 generates displacement vectors, for example between surface 174 as shown in the registered volumetric image and surface as shown in 3D surface image 358.

An optional step 1550 refines the registered volumetric image generated in step 1530. In one embodiment, step 1550 performs a second deformation simulation. In another embodiment, the displacement vectors of step 1540 are generated by matching the set of fiducial locations and step 1550 deformably transforms the shape of breast 172 in an inverse modeling approach to avoid overfitting the shape that can be adversely affected by measurement error.

In an alternative embodiment, FEM method 1500 is used to register a supine volumetric image 358 to a supine 3D surface image 358. In accordance with this alternative embodiment, the flowchart of FIG. 15 would be slightly modified, with step 1520 reading "apply a 2G gravitational force adjustment toward chest wall".

Without departing from the scope hereof, FEM method 1500 may be extended from registration of images of breast 172 to registration of images of other portions of patient 170 associated with a different tissue resection procedure by using different mathematical models for the tissue in the images. For example, while a simple linear elastic model may be used to model tissue of breast 172, additional models used by a more generally applicable embodiment of FEM method 1500 may include, but are not limited to, linear elastic, neohookean, exponential, and other non-linear approaches.

In each of methods 1200, 1300, 1400, and 1500, surface 174 (or another surface of patient 170 associated with a tissue resection procedure) may be modeled by mapping the surface as a mesh of elements. The elements may be represented by polygons, for example, triangles. Deformation calculations, as used in FEM method 1500, may be simplified by calculating displacement vectors for specific points, or nodes, on the mapping mesh, rather than calculating displacement vectors for every point on the surface. The nodes may be, for example, the corners of each triangle in the mapping mesh. Once the location of the nodes is calculated after deformation, the intermediate points may be approximated, for example, by linear interpolation. Similarly, mapping meshes may be used to correlate surface locations in the volumetric image to locations on the 3D surface image. One exemplary approach is to map points on the surface of the volumetric image to the closest node locations (after rigid-body transformation) on the 3D surface image. The 3D surface image mesh may typically have much higher density, so interpolation between nodes is not needed. An alternative approach is to find the closest point on each element of the 3D surface image, as opposed to the closest node.

FIGS. 16A-C and 17A-C illustrate exemplary tissue displacement for breast 172 between prone and supine positions for three patients 170. FIGS. 16A, 16B, and 16C show breasts 172(1), 172(2), and 172(3) of three respective patients 170 in prone position. The perspective in FIGS. 16A-C is from above the head of each patient 170. FIGS. 17A, 17B, and 17C show breasts 172(1), 172(2), and 172(3) when patients 170 are in supine position. The perspective in FIGS. 17A-C is from above each patient 170. Each of FIGS. 16A-C and 17A-C indicate chest wall outline 240, surface 220, tumor 175 (or alternatively other local tissue of interest), a nipple 1610, and an imaginary center axis 1620 is shown, indicating a midpoint of the breasts 172(1), 172(2), and 172(3) relative to chest wall 240. FIGS. 16A-C and 17A-C are best viewed together.

Breast 172(1) in supine position demonstrates both vertical compression and horizontal displacement, with both nipple 1610 and tumor 175 distorted in relation to center axis 1620 in comparison breast 172(1) in prone position. Breast 172(2) shows both vertical compression and horizontal displacement from prone position to supine position, with both nipple 1610 and the tumor 175 having been distorted in relation to the center axis 1620. However, the relational positions of the elements of breast 172(2) are different from those of breast 172(1). Such variations may be due to the amount of breast tissue, the relative density of the breast tissue, and/or the amount of surface area. In contrast, while breast 172(3) demonstrates some vertical compression, breast 172(3) demonstrates significantly less horizontal displacement.

Figure 18A:
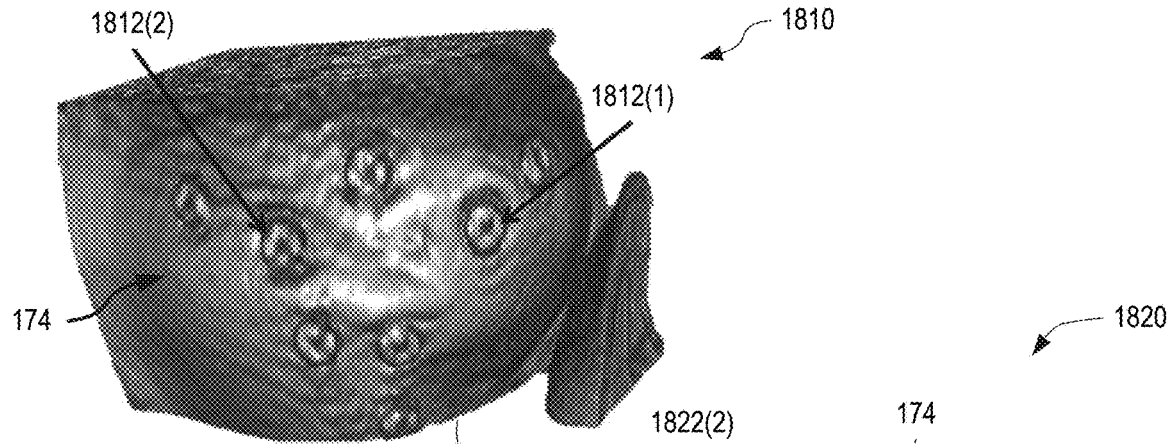
FIGS. 18A-D show an example of rigid-body transformation of a volumetric image of a breast, captured with the breast in an initial supine position, to register the volumetric image to a 3D surface image captured with the breast in the supine position used during resection surgery, according to an embodiment.
Figure 18B:
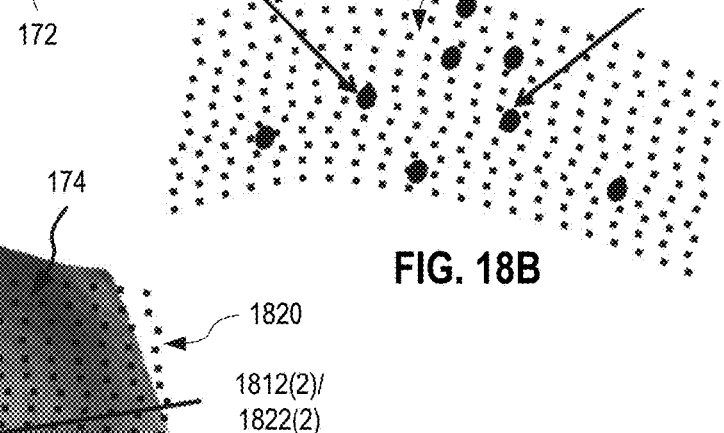
Figure 18C:
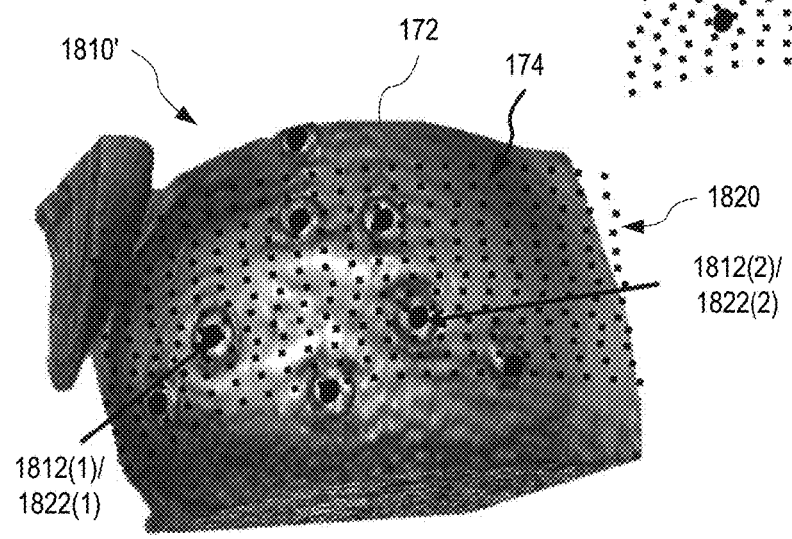
Figure 18D:
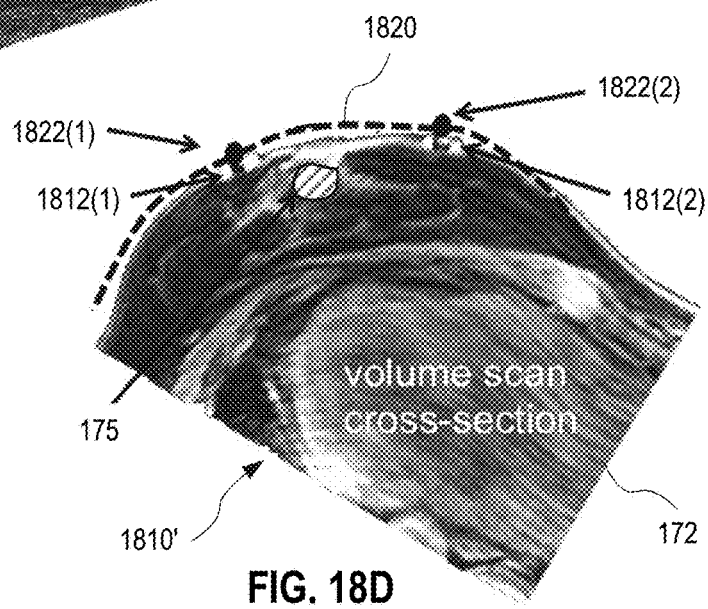

FIGS. 18A-D show one example of rigid-body transformation of a volumetric image 1810 of breast 172, captured with breast 172 in an initial supine position, to register volumetric image 1810 to a 3D surface image 1820 captured with breast 172 in the supine position used during resection of tumor 175. The rigid-body transformation shown in FIGS. 18A-D is performed according to method 1200. Volumetric image 1810 is an example of volumetric image 358. 3D surface image 1820 is an example of 3D surface image 358. FIG. 18A shows surface 174 as captured in volumetric image 1810. FIG. 18B shows 3D surface image 1820. FIG. 18C shows surface 174 of volumetric image 1810 after registration of volumetric image 1810 to optical image 1820. FIG. 18D shows a cross-section of volumetric image 1810, including tumor 175, after registration of volumetric image 1810 to optical image 1820. FIGS. 18A-D are best viewed together.

As illustrated in FIGS. 18A and 18B, step 1210 of method 1200 identifies (a) fiducial marker locations 1812 on surface 174 in volumetric image 1810 and (b) fiducial marker locations 1822 on surface 174 in 3D surface image 1820. As illustrated in FIGS. 18C and 18D, step 1220 of method 1200 performs a rigid-body transformation of volumetric image 1810 to match fiducial marker locations 1812 to fiducial marker locations 1822. This results in registration of surface 174, as captured in volumetric image 1810, to surface 174 as captured in 3D surface image 1820. FIG. 18D shows tumor 175 and the location of tumor 175 in relation to surface 174.

Figure 19:
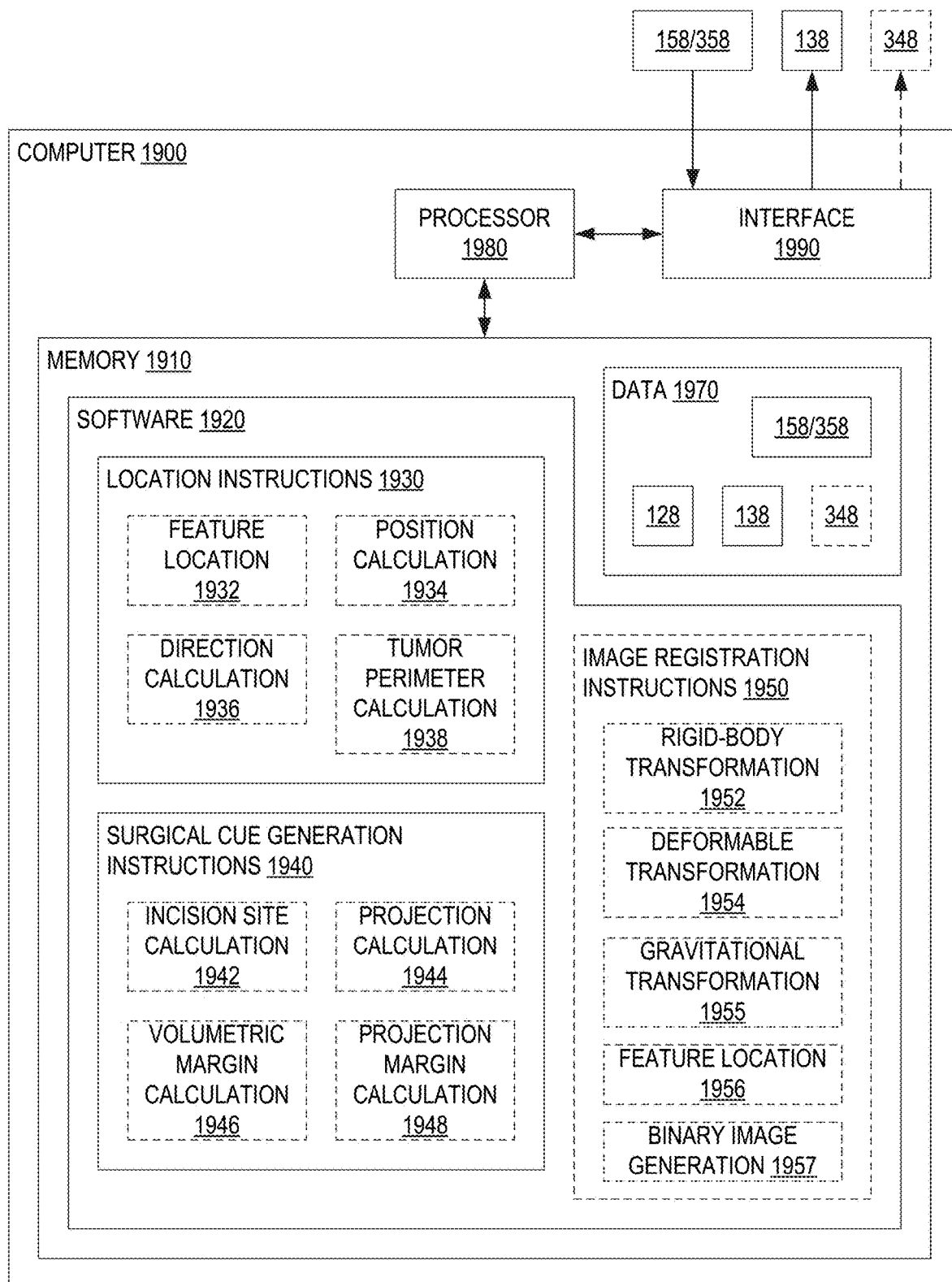
FIG. 19 illustrates a computer that implements a portion of the system of FIG. 3, according to an embodiment.

FIG. 19 illustrates one exemplary computer 1900 that implements location module 120, surgical cue generator 130, and optionally image registration module 350. Computer 1900 may be implemented in system 100. Computer 1900 may perform at least a portion of any of methods 400, 500, 550, 600, 900, 1000, 1100, 1200, 1300, 1400, and 1500.

Computer 1900 includes a non-transitory memory 1910, a processor 1980, and an interface 1990. Processor 1980 is communicatively coupled with memory 1920 and interface 1990. Memory 1910 is, for example, of type ROM, Flash, magnetic tape, magnetic drive, optical drive, RAM, other non-transitory medium, or combinations thereof. Interface 1990 implements (a) an interface between location module 120, or image registration module 350, and imaging module 150 and (b) an interface between surgical cue generator 360 and visualization module 140. Interface 1990 may further implement interface 360. Interface 1990 is for example a wired interface (such as Ethernet, USB, FireWire, or Thunderbolt), a wireless interface (such as IEEE 802.11, Wi-Fi, or Bluetooth), and/or a user interface such as a display, touchscreen, keyboard, and/or pointing device. Memory 1910 includes software 1920 encoded in memory 1910 as machine-readable instructions executable by processor 1980. Memory 1910 further includes a data storage 1970. Software 1920 includes location instructions 1930, surgical cue generation instructions 1940, and optionally image registration instructions 1950.

Processor 1980 may execute (a) location instructions 1930 to implement location module 120 and (b) surgical cue generation instructions 1940 to implement surgical cue generator 130. In embodiments of computer 1900 that include image registration instructions 1950, processor 1980 may execute image registration instructions 1950 to implement image registration module 350.

Location instructions 1930 may include one or more of feature location instructions 1932, position calculation instructions 1934, direction calculation instructions 1936, and tumor perimeter location instructions 1938. Processor 1980 may execute feature location instructions 1932, position calculation instructions 1934, direction calculation instructions 1936, and/or tumor perimeter location instructions 1938 to implement feature locator 322, position calculator 324, direction calculator 326, and/or tumor perimeter calculator 328, respectively.

Surgical cue generation instructions 1940 may include one or more of incision site calculation instructions 1942, projection calculation instructions 1944, volumetric margin calculation instructions 1946, and projection margin calculation instructions 1948. Processor 1980 may execute feature incision site calculation instructions 1942, projection calculation instructions 1944, volumetric margin calculation instructions 1946, and/or projection margin calculation instructions 1948 to implement incision site calculator 332, projection calculator 334, volumetric margin calculator 336, and/or projection margin calculator 338, respectively.

Image registration instructions 1950 may include one or more of rigid-body transformation instructions 1952, deformable transformation instructions 1954, gravitational transformation instructions 1955, feature location instructions 1956, and binary image generation instructions 1957. Processor 1980 may execute rigid-body transformation instructions 1952, deformable transformation instructions 1954, gravitational transformation instructions 1955, feature location instructions 1956, and/or binary image generation instructions 1957 to implement rigid-body transformation unit 352, deformable transformation unit 354, gravity unit 355, feature locator 356, and/or binary image generator 357, respectively.

In one example of operation, processor 1980 receives one or more images 158 via interface 1990 and stores these to data storage 1970. Processor 1980 retrieves image(s) 158 from data storage 1970 and executes location instructions 1930 to determine 3D spatial properties 128 based upon image(s) 158. Processor 1980 stores 3D spatial properties 128 to data storage 1970. Next, processor 1980 retrieves 3D spatial properties 128 from data storage 1970 and executes surgical cue generation instructions 1940 to determine surgical guidance cues 138 based upon 3D spatial properties 128. Processor 1990 may store surgical guidance cues 138 to data storage 1970 and/or output surgical guidance cues 138 via interface 1990.

In another example of operation, processor 1980 receives one or more images 358 via interface 1990 and stores these to data storage 1970. Processor 1980 retrieves image(s) 358 from data storage 1970 and executes image registration instructions 1950 to generate one or more images 158 before proceeding as outlined above in the example where processor 1980 receives image(s) 158 via interface 1990.

Figure 20:
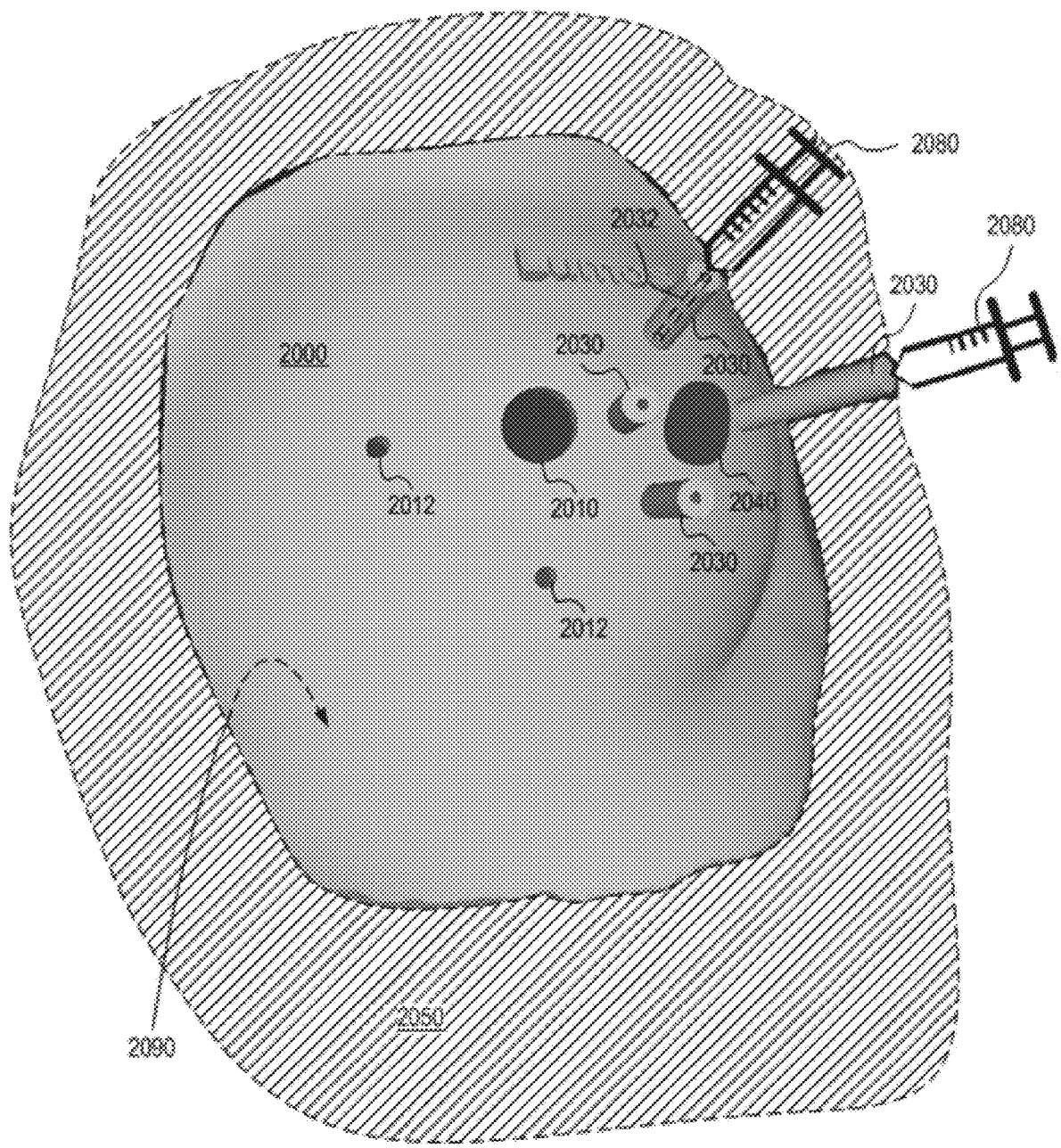
FIG. 20 illustrates a patient-specific locator form for guiding tissue resection, according to an embodiment.

FIG. 20 illustrates one exemplary patient-specific locator form 2000 for guiding tissue resection. As shown in FIG. 20, locator form 2000 is designed to guide resection of tumor 175 from patient 170. However, locator form 2000 is readily adapted for use in other tissue resection procedures including, but not limited to, tumor resection from other body parts and organs, such as the brain or the liver, and biopsy procedures of, e.g., breast 172, muscle, or bone. Locator form 2000 is also readily adapted to guide local delivery of markers or a therapeutic agent to patient 170.

Locator form 2000 includes features that indicate surgical guidance cues 138 and/or features that enable surgeon 180 to transfer surgical guidance cues 138 to breast 172. Locator form 2000 may help ensure good agreement between tissue position properties of breast 172, upon which surgical guidance cues 138 are based, and tissue position properties of breast 172 when transferring surgical guidance cues 138 to breast 172. In one example of use, locator form 2000 stays on breast 172 during resection of tumor 175. This helps maintain stable position of breast 172, thus ensuring good agreement between tissue position properties associated with the tissue resection procedure and tissue position properties upon which surgical guidance cues 138 are based. In another example of use, locator form 2000 is used to transfer surgical guidance cues 138 to breast 172 in step 440 of method 400, and may be removed prior to resection surgery.

Locator form 2000 is custom made for patient 170 to fit breast 172. Locator form 2000 includes an inner surface 2090 that is adjacent to breast 172 when locator form 2000 is placed on breast 172. Inner surface 2090 is not visible in FIG. 20, since inner surface 2090 faces away from the observer viewing FIG. 20.

For use in other tissue resection procedures than resection of tumor 175, inner surface 2090 may be adapted to fit the shape of the body part/organ associated with such tissue resection procedures. For example, inner surface 2090 may be adapted to fit the skull of a patient undergoing brain tumor resection or brain tissue biopsy.

Locator form 2000 includes fiducials that may be matched to fiducials on breast 172 to ensure proper positioning of locator form 2000 on breast 172. In the example shown in FIG. 20, locator form 2000 includes (a) a fiducial 2010 that is an opening configured to fit the nipple of breast 172, and (b) fiducials 2012 configured to match markings applied to breast 172. Locator form 2000 may include more, fewer, or different fiducials than those shown in FIG. 20, without departing from the scope hereof. In an alternative embodiment, locator form 2000 does not include fiducials 2010 and 2012, and proper placement of locator form 2000 is instead ensured by the general shape of inner surface 2090.

For use in tissue resection procedures other than resection of tumor 175, fiducials 2010/2012 may be adapted to match fiducials on the body part/organ associated with such tissue removal procedures.

Locator form 2000 has a cutout 2040 at the intended incision site for resection of tumor 175. In one embodiment, cutout 2040 is shaped and sized to match projection 224. Thus, cutout 2040 may function as an indicator of projection 224 and/or may enable surgeon to mark projection 224 onto surface 174. In another embodiment, cutout 2040 is oversized as compared to projection 224 but allows surgeon 180 to mark projection 224 onto surface 174, for example guided by an OR navigation system as discussed in reference to FIGS. 4A and 4B. Although not shown in FIG. 20, cutout 2040 may be a small cutout that enables surgeon 180 to accurately mark point 222 on surface 174, without departing from the scope hereof. Furthermore, locator form 2000 may include one or more additional small cutouts that enable surgeon 180 to accurately mark one or more margins of projection 224 (such as cranial margin 242, caudal margin 244, lateral margin 246, and/or medial margin 248), and/or other positions along the perimeter of projection 224 or within projection 224, on surface 174.

Locator form 2000 includes at least one raised needle port 2030. Each raised needle port 2030 has a cannulation 2032 configured to accept a needle of a syringe 2080.

In one embodiment, locator form 2000 is made of a material that is at least partly transmissive to light, such that surgeon may see breast 172 through locator form 2000. In another embodiment, a portion of locator form 2000 is made of a material that is at least partly transmissive to light, such that surgeon may see at least a portion breast 172 through this light-transmissive portion of locator form 2000. In another embodiment, locator form 2000 is tessellated (for example according to a Voronoi pattern) to reduce the amount of material required to produce location form 2000 without compromising the structural integrity or accuracy of locator form 2000.

In certain embodiments, locator form 2000 is extended to further include a form portion 2050 that is configured to match the shape of portions of patient 170 near breast 172. In one example, form portion 2050 is configured to match the shape of more rigid anatomical structures of patient 170 such as at least a portion of the rib cage and/or sternum of patient 170. Form portion 2050 may improve the accuracy of alignment of locator form 2000 with respect to patient 170.

Without departing from the scope hereof, locator form 2000 may include only some of the features shown in FIG. 20. For example, some embodiments of locator form 2000 such as those for use with robotic injectors may omit raised needle ports 2030.

Although not shown in FIG. 20, locator form 2000 may include, or be configured to attach to, one or more restraining mechanisms to secure locator form 2000 to breast 172 after aligning locator form 2000 to breast 172 using fiducials 2010 and 2012. Exemplary restraining mechanisms include elastic and non-elastic straps.

In an alternative use scenario, locator form 2000 is placed on patient 170 to place a marker or therapeutic agent in local tissue of patient 170 through raised needle port(s) 2030. For example, locator form 2000 may be used to inject radioactive seeds into an organ of patient 170, such as the prostate or breast 172 of patient 170.

Figure 21A:
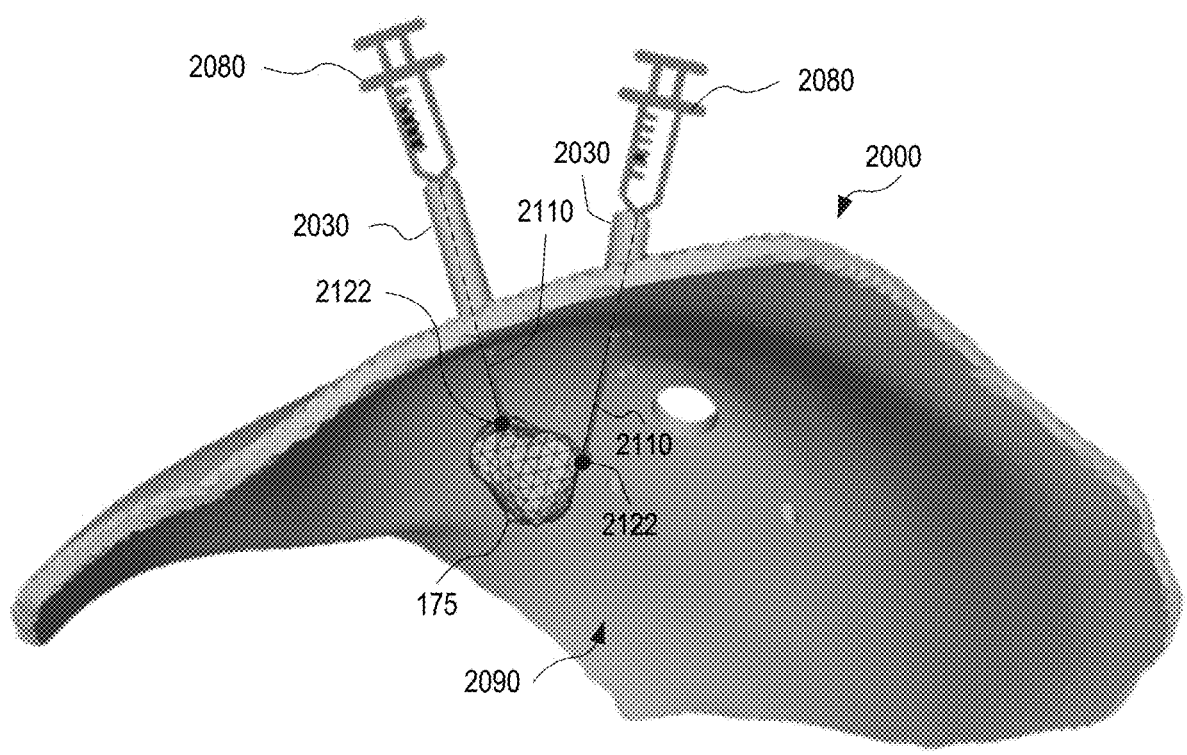
FIG. 21A illustrates functionality of raised needle ports of the locator form of FIG. 20, according to an embodiment.

FIG. 21A further illustrates the functionality of exemplary raised needle ports 2030. FIG. 21A is best viewed together with FIG. 20. By virtue of cannulation 2032, raised needle port 2030 defines a direction 2110 to a location 2122 within breast 172. For example, direction 2110 may lead to a location 2122 associated with tumor 175, such as a margin of tumor 175, or other location within or on the perimeter of tumor 175, wherein this margin, or other interior or perimeter location, may be extended from tumor 175 by a volumetric safety margin 282 as discussed in reference to FIG. 2C. Raised needle port 2030 is configured to passively guide a needle of known length to location 2122. Surgeon 180 may use raised needle port to inject a dye into tumor 175, either to mark all of tumor 175 or to mark a margin (or other interior or perimeter location) of tumor 175. As an alternative to dye, surgeon 180 may use other physical markers including, but not limited to, biocompatible self-powered light-emitting diodes, a radioactive seed, RF-sensitive markers (such as those disclosed in U.S. Pat. No. 8,892,185), cauterization, and other markers known in the art. Surgeon 180 may use raised needle port 2030 to insert an associated delivery device into breast 172, such as those disclosed in U.S. Pat. No. 8,892,185 or other devices known in the art. In one example, surgeon 180 uses raised needle port 2030 and an associated delivery device to inject radioactive seed(s) or RF-sensitive markers to the centroid 212 of tumor 210. Marking of tumor 175 may provide a surgical guidance cue to aid assessment of resection of tumor 175 and, in turn, help ensure that all cancerous tissue is removed from breast 172. Syringe 2080 (or an alternative delivery device) may be configured to inject a metered volume of dye (or an alternative marker) to avoid excessive diffusion of dye (or alternative marker) to a larger region than intended.

In an alternative embodiment, one raised needle port 2030 is placed at the incision site (for example at point 222) for resection of tumor 175 and is used to place a hook wire at location 2122, such that a distal end of the hook wire is at location 2122 and a proximal end of the hook wire exits surface 174 at the incision site. In this embodiment, the hook wire functions as a surgical guidance cue, and this raised needle port 2030 enables accurate placement of the hook wire to provide this surgical guidance cue with high accuracy. In one example of this embodiment, this raised needle port 2030 directs the hook wire to anterior margin 214. In another example of this embodiment, this raised needle port 2030 directs the hook wire to the center of tumor 175 (at or near centroid 212). In yet another example of this embodiment, this raised needle port 2030 directs the hook wire to a surface of tumor 175 such as an anterior or posterior surface of tumor 175. In this example, this raised needle port 2030 may direct the hook wire through the center of tumor 175 to the posterior surface of tumor 175, for example to posterior margin 216. In a further example of this embodiment, this raised needle port 2030 directs the hook wire to a location within tumor 175. Without departing from the scope hereof, this raised needle port 2030 may be placed away from the incision point (point 222, for example) and be oriented to direct the hook wire to tumor 175 (for example, to anterior margin 214, the center of tumor 175, a posterior surface of tumor 175, an anterior surface of tumor 175, or another location on or within tumor 175) from a location that is different from the incision point.

In certain embodiments, locator form 2000 includes (a) one raised needle port 2030 configured to passively guide a hook wire to tumor 175 as discussed above, and (b) one or more raised needle ports 2030 each configured to passively guide a syringe 2080 (or alternative delivery device) to tumor 175 as discussed above.

The functionality of raised needle port 2030 (or alternative fiducial) is readily extended to marking of tumors in other body parts/organ, such as the brain or liver, or alternatively to local delivery of a therapeutic agent. Furthermore, raised needle port 2030 may be configured to accept a biopsy needle and thus function as a surgical guidance cue for a biopsy procedure of, e.g., breast 172, muscle, or bone.

Figure 21B:
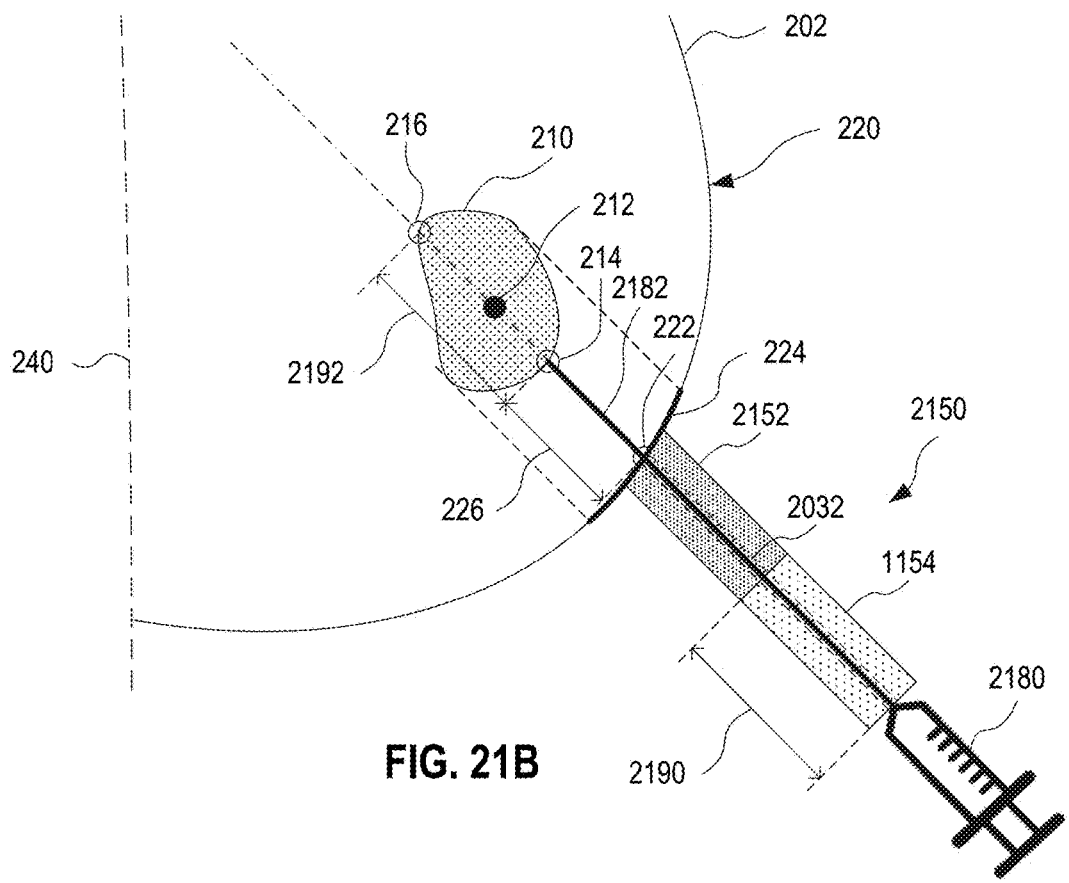
FIGS. 21B and 21C illustrate a two-part raised needle port of the locator form of FIG. 20, which targets two different positions, according to an embodiment.
Figure 21C:
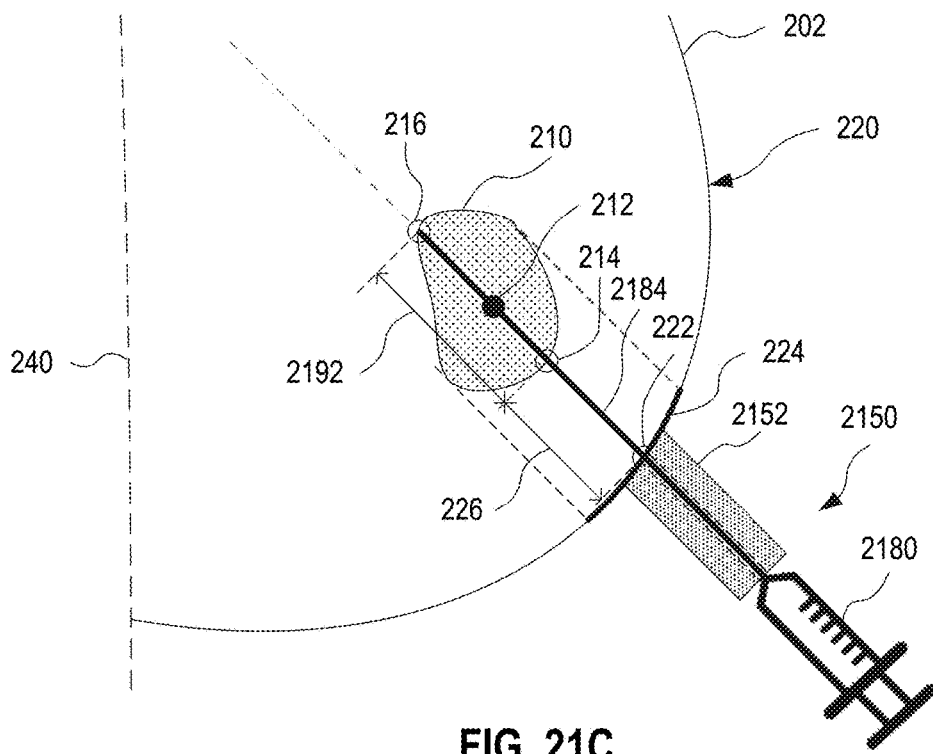

FIGS. 21B and 21C illustrate one exemplary two-part raised needle port 2150 that targets two different positions within breast 172. Two-part raised needle port 2150 is an embodiment of raised needle port 2030. Two-part raised needle port 2150 includes a base portion 2152, closest to inner surface 2090, and a removable spacer portion 2154 furthest from inner surface 2090. Cannulation 2032 extends through both of base portion 2152 and spacer portion 2154 such that a needle may be inserted into breast 172 through cannulation 2032. FIG. 21B shows two-part raised needle port 2150 with spacer portion 2154 and FIG. 21C shows two-part raised needle port 2150 without spacer portion 2154. FIGS. 21B and 21C are best viewed together.

FIGS. 21B and 21C illustrate two-part raised needle port 2150 as implemented in locator form 2000. For clarity of illustration, FIGS. 21B and 21C do not show other parts of locator form 2000. In the scenario shown in FIGS. 21B and 21C, two-part raised needle port 2150 is configured to (a) direct a syringe needle 2182 of syringe 2080 through the incision site (point 222) to anterior margin 214 when spacer portion 2154 is in place to inject dye at anterior margin 214, and (b) direct a hook wire insertion needle 2184 of a hook wire insertion device 2180 through the incision site (point 222, for example) to posterior margin 216 when spacer portion 2154 is removed from two-part raised needle port 2150 to place a hook wire at posterior margin 216 with the hook wire passing through the incision point. However, without departing from the scope hereof, two-part raised needle port 2150 may be used to target any two positions located at two different depths within breast 172 along the axis defined by cannulation 2032. Furthermore, two-part raised needle port 2150 may be used to target two such positions for injection of dye or other markers to both of these positions.

In one embodiment, two-part raised needle port 2150 is configured for use with two needles of the same length, and spacer portion 2154 has length 2190 equal to the distance 2192 between the two targeted positions. In another embodiment, two-part raised needle port 2150 is configured for use with two needles of different lengths, and spacer portion 2154 has length 2190 that is distance 2192 corrected for the different needle lengths. Two-part raised needle port may accept needles of a variety of calibers such that the two different needles may be of different caliber.

The functionality of two-part raised needle port 2150 is readily extended to marking of tumors in other body parts/organ, such as the brain or liver, or to local delivery of a therapeutic agent. Furthermore, two-part raised needle port 2150 may be configured to accept a biopsy needle and thus function as a surgical guidance cue for a biopsy procedure of, e.g., breast 172, muscle, or bone.

Figure 22:
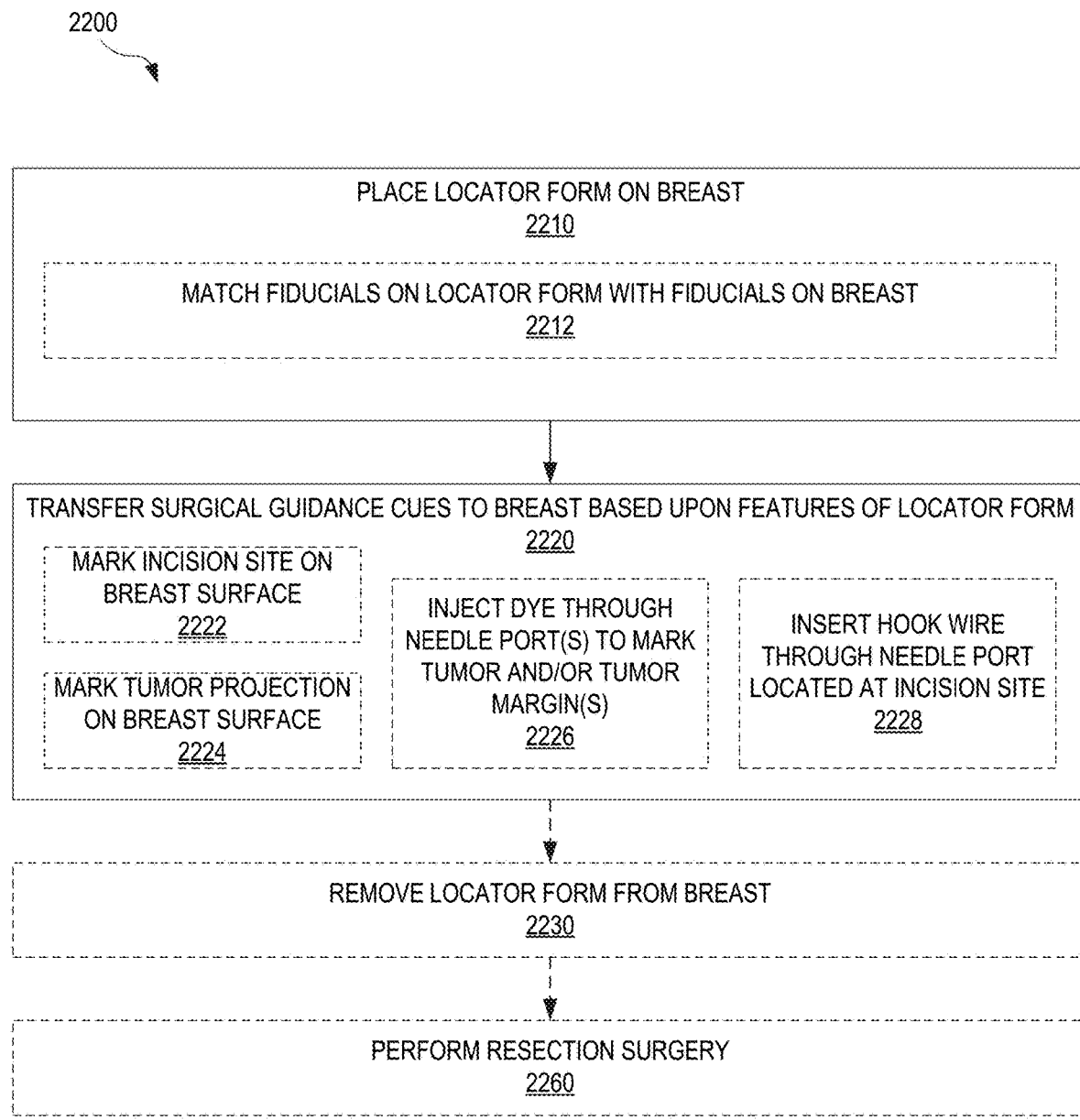
FIG. 22 illustrates a method for guiding tumor resection using a locator form, according to an embodiment.

FIG. 22 illustrates one exemplary method 2200 for guiding resection of tumor 175 using a locator form such as locator form 2000.

In a step 2210, the locator form is placed on breast 172. Step 2210 may include a step 2212 of matching fiducials on the locator form with fiducials on breast 172. In one example of step 2210, locator form 2000 is placed on breast 172 with inner surface 2090 facing surface 174. Optionally, fiducial 2010 is placed at the location of the nipple of breast 172 and fiducials 2012 are matched to fiducials on surface 174.

In a step 2220, surgical guidance cues 138 are transferred to breast 172 using features of the locator form. In one example of step 2220, surgical guidance cues 138 are transferred to breast 172 using features of locator form 2000.

Step 2220 may include a step 2222 of marking the incision site, for resection of tumor 175, at least in part based upon a feature of the locator form. In one example of step 2222, point 222 is marked on surface 174 based upon cutout 2040 and optionally further guided by other OR navigation systems, such as those discussed in reference to FIG. 1. In another example of step 2222, point 222 and one or more of cranial margin 242, caudal margin 244, lateral margin 246, and/or medial margin 248 (and/or other tumor perimeter location) are marked on surface 174 based upon respectively smaller cutouts of locator form 2000, as discussed in reference to FIG. 20. In yet another example of step 2222, the perimeter of projection 224 is marked on surface 174. In this example, cutout 2040 may match the shape and location of the perimeter of projection 224.

Step 2220 may include a step 2224 of marking projection 224 of tumor 175 onto surface 174 as guided by a feature of the locator form. In one example of step 2224, cutout 2040 of locator form 2000 matches projection 224, and projection 224 is marked on surface 174 as guided by cutout 2040.

Optionally, step 2220 includes a step 2226 of injecting dye (or other marker) into tumor 175 through a needle port of the locator form. In one example of step 2226, dye (or other marker) is injected into tumor 175 to mark the volume of tumor 175 or a margin of tumor 175, such as anterior margin 214 or posterior margin 216, (and/or one or more other locations on the perimeter of tumor 175) using a syringe 2080 guided by cannulation 2032 of a corresponding raised needle port 2030. Step 2226 may utilize a plurality of raised needle ports 2030 to mark different portions of tumor 175. Alternatively, step 2220 may include a step 2228 of inserting a hook wire into breast 172, for example as discussed in reference to FIGS. 21A-C.

Optionally, the locator form is removed from breast 172 in a step 2230 subsequent to step 2220.

In an embodiment, method 2200 includes a step 2260 of performing resection surgery to remove tumor 175. In one implementation, step 2260 is performed after removal of the locator form in step 2230. This may improve access to breast 172, as compared to when the locator form is in place on breast 172. In another implementation, step 2260 is performed while the locator form is in place on breast 172. This may help maintain the tissue positions properties, upon which features of the locator form are based. In one example, a biopsy procedure is performed with the locator form in place on breast 172. In another example, an ablative tumor resection surgery, such as RF ablation, cryogenic ablation, or high-intensity focused ultrasound ablation, is performed with the locator form in place on breast 172.

Method 2200 is readily extended to tumor resection from other body parts/organs of patient 170. Additionally, method 2200 may be extended to other tissue resection procedures, biopsy procedures, or therapeutic agent delivery procedures, without departing from the scope hereof. In one such example, method 2200 is implemented with step 2226 (or step 2228), whereafter, in step 2260, a biopsy needle is inserted into breast 172 to the location marked in step 2226. In another example, a biopsy needle is inserted into breast 172 in step 2228.

Figure 23:
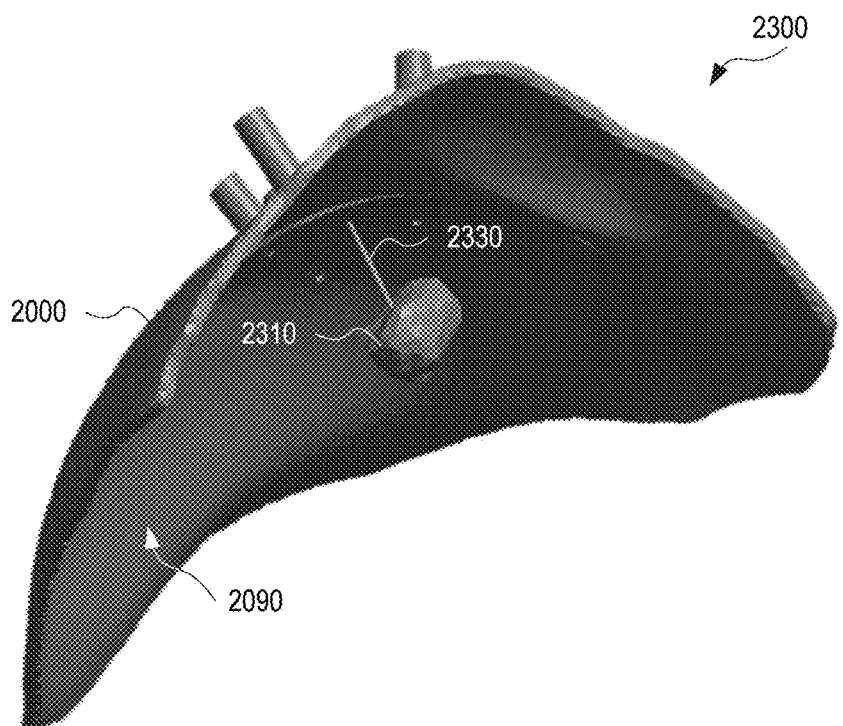
FIG. 23 illustrates a patient-specific locator form that further includes a material model of a tumor, according to an embodiment.

FIG. 23 illustrates a patient-specific locator form 2300 that further includes a material model of tumor 175. Patient-specific locator form 2300 is an extension of patient-specific locator form 2000, which further includes a material model 2310 of tumor 175 and a connecting rod 2330. Connecting rod 2330 is configured to cooperate with locator form 2000 to place material model 2310 in a location that matches the location of tumor 175 relative to surface 174. Locator form 2300 helps surgeon 180 visualize the geometry associated with resection surgery to remove tumor 175.

Locator form 2300 is readily extended to other tissue resection procedures by modifying locator form 2000 as discussed above and replacing material model 2310 with a material model of the tissue to be removed in such other tissue resection procedures.

Figure 24:
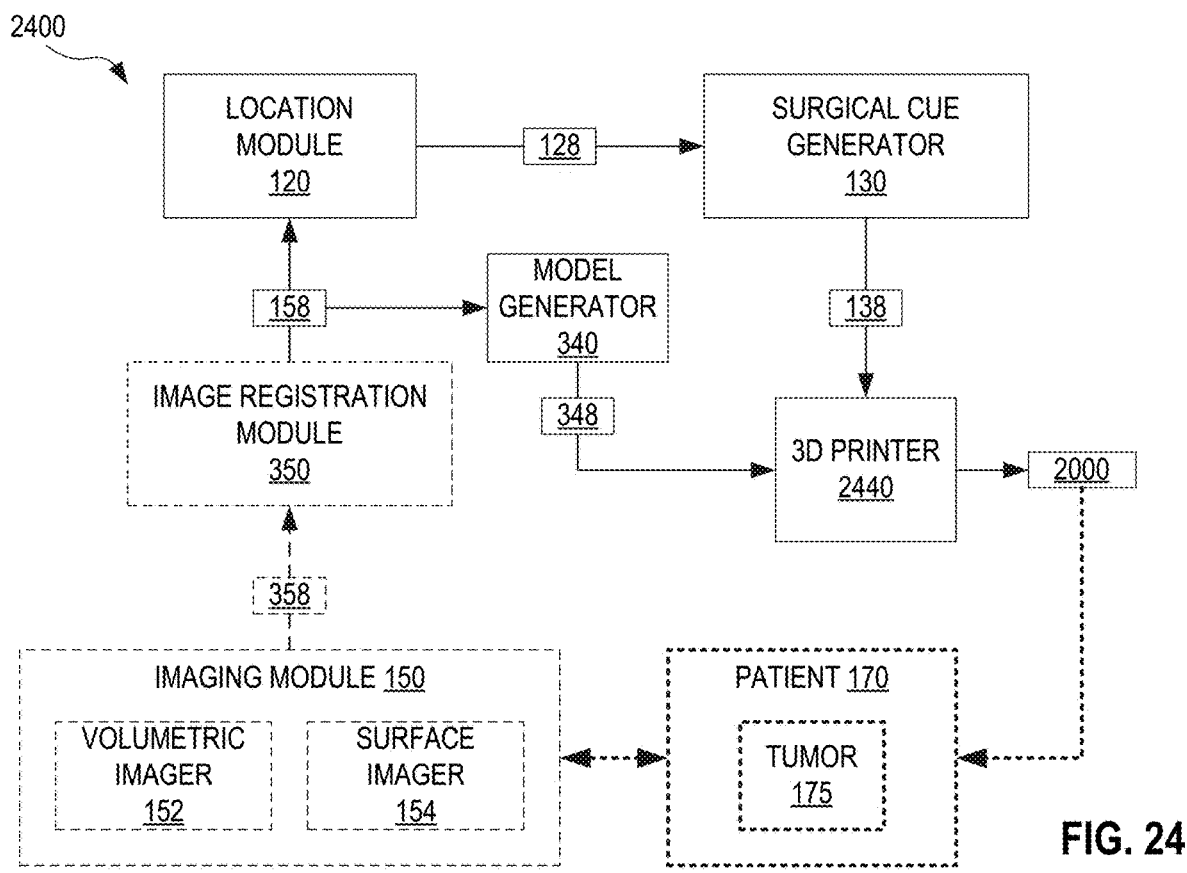
FIG. 24 illustrates a system for manufacturing a patient-specific locator form, according to an embodiment.

FIG. 24 illustrates one exemplary system 2400 for manufacturing patient-specific locator form 2000. System 2400 is an extension of system 100, which includes model generator 340 and further includes a 3D printer 2440 for additively manufacturing locator form 2000 based upon determined surgical guidance cues 138 and model 348.

Model generator 340 communicates a 3D surface model 348 of at least a portion of surface 174 to 3D printer 2440. Based upon this 3D surface model 348, 3D printer 2440 additively manufactures locator form 2000 such that inner surface 2090 substantially matches surface 174. 3D printer 2440 additively manufactures locator form 2000 with features (such as cutout 2040) that indicate one or more surgical guidance cues 138 and/or features (such as raised needle port(s) 2030 or alternative needle fiducials) that may be utilized to transfer one or more surgical guidance cues 138 to breast 172. In certain implementations, model generator 340 further communicates a volumetric model 348 of tumor 175 to 3D printer 2440, and 3D printer 2440 further manufactures material model 2310 and connecting rod 2330.

Without departing from the scope hereof, tumor 175 may be other local tissue than a breast tumor, for example a tumor in a different organ/body part of patient 170, local tissue from which a biopsy must be performed, or local tissue to which a therapeutic agent must be delivered, and system 2400 may produce a locator form 2000 that matches an associated surface of patient 170. Also without departing from the scope hereof, system 2400 may utilize prone images of breast 172 as opposed to supine images 158, so as to produce a locator form that fits breast 172 in prone position.

Figure 25:
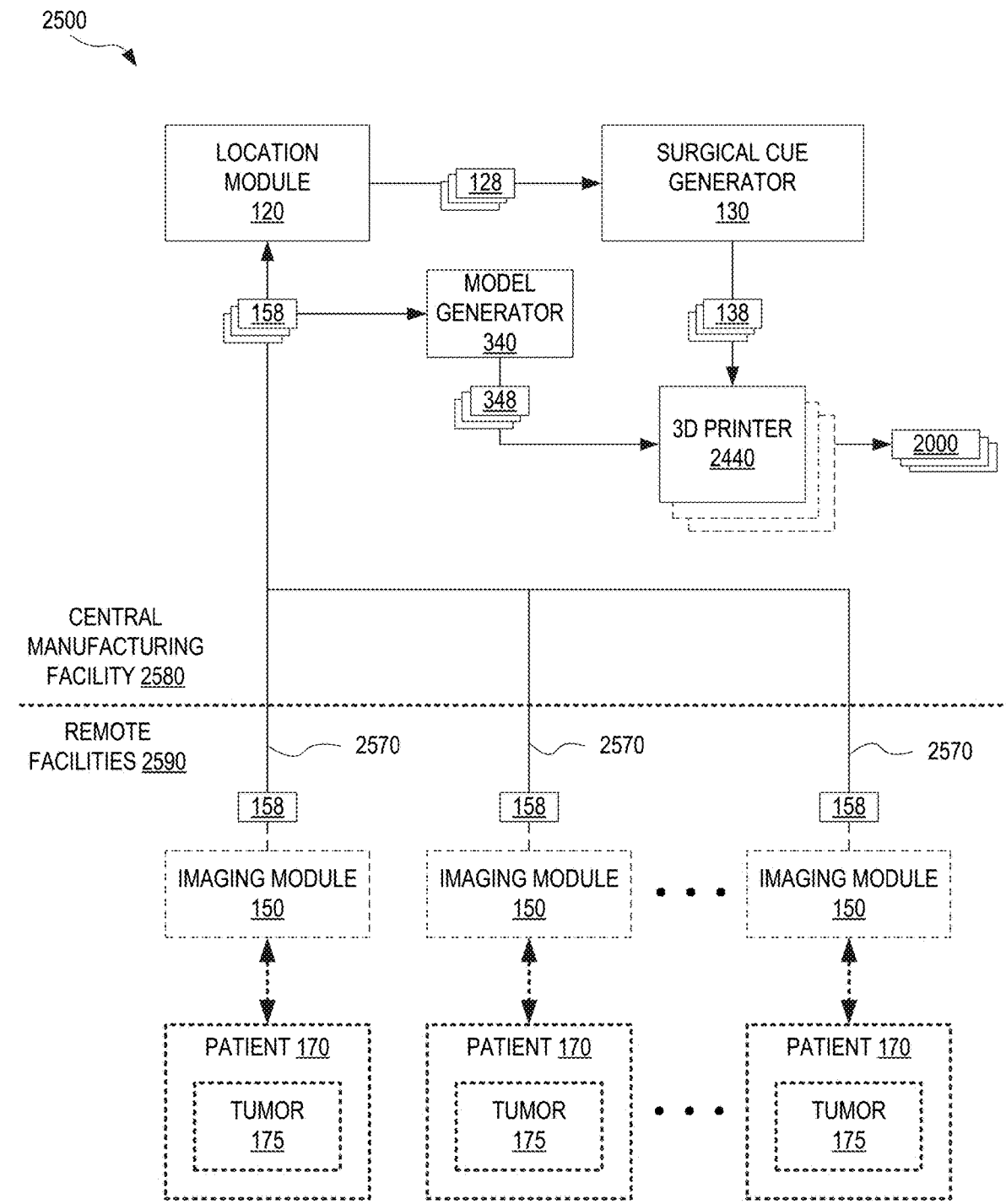
FIG. 25 illustrates a system for manufacturing a plurality of patient-specific locator forms for a respective plurality of patients, according to an embodiment.

FIG. 25 illustrates one exemplary system 2500 for manufacturing a plurality of patient-specific locator forms 2000 for a respective plurality of patients 170 based upon supine images 158. System 2500 is located at a central manufacturing facility 2580, while patients 170 and associated imaging modules 150 may be located at one or more remote facilities 2590. Remote facilities 2590 are, for example, one or more hospitals or operating/imaging facilities remote from central manufacturing facility 2580. Each imaging module 150 of remote facilities 2590 communicates at least one supine image 158 of breast 172, of respective patient 170, via a data connection 2570 to location module 120 and model generator 340 at central manufacturing facility 2580. Based upon supine images 158, location module 120 and surgical cue generator 130 generates surgical guidance cues 138 for each patient 170, and model generator 340 generates model 348 for each patient 170, as discussed in reference to FIG. 24 for a single patient 170. Using surgical guidance cues 138 for each patient 170 and model 348 for each patient 170, one or more 3D printers 2440 additively manufactures a locator form 2000 specific to each patient 170, as discussed in reference to FIG. 24 for a single patient 170.

Each data connection 2570 may be a Digital Imaging and Communications in Medicine (DICOM) connection.

Although not shown in FIG. 25, system 2500 may include image registration module 350 such that system 2500 may receive images 358 instead of supine images 158, without departing from the scope hereof. System 2500 is readily extended to production of locator forms for guiding other tissue resection procedures than breast tumor resection, without departing from the scope hereof.

Figure 26:
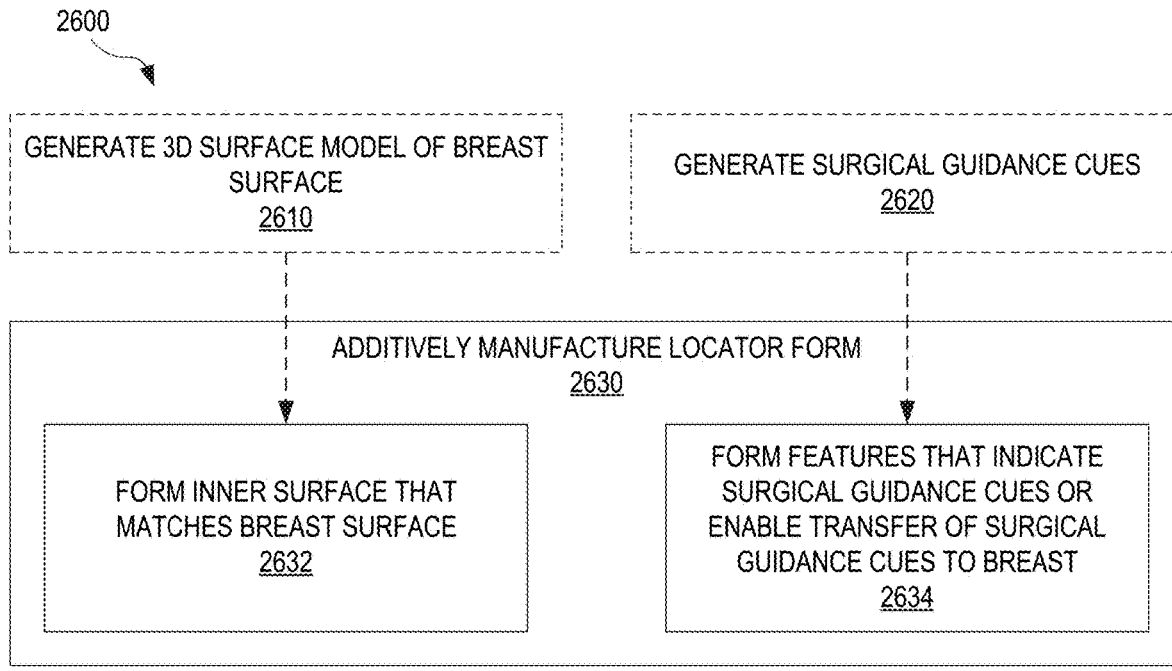
FIG. 26 illustrates a method for producing a patient-specific locator form, according to an embodiment.

FIG. 26 illustrates one exemplary method 2600 for producing patient-specific locator form 2000 for breast 172. In a step 2630, 3D printer 2440 additively manufactures locator form 2000 based upon (a) a 3D surface model 348 of surface 174 and (b) surgical guidance cues 138. Step 2630 includes a step 2632 of additively manufacturing locator form 2000 to form inner surface 2090, based upon 3D surface model 348. Step 2630 further includes a step 2634 of additively manufacturing locator form 2000 to form features that indicate surgical guidance cues 138 and/or features that enable transfer of surgical guidance cues to breast 172. In one example of step 2634, 3D printer 2440 forms one or more features such as features discussed in reference to FIGS. 20 and 21.

In an embodiment, method 2600 further includes a step 2610 of generating 3D surface model 348 of surface 174. In one example of step 2610, model generator 340 generates 3D surface model 348 of surface 174.

In an embodiment, method 2600 further includes a step 2620 of generating surgical guidance cues 138. In one example of step 2610, surgical cue generator 130 generates surgical guidance cues 138. Without departing from the scope hereof, system 2400 (and also system 2500) may implement functionality that specifies features of locator form 2000 based upon surgical guidance cues 138.

Method 2600 is readily extended to production of locator forms for guiding other tissue resection procedures than breast tumor resection, without departing from the scope hereof. Likewise, method 2600 may utilize a 3D surface model 348 and surgical guidance cues 138 generated from prone images of breast 172 as opposed to supine images 158, so as to produce a locator form that fits breast 172 in prone position.

Figure 27:
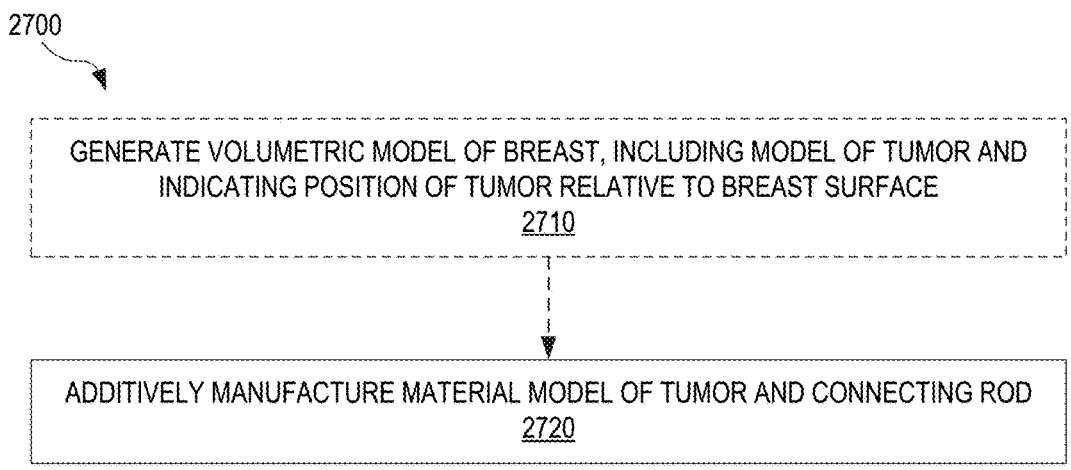
FIG. 27 illustrates a method for producing a material model of a tumor and a connecting rod for incorporating the material model into a patient-specific locator form, according to an embodiment.

FIG. 27 illustrates one exemplary method 2700 for producing material model 2310 and connecting rod 2330. In a step 2720, 3D printer 2440 additively manufactures material model 2310 and connecting rod 2330 based upon a volumetric model 348 of breast 172. This volumetric model 348 includes a model of tumor 175 and indicates position of tumor 175 relative to surface 174. Optionally, method 2700 includes a step 2710 wherein model generator 340 generates this volumetric model 348.

Without departing from the scope hereof, method 2700 may utilize a 3D surface model 348 generated from prone images of breast 172 as opposed to supine images 158, so as to produce material model 2310 and connecting rod 2330 indicative of breast 172 in prone position.

Methods 2600 and 2700 may be combined to produce patient-specific locator form 2300.

FIG. 28 illustrates one exemplary navigation system 2800 for guiding resection of tumor 175 from breast 172 of patient 170 with the aid of surgical guidance cues 138. Navigation system 2800 implements visualization module 140.

Navigation system 2800 includes a display 2810 that displays surgical guidance cues 138. Navigation system 2800 further includes a tracking stylus 2820 and a tracking reference 2830. Although not shown in FIG. 28, navigation system 2800 also includes a computer module that (a) processes tracking data generated by tracking stylus 2820 and tracking reference 2830 to determine the position and, optionally, orientation of tracking stylus 2820, and (b) processes surgical guidance cues 138 (generated by surgical cue generator 130 in step 420 of method 400) and one or more models (generated by model generator 340 in step 430 of method 400) to visualize surgical guidance cues 138 and tracking stylus 2820 on display 2810. Navigation system 2800 uses tracking reference 2830 to reference the position and, optionally, orientation of tracking stylus 2820 to the position and orientation of patient 170.

In the scenario shown in FIG. 28, display 2810 displays a model of breast 172, which includes a model 2812 of breast surface 174 and a model 2814 of tumor 175. Displays 2810 shows model 2812 and model 2814 in proper positional relationships with each other to provide a visualization of breast 172 to surgeon 180. Display 2810 also shows a model 2816 of tracking stylus 2820 overlaid on models 2812 and 2814 to provide surgeon 180 with a visualization of the actual position and, optionally, orientation of tracking stylus 2820 with respect to features in models 2812 and 2814. Although not visible in FIG. 28, display 2810 shows surgical guidance cues 138 overlaid on models 2812 and 2814.

Guided by display 2810, surgeon 180 moves tracking stylus 2820 to mark surgical guidance cues 138 on surface 174, thus transferring one or more surgical guidance cues 138 to surface 174. In the example shown in FIG. 28, surgeon 180 uses tracking stylus 2820 to mark, on surface 174, incision site 2850 and projection 2840 of tumor 175 onto surface 174 (as discussed in reference to FIGS. 5A-C).

Without departing from the scope hereof, tracking stylus 2820 may be replaced by, or operated in conjunction with, a tracking syringe (or other delivery device). Navigation system 2800 tracks the position and orientation of the tracking syringe and overlays the position and orientation of the tracking syringe on models 2812 and 2814 on display 2810. The tracking syringe may have three non-collinear tracking nodes that allow navigation system 2800 to determine the position and orientation of the tracking syringe.

Fiducial markers 2860 may be placed on surface 174 to aid registration of images 358 to produce surgical guidance cues 138. For clarity of illustration, not all fiducial markers 2860 are labeled in FIG. 28.

Navigation system 2800 is readily extended to tumor resection from other body parts/organs of patient 170. Additionally, navigation system 2800 may be extended to other tissue resection procedures, biopsy procedures, or therapeutic agent delivery procedures, without departing from the scope hereof.

Figure 29:
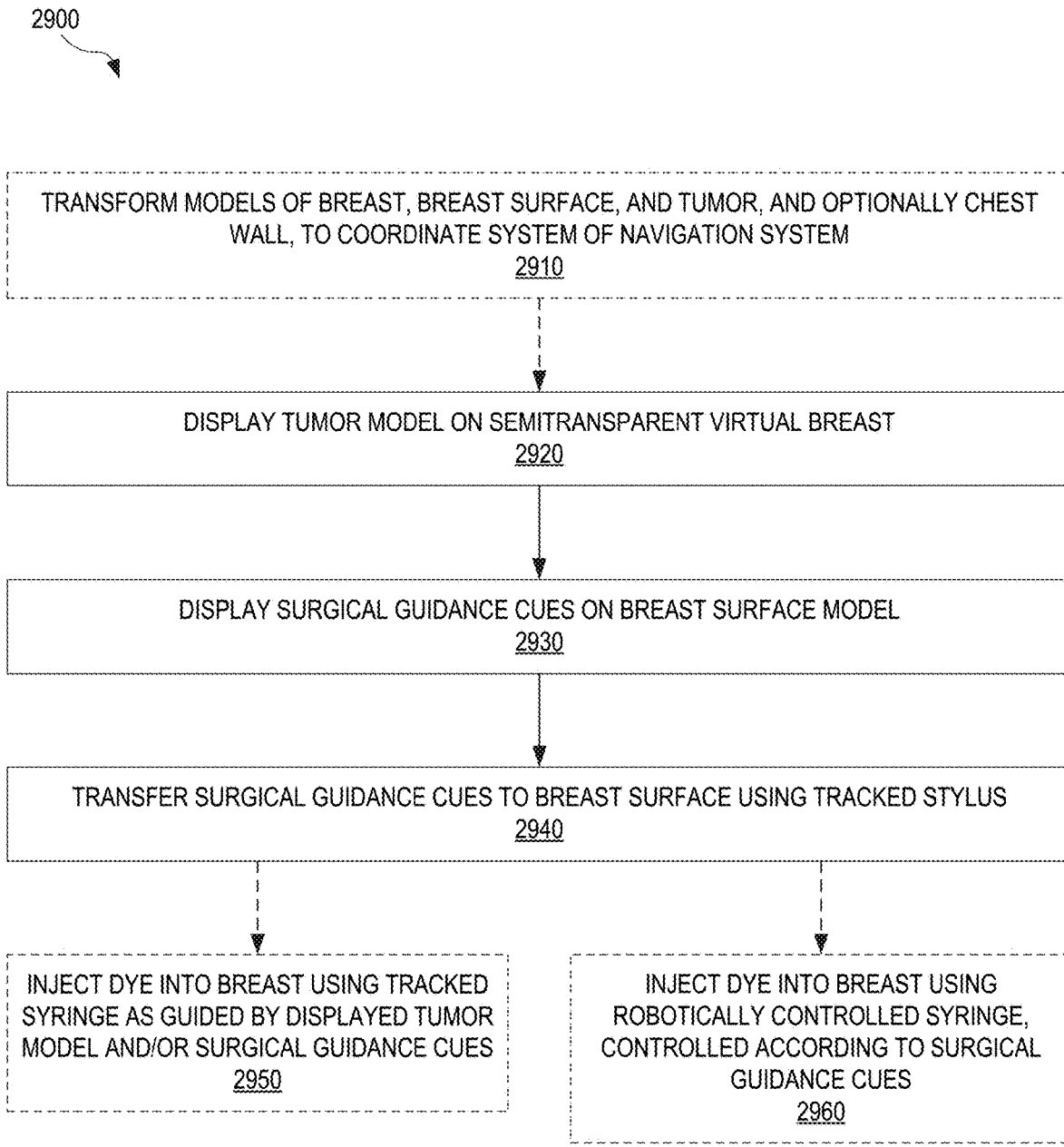
FIG. 29 illustrates a method for visualizing surgical guidance cues using a navigation system, according to an embodiment.

FIG. 29 illustrates one exemplary method 2900 for visualizing surgical guidance cues 138 using a navigation system. Method 2900 is an embodiment of step 430 of method 400.

A step 2920 displays a volumetric model of breast 172. The volumetric model includes a model of surface 174 and a model of tumor 175, wherein the model of surface 174 and the model of tumor 175 are shown in proper positional relationships to each other, thus visualizing breast 172. The model of surface 174 is shown as being semitransparent such that the model of tumor 175 is visible on the display. In one example of step 2920, navigation system 2800 displays models 2812 and 2814, as generated in step 430 of method 400, on display 2810.

A step 2930 overlays surgical guidance cues 138 on the models displayed in step 2920. In one example of step 2930, navigation system 2800 overlays surgical guidance cues 138 on models 2812 and 2814 on display 2810. Without departing from the scope hereof, steps 2920 and 2930 may be performed in the reverse order or in parallel.

Optionally, steps 2920 and 2930 are preceded by a step 2910 of transforming to the coordinate system associated with the navigation system (a) models generated in step 430 of method 400 and displayed in step 2920 and (b) surgical guidance cues 138 generated in step 420 of method 400 and displayed in step 2930. Step 2910 may transform these surgical guidance cues 138 and models to a coordinate system that is referenced to a tracking reference of the navigation system. In one example of step 2910, navigation system 2800 transforms surgical guidance cues 138 and models of breast 172 to a coordinate system referenced to tracking reference 2830.

A step 2940 tracks the position and, optionally orientation, of one or more tracking devices tracked with respect to patient 170. Step 2940 overlays the position and, optionally, orientation of these tracking devices on the models displayed in step 2920. In one example of step 2940, navigation system 2800 tracks the position and, optionally, orientation of tracking stylus 2820 and surgeon 180 uses tracking stylus to mark one or more of the surgical guidance cues 138, for example the incision site (e.g., point 222), on surface 174.

In certain embodiments, method 2900 further includes one or both of steps 2950 and 2960. In step 2950, surgeon 180 uses a tracked syringe (or other delivery device) to inject dye (or other marker, or a therapeutic agent) into breast 172 as guided by the models generated in step 2920 and/or the surgical guidance cues 138 generated in step 2930. In one example of step 2950, surgeon 180 uses a tracked syringe to inject dye into breast 172 at the location of each of one or more margins of tumor 175, such as anterior margin 214 and posterior margin 216, (and/or at one or more other locations on the perimeter of tumor 175) as guided by (a) navigation system 2800 and (b) the models generated in step 2920 and/or the surgical guidance cues 138 generated in step 2930. In step 2960, a robotically controlled syringe (or other delivery device) injects dye (or other marker, or a therapeutic agent) into breast 172 as guided by the models generated in step 2920 and/or the surgical guidance cues 138 generated in step 2930. In one example of step 2960, surgeon 180 uses a tracked syringe to inject dye into breast 172 at the location of each of one or more margins of tumor 175, such as anterior margin 214 and posterior margin 216, (and/or at one or more other locations on the perimeter of tumor 175) as guided by (a) navigation system 2800 and (b) the models generated in step 2920 and/or the surgical guidance cues 138 generated in step 2930.

Method 2900 is readily extended to tumor resection from other body parts/organs of patient 170. Additionally, method 2900 may be extended to other tissue resection procedures, biopsy procedures, or therapeutic agent delivery procedures, without departing from the scope hereof.

FIG. 30 illustrates one exemplary method 3000 for transferring surgical guidance cues 138 to breast 172 using a navigation system and tracking devices. Method 3000 is an embodiment of step 440 of method 400.

In a step 3010, method 3000 uses a tracking stylus to transfer surgical guidance cues 138 to surface 174. In one example of step 3010, surgeon 180 operates tracking stylus 2820. Based upon a visualization generated by method 2900, surgeon 180 marks surface 174 to indicate one or more surgical guidance cues 138 on surface 174. For example, surgeon 180 may indicate incision site 2850 and projection 2840.

Optionally, method 3000 includes a step 3020 of transferring a surgical guidance cue 138 to the interior of breast 172. In step 3020, surgeon 180 uses a tracked syringe to inject dye into breast 172 to mark one or more surgical guidance cues 138 such as cranial margin 242, caudal margin 244, lateral margin 246, medial margin 248, and/or other location(s) on the perimeter of tumor 175. Surgeon 180 places the tracked syringe according to a visualization of the position and orientation of the tracked syringe relative to a model of breast 172. In one example of step 3020, surgeon 180 uses navigation system 2800 implemented with a tracking syringe to place the needle tip of the tracking syringe at a location within breast 172. Surgeon 180 places the needle tip of the tracking syringe as guided by a visualization displayed on display 2810. When the needle tip is at the desired location within breast 172, surgeon 180 injects dye into breast 172 via the syringe.

Method 3000 is readily extended to tumor resection from other body parts/organs of patient 170. Additionally, method 3000 may be extended to other tissue resection procedures, biopsy procedures, or therapeutic agent delivery procedures, without departing from the scope hereof.

FIG. 31 illustrates one exemplary method 3100 for automatically transferring surgical guidance cues 138 to breast 172 using a robotic system. Method 3100 is an embodiment of step 440 of method 400.

In a step 3110, method 3100 uses a robotically controlled stylus to automatically transfer one or more surgical guidance cues 138 to surface 174. The robotically controlled stylus is operated according to surgical guidance cues 138 and models generated in steps 420 and 430 of method 400.

In an optional step 3120, method 3100 uses a robotically controlled syringe to automatically transfer one or more surgical guidance cues 138 to the interior of breast 172 by injecting dye into breast 172 at one or more locations such as one or more of cranial margin 242, caudal margin 244, lateral margin 246, medial margin 248, and/or other location (s) on the perimeter of tumor 175.

Method 3100 is readily extended to tumor resection from other body parts/organs of patient 170. Additionally, method 3100 may be extended to other tissue resection procedures, biopsy procedures, or therapeutic agent delivery procedures, without departing from the scope hereof.

Without departing from the scope hereof, methods 3000 and 3100 may be combined. For example, surgical guidance cues 138 may be transferred to surface 174 using a tracking stylus, as discussed in reference to step 3010 while surgical guidance cues 138 are transferred to the interior of breast 172 using a robotically controlled syringe as discussed in reference to step 3120.

FIG. 32 illustrates one exemplary method 3200 for guiding resection of a tumor 175, which does not require image registration. Method 3200 is an embodiment of method 400 and may be performed by system 100.

In a step 3210, method 3200 generates at least one supine image 158 of breast 172 in a supine position at least substantially the same as the position used during resection surgery. Step 3210 is an embodiment of step 410. In a step 3220, method 3200 performs method 400 without step 410. In an optional step 3230, surgeon 180 performs the tissue resection procedure to resect tumor 175, while utilizing surgical guidance cues 138 determined in step 3220.

In one example of method 3200, breast 172 does not exhibit significant tissue displacement between image capture in step 3210 and tissue resection surgery subsequent to step 3220. In another example of method 3200, a locator form 2000 is manufactured according to image(s) 158 generated in step 3210, and locator form 2000 ensures that, even if tissue displacement takes place between image capture in step 3210 and tissue resection surgery subsequent to step 3220, the tissue positioning of breast 172 is restored to the tissue positioning at the time of image capture in step 3210.

FIG. 33 illustrates one exemplary method 3300 for guiding resection of a tumor 175 based upon preoperative supine volumetric image(s) 358 and supine 3D surface image(s) 358 representative of the supine position used during resection surgery. Method 3300 is an embodiment of method 400 and may be performed by system 100.

In a step 3310, method 3300 generates at least one preoperative volumetric image 358 of breast 172 in a first supine position. In a step 3320, method 3300 generates at least one supine 3D surface image 358 of surface 174 with breast 172 in the same position as associated with the resection surgery. The first supine position is different from the resection-associated position, such that there is some tissue displacement between steps 3310 and 3320. In a step 3330, method 3300 performs method 400 with steps 412 and 414 based upon images captured in steps 3310 and 3320. Steps 3310, 3320, and 3330 together form an embodiment of step 410. In an optional step 3340, surgeon 180 performs the tissue resection procedure to resect tumor 175, while utilizing surgical guidance cues 138 determined in step 3330.

Figure 34:
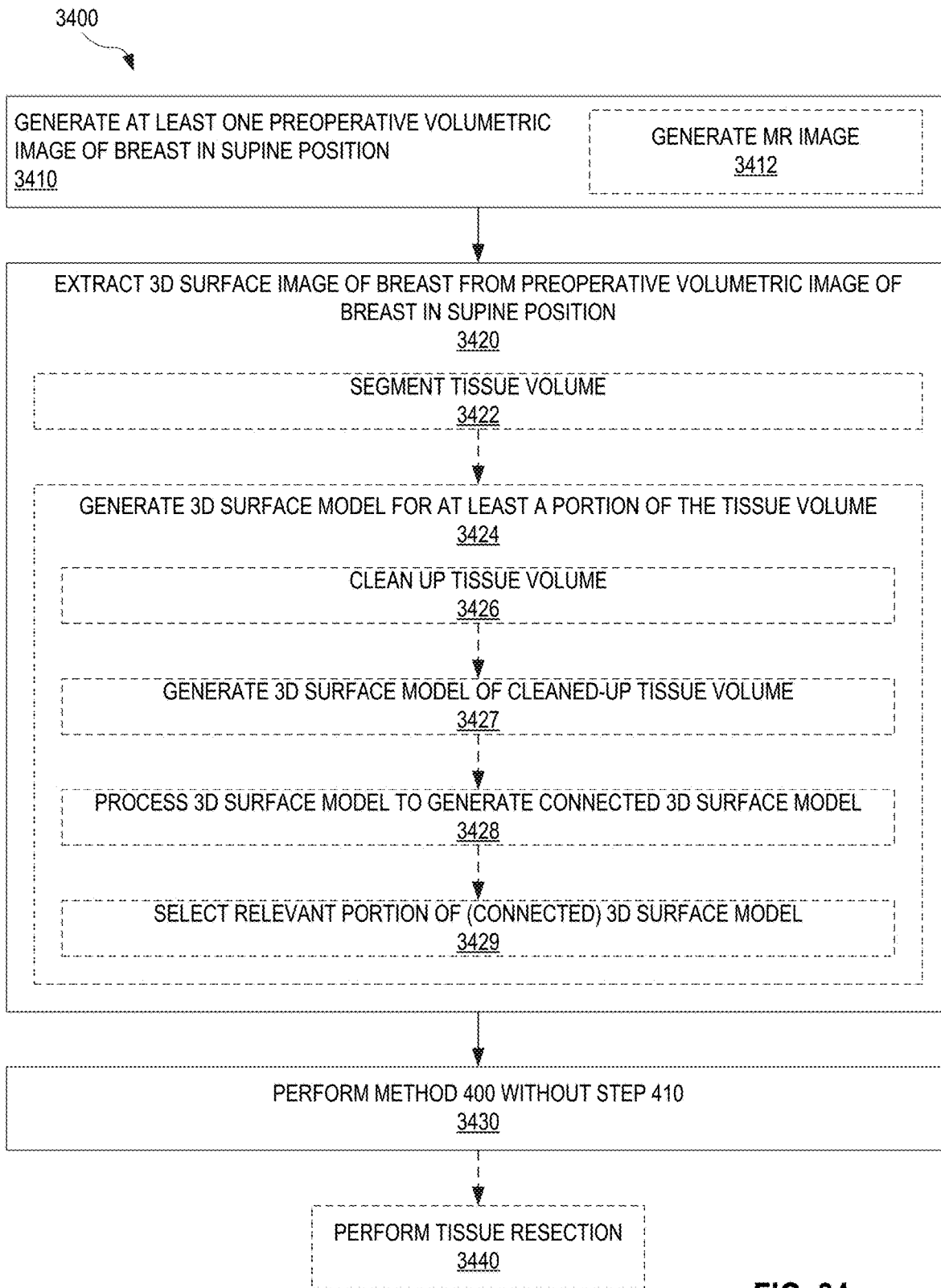
FIG. 34 illustrates a method for guiding resection of a tumor, which extracts both volumetric and surface data from the same preoperative volumetric image(s), according to an embodiment.

FIG. 34 illustrates one exemplary method 3400 for guiding resection of a tumor 175, which extracts both volumetric and surface data from the same preoperative volumetric image(s). Method 3400 thus eliminates the need to co-register volumetric and surface images. Method 3400 is an embodiment of method 400 and may be performed by an embodiment of system 100 that implements volumetric imager 152. Method 3400 does not require surface imager 154. Consequently, method 3400 eliminates the need for acquiring separate surface image(s), and may provide improved accuracy by eliminating any influence from potential co-registration errors between separately acquired volumetric and surface images.

In a step 3410, method 3400 generates at least one preoperative volumetric image 358 of breast 172 in supine position. Optionally, step 3410 implements a step 3412 of generating a magneto resonance image of breast 172 in supine position, which may be a single magneto resonance image or a plurality of substantially co-registered magneto resonance images.

In a step 3420, method 3400 extracts a 3D surface image 358 of breast 172 from the preoperative volumetric image 358 generated in step 3410. This 3D surface image 358 is inherently co-registered with the preoperative volumetric image 358 generated in step 3410.

In a step 3430, method 3400 performs method 400 without step 410. Step 3430 utilizes (a) volumetric image data from the preoperative volumetric image 358 generated in step 3410 and (b) 3D surface image 358 generated in step 3420 and inherently co-registered with the volumetric image data.

In an optional step 3440, surgeon 180 performs the tissue resection procedure to resect tumor 175, while utilizing surgical guidance cues 138 determined in step 3330 based upon data obtained from the preoperative volumetric image 358 generated in step 3410.

In an embodiment, step 3420 includes steps 3422 and 3424. Step 3422 segments the tissue volume in the preoperative volumetric image 358 generated in step 3410, that is, step 3422 identifies tissue versus air in preoperative volumetric image 358 and extracts the tissue volume from preoperative volumetric image 358. Step 3424 processes the tissue volume, segmented in step 3422, to generate a 3D surface model 348 of breast 175. In one embodiment, step 3424 includes sequential steps 3426 and 3427, and optionally also a step 3428. Step 3426 at least partly cleans up the tissue volume, generated in step 3422, for motion and/or signal artifacts to generate a cleaned-up tissue volume. Step 3427 generates a 3D surface model of the cleaned-up tissue volume of step 3426. Step 3427 may utilize a tessellation algorithm or other method known in the art. Optional step 3428 processes the 3D surface model generated in step 3427 to generate a connected ("water-tight") 3D surface model, if the 3D surface model generated in step 3427 is not fully connected. Step 3428 may utilize a Poisson surface reconstruction algorithm, for example as known in the art. Step 3424 may further include a step 3429 of selecting a relevant portion of either the 3D surface model generated in step 3427 or the connected 3D surface model generated in step 3428. Step 3429 may include loading the 3D surface model generated in step 3428 or 3429 into a mesh editing software to manually select and retain useful breast surface while eliminating other unwanted structures. In one example of method 3400 implementing step 3429, step 3430 implements step 438, and the 3D surface model portion selected in step 3429 is the portion intended to be matched with a patient-specific locator form generated in step 438. Without departing from the scope hereof, step 3424 may include step 3427 but not step 3426.

Without departing from the scope hereof, step 3410 may be replaced by a step of receiving preoperative volumetric image(s) 358 from an external system, such as an image repository or a third-party imaging system.

Figure 35:
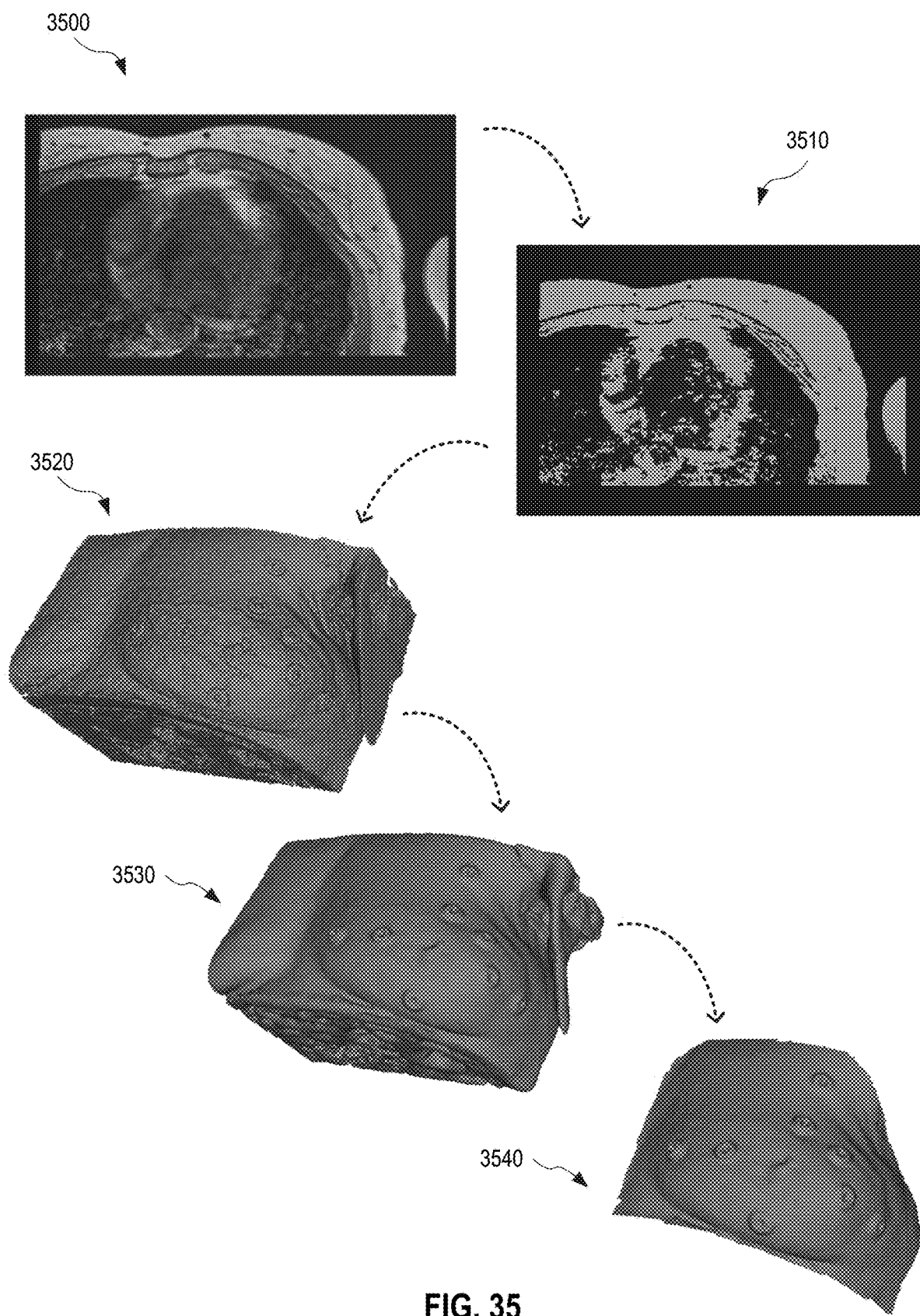
FIG. 35 shows exemplary image data illustrating image processing by one embodiment of the method of FIG. 34.

FIG. 35 shows exemplary image data illustrating image processing by one embodiment of method 3400. In this example, step 3410 generates or receives a high-resolution magneto resonance image 3500 of breast 175, for example with 1-millimeter slice spacing and having a field of view sufficient to include rigid anatomical areas around breast (such as a portion of the sternum and/or portions below the infra mammary fold). Step 3422 segments a tissue volume 3510 from magneto resonance image 3500. Step 3427 (optionally in cooperation with step 3426) generates a 3D surface model 3520. Step 3428 applies a Poisson surface reconstruction algorithm to 3D surface model 3520 to generate a connected 3D surface model 3530. Step 3429 selects a portion of connected 3D surface model 3530 to which a matching patient-specific locator form may be produced in step 438.

FIG. 36 illustrates one exemplary method 3600 for guiding resection of a tumor 175, using a patient-specific locator form manufactured based upon volumetric and surface data obtained from the same preoperative volumetric image(s) 358. Method 3600 is an embodiment of method 400 and of method 3400. Method 3600 includes an embodiment of method 2200. Method 3600 may be performed by an embodiment of system 100 that implements volumetric imager 152 or by an embodiment of system 2400 that implements volumetric imager 152. Method 3600 does not require surface imager 154.

In a step 3610, method 3600 generates at least one preoperative volumetric image 358 of breast 175 in supine position. Step 3610 is an embodiment of step 3410, which includes a step 3612 of utilizing one or more fiducial markers on surface 174 of breast 175 such that the preoperative volumetric image(s) 358 indicates the position of the one or more fiducial markers.

In a step 3620, method 3600 performs step 3420 of method 3400 to extract a 3D surface image 358 of breast 175, wherein the 3D surface image 358 shows the position of the one or more fiducial markers.

In a step 3630, method 3600 performs steps 420, 430, and 438 (and optionally step 436) of method 400 to generate a patient-specific locator form that fits surface 174 of breast 175 and indicates both surgical guidance cues 138 and the positions of the fiducial marker(s) of step 3612.

In certain embodiments, method 3600 includes a step 3640, wherein method 3600 performs steps 2210 (including step 2212) and 2220 of method 2000 to place the patient-specific locator form on breast 175 and transfer surgical guidance cues 138 to breast 175 based upon features of the patient-specific locator form.

Method 3600 may further include a step 3650 of performing step 2260 of method 2200 (optionally preceded by step 2230 of method 2200) to perform the tissue resection surgery with the aid of surgical guidance cues 138 of step 3640.

Figure 37:
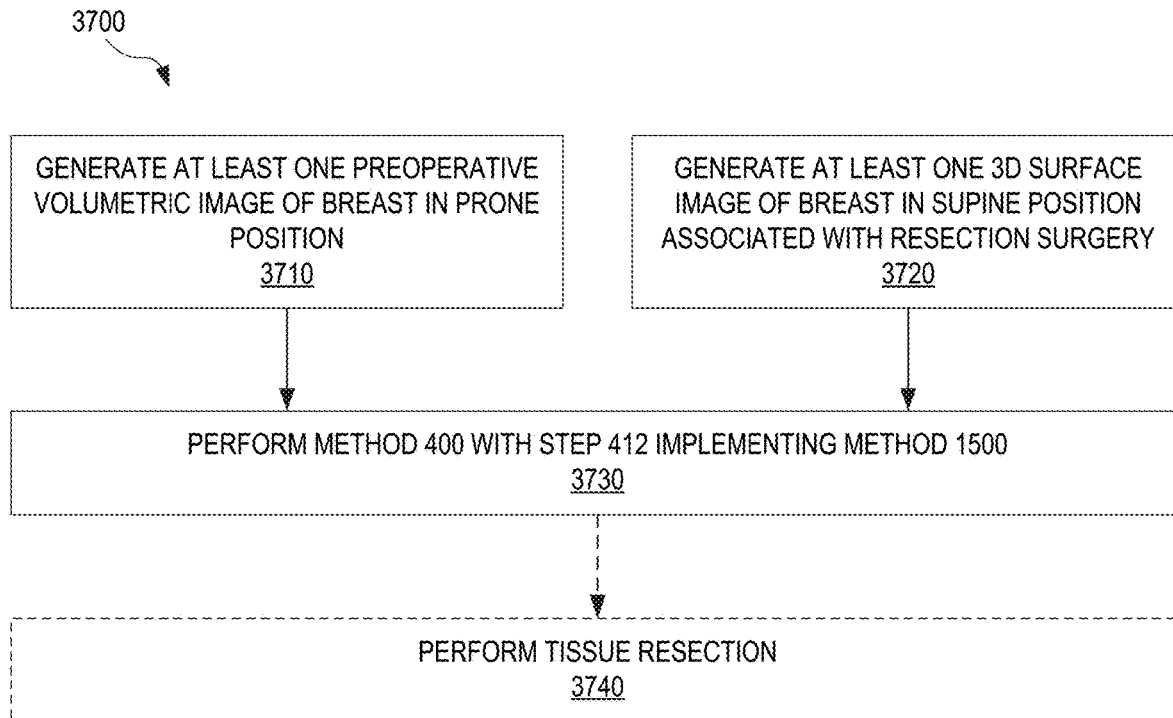
FIG. 37 illustrates a method for guiding resection of a tumor based upon preoperative prone volumetric image(s) and supine 3D surface image(s) representative of the supine position used during resection surgery, according to an embodiment.

FIG. 37 illustrates one exemplary method 3700 for guiding resection of a tumor 175 based upon preoperative prone volumetric image(s) 358 and supine 3D surface image(s) 358 representative of the supine position used during resection surgery. Method 3700 is an embodiment of method 400 and may be performed by system 100.

In a step 3710, method 3700 generates at least one preoperative volumetric image 358 of breast 172 in prone position. In a step 3720, method 3700 generates at least one supine 3D surface image 358 of surface 174 with breast 172 in the same position as associated with the resection surgery. In a step 3730, method 3700 performs method 400 with step 412 based upon the images generated in steps 3710 and 3720 and with step 412 implementing FEM method 1500 to account for the significant tissue displacement between step 3710 and step 3720. Steps 3710, 3720, and 3730 together form an embodiment of step 410. In an optional step 3740, surgeon 180 performs the tissue resection procedure to resect tumor 175, while utilizing surgical guidance cues 138 determined in step 3730.

Figure 38:
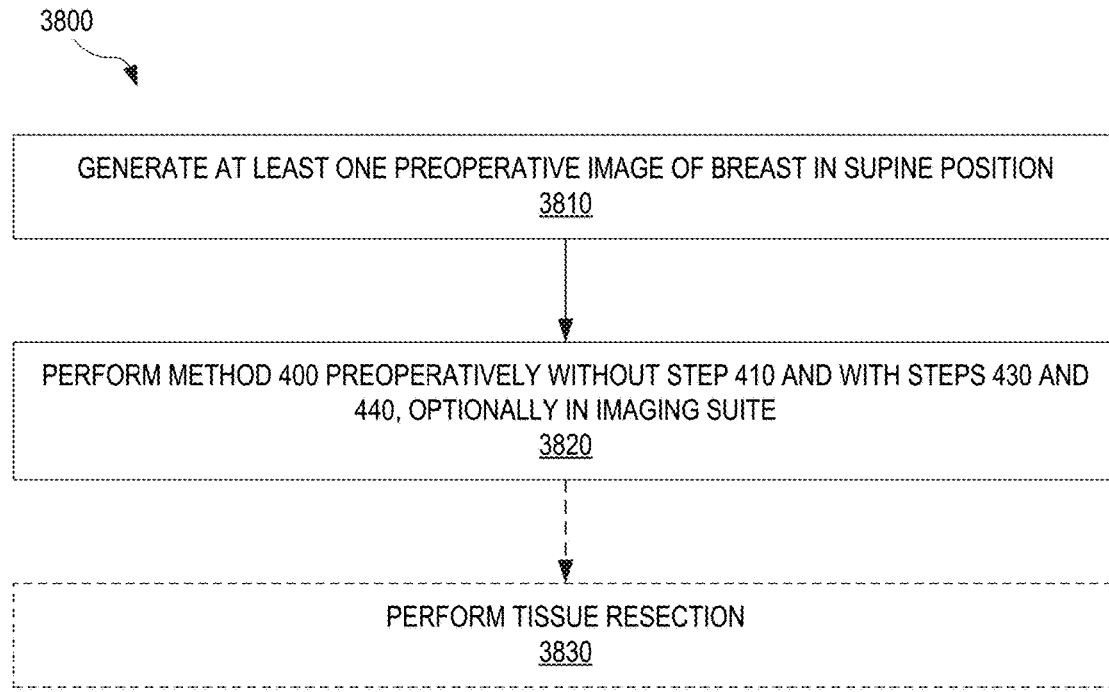
FIG. 38 illustrates a method for guiding resection of a tumor, wherein surgical guidance cues are transferred to the breast preoperatively, according to an embodiment.

FIG. 38 illustrates one exemplary method 3800 for guiding resection of a tumor 175, wherein surgical guidance cues 138 are transferred to breast 172 preoperatively, for example in the imaging suite. Method 3800 is an embodiment of method 400 and may be performed by system 100.

In a step 3810, method 3800 generates at least one preoperative supine image 158 or 358 of breast 172. Step 3810 is an embodiment of step 410. In a step 3820, method 3800 performs method 400 without step 410 and with steps 430 and 440. Step 3820 is performed preoperatively with breast 172 in the position used during step 3810. Step 3820 may be performed in the imaging suite. Surgical guidance cues 138 are transferred to breast 172 while breast 172 is in the position used for image capture in step 3810. In an optional step 3830, surgeon 180 performs the tissue resection procedure to resect tumor 175, while utilizing surgical guidance cues 138 transferred to breast 172 in step 3820. Tissue displacement between steps 3820 and 3830 does not adversely impact the accuracy of surgical guidance cues 138 transferred to breast 172.

Each of methods 3200, 3300, 3400, 3600, 3700, and 3800 may, for example, be extended to guide tumor resection from other body parts and organs, such as the brain or the liver, as well as guide biopsy procedures of, e.g., muscle or bone. As such, As such, tumor 175 may be generalized to local tissue of patient 170, breast 172 may be generalized to a portion of patient 170 associated with the resection surgery, surface 174 may be generalized to be a surface of patient 170 near the local tissue and including the incision site for removing the local tissue, and supine image 158 may be generalized to an image of the portion of patient 170 associated with the tissue resection procedure positioned as during the tissue resection procedure. Each of methods 3200, 3300, 3400, and 3500 may further be used to guide local delivery of markers or a therapeutic agent to patient 170.

Combinations of Features

Features described above as well as those claimed below may be combined in various ways without departing from the scope hereof. For example, it will be appreciated that aspects of one system, or method, for guiding tissue resection, described herein, may incorporate or swap features of another system, or method, for guiding tissue resection, described herein. The following examples illustrate some possible, non-limiting combinations of embodiments described above. It should be clear that many other changes and modifications may be made to the systems and methods herein without departing from the spirit and scope of this invention:

(A1) A method for guiding resection of local tissue from a patient may include (a) generating at least one first image, of the patient, including image of the local tissue and image of at least a portion of surface of the patient, (b) automatically determining, at least in part based upon the first image, a plurality of surgical guidance cues indicating three-dimensional spatial properties associated with the local tissue, and (c) generating a visualization of the surgical guidance cues relative to the surface.

(A2) In the method denoted as (A1), the step of generating at least one first image may include (a) capturing at least one volumetric image, of the patient, including the image of the local tissue, and (b) capturing at least one surface image, of the patient, including the image of at least a portion of surface of the patient.

(A3) In the method denoted as (A1), the step of generating at least one first image may include capturing at least one volumetric image, of portion of the patient, including the image of a local tissue and the image of at least a portion of surface of the patient.

(A4) In the method denoted as (A1), the step of generating at least one first image may include (a) capturing at least one second image of the patient when the patient is in a second position, the second image including a second-position image of the local tissue and second-position image of at least a portion of the surface, (b) capturing at least one surface image of the patient when the local tissue and the portion of the surface is in a first position associated with the resection, and (c) transforming the second image to register the surface as captured in the second image to the surface as captured in the surface image, to produce the first image.

(A5) In the method denoted as (A4), the local tissue may be a tumor in a breast of the patient, each of the first position and the second position may be a supine position, and the step of transforming may include producing the first image by performing a rigid-body transformation of the second image to register the surface as captured in the second image to the surface as captured in the surface image.

(A6) In the method denoted as (A4), the local tissue may be a tumor in a breast of the patient, the first position may be a supine position, the second position being a prone position, and the step of transforming may include producing the first image by deformably transforming of the second image to register the surface as captured in the second image to the surface as captured in the surface image while accounting for tissue displacement of the breast between the prone position and the supine position.

(A7) In any of the methods denoted as (A1) through (A6), the step of generating a visualization may include generating a model of the surface, and superimposing at least one of the surgical guidance cues on the model of the surface.

(A8) In the method denoted as (A7), the step of superimposing may include superimposing, onto the model, an incision site for resection surgery, and projection of the local tissue onto the surface along direction from the local tissue to incision site.

(A9) In either of both of the methods denoted as (A7) and (A8), the step of generating a visualization may further include indicating, in the model, injection location and direction, relative to the surface, for injection of a dye into the local tissue to indicate at least a peripheral portion of the local tissue so as to provide an assessment tool for the resection, wherein the injection location and direction are part of the surgical guidance cues.

(A10) In any of the methods denoted as (A7) through (A9), the step of generating a visualization may further include communicating the model, with the at least one of the surgical guidance cues superimposed thereon, to a tracking stylus device to track position of the tracking stylus with respect to the patient and visualizing the position of the stylus in the model.

(A11) The method denoted as (A10) may further include transferring at least one of the surgical cues to the surface using the stylus.

(A12) Any of the methods denoted as (A7) through (A9) may further include communicating the model, with the at least one of the surgical guidance cues superimposed thereon, to an augmented reality device.

(A13) The method denoted as (A12) may further include, in the step of generating a visualization (a) generating a volumetric model of a portion of the patient, the volumetric model including a model of the local tissue and a model of the surface, and (b) superimposing the surgical guidance cues on the volumetric model, and also communicating the volumetric model, with the surgical guidance cues superimposed thereon, to an augmented reality device.

(A14) In any of the methods denoted as (A1) through (A6), the local tissue may be a tumor in a breast of the patient, the first image may be of the breast when the patient is in supine position, and the method may further include manufacturing a locator form that fits the breast, when in supine position, wherein the locator form includes features indicating at least a portion of the surgical guidance cues.

(A15) In the method denoted as (A14), the locator form may indicate incision site for resection surgery and projection of the tumor onto the surface along direction from tumor to incision site.

(A16) In either of both of the methods denoted as (A14) and (A15), the step of manufacturing may further include incorporating a raised needle port into the locator form to guide a needle to the tumor, such that dye injected by a syringe through the needle into the tumor provides an assessment tool or a surgical guidance tool for the resection, the raised needle port being one of the surgical guidance cues.

(A17) In any of the methods denoted as (A14) through (A16), the step of manufacturing may further include incorporating a raised needle port into the locator form at incision site for resection surgery to guide a hook wire from the incision site to the tumor, the hook wire being one of the surgical guidance cues.

(A18) Any of the methods denoted as (A1) through (A17) may further include (a) in the step of automatically determining, analyzing the first image to automatically determine an optimal incision site, and (b) in the step of generating a visualization, indicating the optimal incision site relative to the surface.

(A19) Any of the methods denoted as (A1) through (A17) may further include (a) receiving a user-defined incision site location, and (b) in the step of automatically determining, determining the plurality of surgical guidance cues based upon the user-defined incision site location and the first image.

(A20) Any of the methods denoted as (A1) through (A19) may further include performing a tissue resection procedure that utilizes the surgical guidance cues to resect the local tissue.

(B1) A method for generating surgical guidance cues for resection of a tumor from a breast may include (a) processing at least one supine image of a breast to determine three-dimensional spatial properties of the tumor, and (b) based upon the three-dimensional spatial properties, generating a plurality of surgical guidance cues indicating the three-dimensional spatial properties of the tumor with respect to surface of the breast.

(B2) In the method denoted as (B1), the step of processing may include determining centroid position of the tumor and determining a vector from the centroid position to incision site for resection surgery.

(B3) In either or both of the methods denoted as (B1) and (B2), the step of generating may include determining the incision site as a first surface point of surface of the breast closest to perimeter of the tumor.

(B4) In any of the methods denoted as (B1) through (B3), the step of generating may include determining projection of the tumor onto the surface of the breast along the vector.

(B5) The method denoted as (B4) may further include transferring the projection onto the surface of the breast by indicating at least a plurality of margins of the projection on the surface of the breast.

(B6) In the method denoted as (B5), the margins may include cranial margin, caudal margin, lateral margin, and medial margin of the projection.

(B7) Any of the methods denoted as (B1) through (B6) may include (a) in the step of processing, determining (i) an anterior point of the perimeter where the vector intersects the perimeter, and (ii) a posterior point of the perimeter where the perimeter intersects a line passing through the centroid position, a first surface point of surface of the breast closest to perimeter of the tumor, and chest wall associated with the breast, and (b) in the step of generating, determining (i) anterior margin of the tumor as distance between the anterior point and the first surface point, and (ii) posterior margin of the tumor as distance between the posterior point and the chest wall along the line.

(B8) Any of the methods denoted as (B1) through (B7) may further include performing a tissue resection procedure that utilizes the surgical guidance cues to resect the local tissue.

(C1) A system for generating surgical guidance cues for resection of a local tissue from a patient may include (a) a location module for processing at least one image of the patient to determine three-dimensional spatial properties of the local tissue, and (b) a surgical cue generator for generating the surgical guidance cues based upon the three-dimensional spatial properties.

(C2) In the system denoted as (C1), the location module may include a position calculator for determining centroid position of the local tissue from the image.

(C3) In either or both of the systems denoted as (C1) and (C2), the location module may further including a direction calculator for determining a vector from the centroid position to incision site for resection surgery.

(C4) In any of the systems denoted as (C1) through (C3), the surgical cue generator may include an incision site calculator for determining the incision site as point on surface of the patient closest to perimeter of the local tissue.

(C5) Any of the systems denoted as (C1) through (C4) may further include an interface for receiving location information for the incision site.

(C6) In any of the systems denoted as (C1) through (C5), the surgical cue generator may include a projection calculator for determining projection of the local tissue onto surface of the patient along a vector from the centroid position to incision site for resection surgery.

(C8) In any of the systems denoted as (C1) through (C7), the local tissue may be a tumor in a breast of the patient and the surgical cue generator may include a volumetric margin calculator for determining (a) anterior margin of the tumor as distance between the anterior point and incision site for resection surgery, and (b) posterior margin of the tumor as distance between the posterior point and the chest wall along a line passing through the centroid position and the incision site.

(C9) In any of the systems denoted as (C1) through (C8), the surgical cue generator may include a projection margin calculator for determining cranial, caudal, lateral, and medial margins of a projection of the local tissue onto surface of the patient along a vector from the centroid position to incision site for resection surgery.

(C10) Any of the systems denoted as (C1) through (C9) may further include a visualization module for generating a model of the surface of the patient with the surgical guidance cues superimposed thereon.

(C11) In any of the systems denoted as (C1) through (C10), the local tissue may be a tumor in a breast of the patient and the at least one image may include at least one supine image of the breast.

(C12) In any of the systems denoted as (C1) through (C11), the at least one image may include (a) a volumetric image of a portion of the patient including the local tissue and (b) a three-dimensional surface image of surface of the patient including location of incision site used for resection surgery, and the system may further include an image registration module for registering the volumetric image to the surface image.

(C13) In the system denoted as (C12), the image registration module may include a rigid body transformation module for rigidly translating or rigidly scaling the volumetric image to register the volumetric image to the surface image.

(C14) In the system denoted as (C13), the local tissue may be a tumor in a breast of the patient, the volumetric image may be of the breast in a first supine position, and the three-dimensional surface image may be of the breast in a second supine position.

(C15) In any of the systems denoted as (C12) through (C14), the image registration module may include a deformable transformation module for deformably transforming the volumetric image to register the volumetric image to the surface image.

(C16) In the system denoted as (C15), the local tissue may be a tumor in a breast of the patient, the volumetric image may be of the breast in prone position, and the three-dimensional surface image may be of the breast in supine position.

(C17) In any of the systems denoted as (C1) through (C16), the at least one image may include (a) a volumetric image of a portion of the patient including the local tissue and (b) a three-dimensional surface image of surface of the patient including location of incision site used for resection surgery, and the system may further include an optical surface imager for generating the three-dimensional surface image.

(C18) In the system denoted as (C17), the optical surface imager may be a structured-light imager for (a) illuminating the surface with structured light, (b) capturing one or more reflection images of the structured light reflected by the surface, and (c) processing the one or more reflection images to determine the three-dimensional surface image.

(C19) In the system denoted as (C17), the optical surface imager may be a stereo camera.

(D1) A patient-specific locator form for guiding resection of a tumor from a breast may include (a) a first locator form surface matching surface of the breast, when in supine position, such that the patient-specific locator form fits the breast when placed on the breast in supine position, and (b) a plurality of features indicating a plurality of surgical guidance cues, respectively.

(D2) The patient-specific locator form denoted (D1) may further include one or more markers positioned to match one or more respective fiducials on the breast, such that the markers aid positioning of the patient-specific locator form on the breast.

(D3) In either of both of the patient-specific locator forms denoted as (D1) and (D2), the plurality of features may include at least one raised needle port, each having shape and position to passively direct a respective needle to a respective location associated with the tumor when the patient-specific locator form is placed on the breast.

(D4) In the patient-specific locator form denoted as (D3), each of the at least one raised needle port may have an elongated cannulation that defines direction of the respective needle when inserted in the elongated cannulation.

(D5) In either of both of the patient-specific locator forms denoted as (D3) and (D4), one of the at least one raised needle port may be located at incision site for resection surgery.

(D6) In any of the patient-specific locator forms denoted as (D1) through (D4), the plurality of features may include a cut-out at incision site for resection surgery to provide access to the tumor when the patient-specific locator form is placed on the breast.

(D7) In the patient-specific locator form denoted as (D6), the cut-out may have outline matching projection of the tumor onto the surface of the breast along direction from the tumor to the incision site.

(D8) Any of the patient-specific locator forms denoted as (D1) through (D7) may further include a material model of the tumor, and at least one rod for connecting the material model to the first locator form surface to indicate position of tumor relative to the surface of the breast.

(D9) In the patient-specific locator form denoted as (D8), the material model of the tumor may include one or more features to indicate one or more respective margins.

(D10) In either or both of the patient-specific locator forms denoted as (D8) and (D9), a portion of the patient-specific locator form associated with the first locator form surface may be at least partly transmissive to light such that the material model is visible through the first locator form surface when the material model is connected to the first locator form surface via the at least one rod.

(E1) A method for manufacturing a patient-specific locator form for guiding resection of a tumor from a breast may include additively manufacturing, based upon three-dimensional image of surface of the breast in supine position and a plurality of surgical guidance cues, a three-dimensional locator form that (a) has first locator form surface matching the surface of the breast and (b) includes a plurality of features indicating the plurality of surgical guidance cues, respectively.

(E2) The method denoted as (E1) may further include capturing the three-dimensional image of the surface when the breast is in supine position.

(E3) In either or both of the methods denoted as (E1) and (E2), the step of additively manufacturing may include additively manufacturing at least one raised needle port in the locator form, wherein each of the at least one raised needle ports has shape and position to passively direct a needle to a respective location associated with the tumor when the locator form is placed on the breast.

(E4) In the method denoted as (E3), the step of additively manufacturing at least one raised needle port may include additively manufacturing, in the locator form at incision site for resection surgery, a needle port having shape to passively guide a hook wire from the incision site to anterior margin of the tumor.

(E5) In the method denoted as (E3), the step of additively manufacturing at least one raised needle port may include additively manufacturing, in the locator form at incision site for resection surgery, a needle port having shape to passively guide a hook wire from the incision site through center of the tumor to posterior surface of the tumor.

(E6) In either or both of the methods denoted as (E1) and (E2), the step of additively manufacturing may include forming a cut-out at incision site for resection surgery to provide access to the tumor when the locator form is placed on the breast.

(E7) Any of the methods denoted as (E1) through (E6) may further include determining the incision site as a first surface point of surface of the breast closest to perimeter of the tumor, based upon the three-dimensional surface image and a volumetric image of the breast.

(E8) Any of the methods denoted as (E1) through (E6) may further include receiving position of a user-specified incision site.

(E9) In the method denoted as (E6), the step of forming a cut-out may include forming the cut-out to match projection of tumor onto the surface of the breast.

(E10) Any of the methods denoted as (E1) through (E9) may further include incorporating a first feature in the locator form to indicate, when the locator form is placed on the breast, projection of the tumor onto the surface of the breast.

(E11) Either or both of the methods denoted as (E9) and (E10) may further include determining the projection from the three-dimensional surface image and a volumetric image of the breast as projection of tumor onto the surface of the breast along direction from centroid of tumor to incision site for resection surgery.

(E12) Any of the methods denoted as (E1) through (E11) may further include analyzing the three-dimensional surface image and at least one volumetric image of the breast to determine the plurality of first surgical guidance cues.

(E13) Any of the methods denoted as (E1) through (E12) may further include manufacturing a material model of the tumor indicating one or more margins of the tumor.

(E14) The method denoted as (E13) may further include connecting the material model to the first locator form surface to indicate location of the tumor relative to the surface of the breast.

(F1) A patient-specific locator form for guiding resection of local tissue from a patient may include (a) a first locator form surface matching surface of the patient near location of the local tissue, such that the patient-specific locator form fits the surface, and (b) a plurality of features indicating a plurality of surgical guidance cues, respectively.

(F2) In the patient-specific locator form denoted as (F1), the local tissue may be a tumor in a breast of the patient, and the first locator form surface matching surface of the breast.

(F3) Either or both of the patient-specific locator forms denoted as (F1) and (F2) may further include one or more markers positioned to match one or more respective fiducials on the surface, such that the markers aid positioning of the patient-specific locator form on the surface.

(F4) In the patient-specific locator form denoted as (F3), the local tissue may be a tumor in a breast of the patient, the first locator form surface may match surface of the breast, and the markers may include an opening positioned to match nipple of the breast.

(F5) In any of the patient-specific locator forms denoted as (F1) through (F4), the plurality of features may include at least one raised needle port, each having shape and position to passively direct a respective needle to a respective location associated with the local tissue when the patient-specific locator form is placed on the surface.

(F6) In the patient-specific locator form denoted as (F5), each of the at least one raised needle port may have an elongated cannulation that defines direction of the respective needle when inserted in the elongated cannulation.

(F7) In either or both of the patient-specific locator forms denoted as (F5) and (F6), one of the at least one raised needle port may be located at incision site for resection surgery.

(F8) In any of the patient-specific locator forms denoted as (F5) through (F7), one of the at least one raised needle port being may include a removable spacer with length configured to (a) target one position within the patient when the spacer is in place, and (b) target another position within the patient when the spacer is removed.

(F9) In any of the patient-specific locator forms denoted as (F1) through (F8), the plurality of features may include a cut-out at incision site for tissue resection surgery to provide access to the local tissue when the patient-specific locator form is placed on the surface.

(F10) In the patient-specific locator form denoted as (F9), the cut-out may have outline matching projection of the local tissue onto the surface along direction from the local tissue to the incision site.

(F11) Any of the patient-specific locator forms denoted as (F1) through (F10) may further include a material model of the local tissue and at least one rod for connecting the material model to the first locator form surface to indicate position of local tissue relative to the surface.

(F12) In the patient-specific locator form denoted as (F11), the material model of the local tissue may include one or more features to indicate one or more respective margins of the local tissue.

(F13) In either or both of the patient-specific locator forms denoted as (F11) and (F12), a portion of the patient-specific locator form associated with the first locator form surface may be at least partly transmissive to light such that the material model is visible through the first locator form surface when the material model is connected to the first locator form surface via the at least one rod.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present method and device, which, as a matter of language, might be said to fall therebetween.

What is claimed is:

1. A patient-specific device for guiding resection of a tumor located in a breast of a patient, comprising:
    a locator form having a locator-form surface matching a surface of the breast of the patient near the tumor's location when the breast is imaged in a supine preoperative position, such that the locator form, when fit to the surface of the breast, restores the breast to the supine preoperative position; and
    a surgical guidance cue integrally formed with the locator form and based on images including only preoperative images of the breast in the supine preoperative position, to indicate a spatial property of the tumor in the supine preoperative position.

2. The patient-specific device of claim 1, the locator form including an additional locator-form surface adjoining and surrounding the locator-form surface, and being configured to match a shape of an adjoining anatomical structure of the patient.

3. The patient-specific device of claim 2, the adjoining anatomical structure being a region below the inframammary fold of the breast.

4. The patient-specific device of claim 1, the surgical guidance cue including a fiducial positioned to match one or more respective fiducials on the surface of the breast, such that the fiducial aids in positioning of the patient-specific device on the surface of the breast.

5. The patient-specific device of claim 1, the surgical guidance cue including a raised needle port having shape and position to passively direct a needle to one of (i) a location associated with the tumor and (ii) a margin of the tumor, when the patient-specific device is placed on the surface of the breast.

6. A method for guiding resection of a tumor comprising:
    generating a supine image of a breast in a supine position, the breast having a breast surface;
    generating, from the supine image, a surface model of the breast surface and a surface model of the tumor;
    determining, based at least in part upon the surface model of the breast surface and the surface model of the tumor, a plurality of surgical guidance cues indicating three-dimensional spatial properties associated with the tumor; and
    generating a visualization of the surgical guidance cues relative to the breast surface at least in part by superimposing the surgical guidance cues on the surface model of the breast surface to enable transfer of the surgical guidance cues to the breast;
    manufacturing a locator form that fits the breast, when in the supine position, and an adjoining anatomical structure at least partially surrounding the breast, the locator form including features indicating at least a portion of the surgical guidance cues; and
    restoring the breast to its position in the supine image by aligning the locator form with respect to the breast and the adjoining anatomical structure.

7. The method of claim 6, the step of generating a visualization comprising:
    generating a model of the breast surface, and superimposing the plurality of surgical guidance cues onto the model of the breast surface, the plurality of surgical guidance cues including at least one of (a) an incision site and (b) projection of the tumor onto the breast surface along a direction from local tissue to the incision site.

8. The method of claim 6, the tumor being in a patient, the step of generating the supine image comprising:
capturing a volumetric image that includes a supine image of the tumor; and
capturing a surface image, of the patient, that includes an image of at least a portion of the breast surface.

9. The method of claim 6, the tumor being in the breast, the step of generating the supine image comprising:
capturing a volumetric image including an image of a portion of the breast and an image of at least a portion of the breast surface.

10. The method of claim 6, the tumor being in a patient, the step of generating the supine image comprising:
capturing a second image of the patient when the patient is in a second position, the second image including a second-position image of the tumor and a second-position image of at least a portion of the breast surface;
capturing a surface image of the patient when the tumor and the portion of the breast surface is in a first position associated with the resection; and
transforming the second image to register the breast surface as captured in the second image to the breast surface as captured in the surface image, to produce the supine image.

11. The method of claim 10, the second position being a supine position, the step of transforming comprising producing the supine image by performing a rigid-body transformation of the second image to register the breast surface as captured in the second image to the portion of the breast surface as captured in the surface image.

12. The method of claim 10, the second position being a prone position, the step of transforming comprising producing the supine image by deformably transforming of the second image to register the breast surface as captured in the second image to the portion of the breast surface as captured in the surface image while accounting for tissue displacement of the breast between the prone position and the supine position.

13. The method of claim 6, further comprising:
receiving a user-defined incision site location; and
the step of determining comprising determining the plurality of surgical guidance cues based upon the user-defined incision site location and the supine image.

14. The method of claim 6, performing a tissue resection procedure that utilizes the plurality of surgical guidance cues to resect the tumor.

15. The patient-specific device of claim 1, further comprising additional surgical guidance cues that, with the surgical guidance cue, indicate a margin of the tumor.

16. The patient-specific device of claim 15, the margin incorporating a safety margin.

17. The patient-specific device of claim 1, further comprising additional surgical guidance cues that, with the surgical guidance cue, indicate a perimeter of the tumor.

18. The patient-specific device of claim 1, further comprising additional surgical guidance cues that, with the surgical guidance cue, indicate a centroid position of the tumor.

* * * * *